(12) United States Patent
Hess et al.

(10) Patent No.: US 7,924,432 B2
(45) Date of Patent: Apr. 12, 2011

(54) THREE-DIMENSIONAL INTERFEROMETRIC MICROSCOPY

(75) Inventors: Harald F. Hess, Leesburg, VA (US); Gleb Shtengel, Ashburn, VA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 1 day.

(21) Appl. No.: 12/556,707

(22) Filed: Sep. 10, 2009

(65) Prior Publication Data

US 2010/0231922 A1 Sep. 16, 2010

Related U.S. Application Data

(63) Continuation-in-part of application No. 11/961,601, filed on Dec. 20, 2007.

(60) Provisional application No. 60/871,366, filed on Dec. 21, 2006, provisional application No. 60/908,307, filed on Mar. 27, 2007.

(51) Int. Cl.
*G01B 11/02* (2006.01)
*G02B 21/00* (2006.01)

(52) U.S. Cl. ...................... 356/496; 359/370

(58) Field of Classification Search .............. 356/456, 356/496; 359/370
See application file for complete search history.

(56) References Cited

U.S. PATENT DOCUMENTS

| | | | | |
|---|---|---|---|---|
| 5,671,085 A * | 9/1997 | Gustafsson et al. | ......... | 359/385 |
| 6,570,705 B2 * | 5/2003 | Bewersdorf et al. | ......... | 359/388 |
| 7,064,824 B2 | 6/2006 | Hell | | |
| 7,274,506 B2 * | 9/2007 | Engelhardt | .................. | 359/370 |
| 7,535,012 B2 | 5/2009 | Betzig et al. | | |
| 7,573,577 B2 * | 8/2009 | Martinez | ...................... | 356/451 |
| 2001/0012151 A1 * | 8/2001 | Knebel | ......................... | 359/368 |
| 2002/0105722 A1 * | 8/2002 | Bewersdorf et al. | ......... | 359/370 |
| 2006/0038993 A1 | 2/2006 | Hell | | |

OTHER PUBLICATIONS

Sri Rama Prasanna Pavini et al., "Three-dimensional, single-molecule fluorescence imaging beyond the diffraction limit by using a double-helix point spread function," PNAS, Mar. 3, 2009, vol. 106, No. 9, pp. 2995-2999.
Manuel F. Juette et al., "Three-dimensional sub-100 nm resolution fluorescence microscopy of thick samples," Nature Methods, Advance Online Publication, May 11, 2008, pp. 1-3.
Manuel F. Juette et al., "Three-dimensional sub-100 nm resolution fluorescence microscopy of thick samples," Supplementary figures and text, Nature Methods, Advance Online Publication, May 11, 2008, 11 pages.
Bo Huang et al., "Three-Dimensional Super-Resolution Imaging by Stochastic Optical Reconstruction Microscopy," Sciencexpress, Jan. 3, 2008, pp. 1-7. Bo Huang et al., "Supporting Online Material for Three-Dimensional Super-Resolution Imaging by Stochastic Optical Reconstruction Microscopy," Sciencexpress, Jan. 3, 2008, 8 pages.

* cited by examiner

*Primary Examiner* — Michael A Lyons
(74) *Attorney, Agent, or Firm* — DiBerardino Law LLC

(57) ABSTRACT

A statistically sparse subset of switchable optical sources in a sample is activated, and the activated switchable optical sources are excited such that optical beams are emitted from the activated switchable optical sources along at least two optical paths. A first wavefront modification in a first optical beam emitted from the activated switchable optical sources along a first optical path is introduced and a second wavefront modification in a second optical beam emitted from the activated switchable optical sources along a second optical path is introduced, the second wavefront modification being distinct from the first wavefront modification. The first and second optical beams are interfered with each other to produce a plurality of output beams, and three-dimensional position information of the optical sources is determined based on an intensity of each output beam from the plurality of output beams.

28 Claims, 40 Drawing Sheets

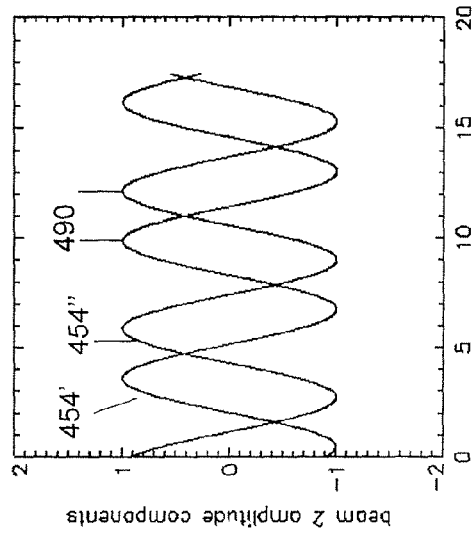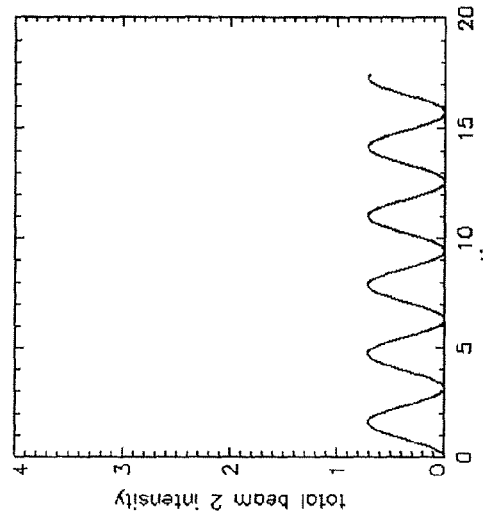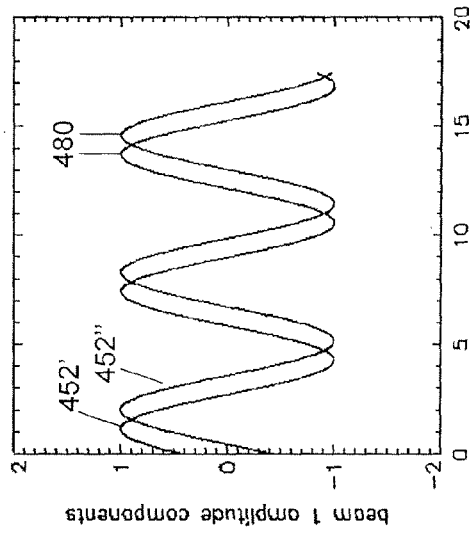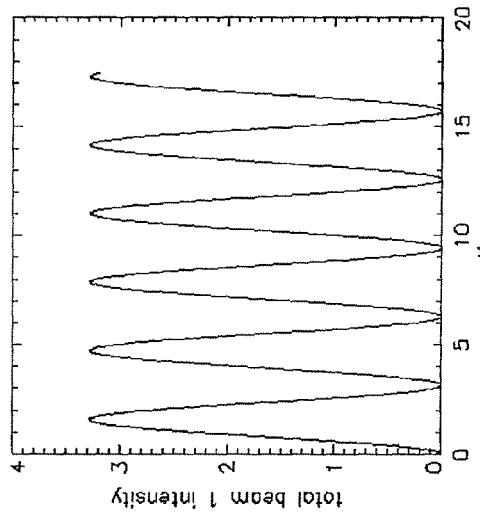

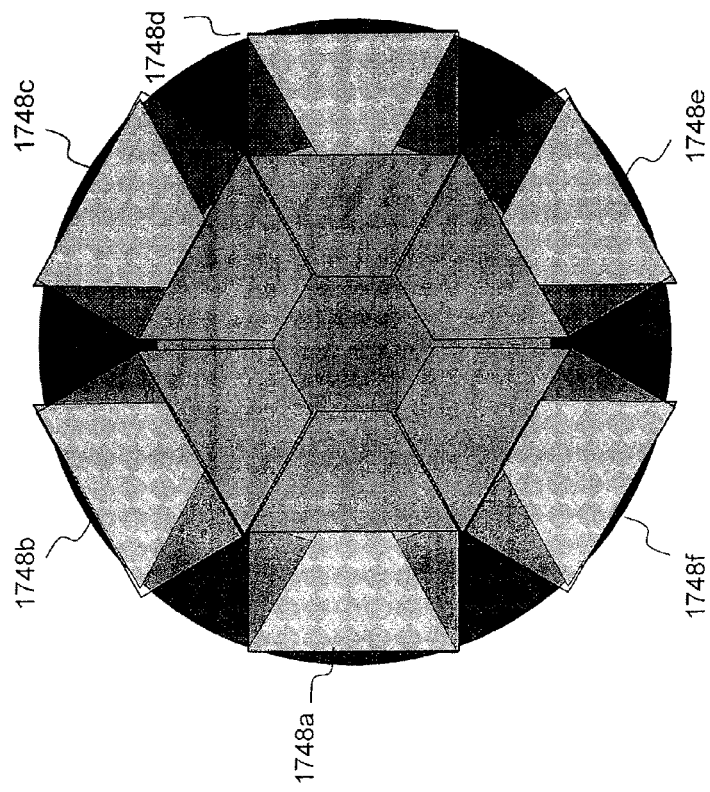
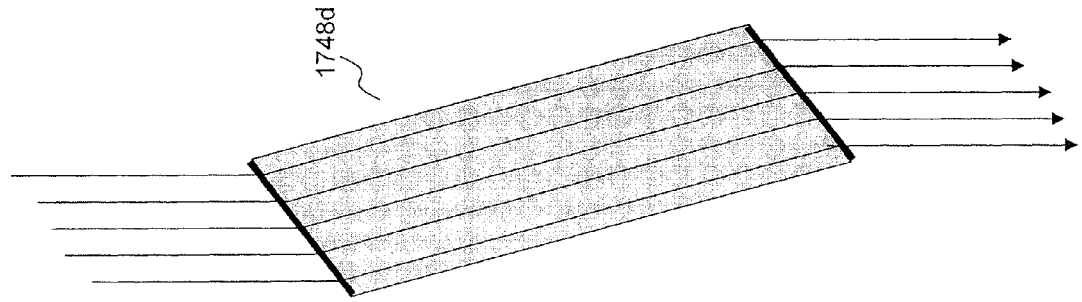
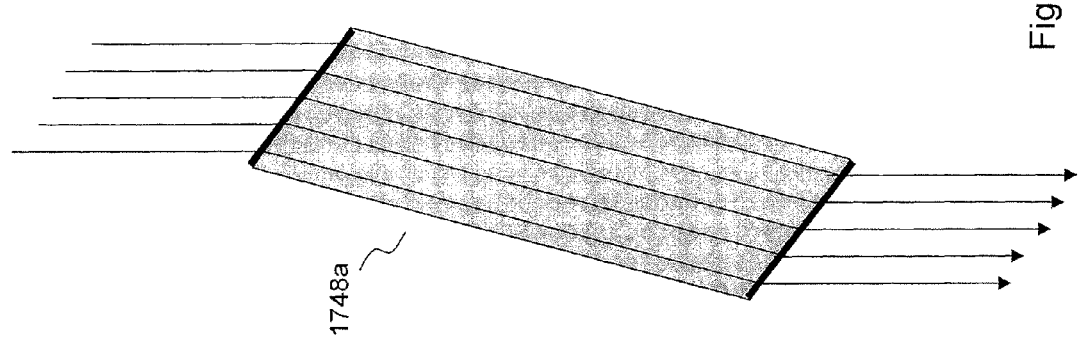
Fig. 20
Fig. 19

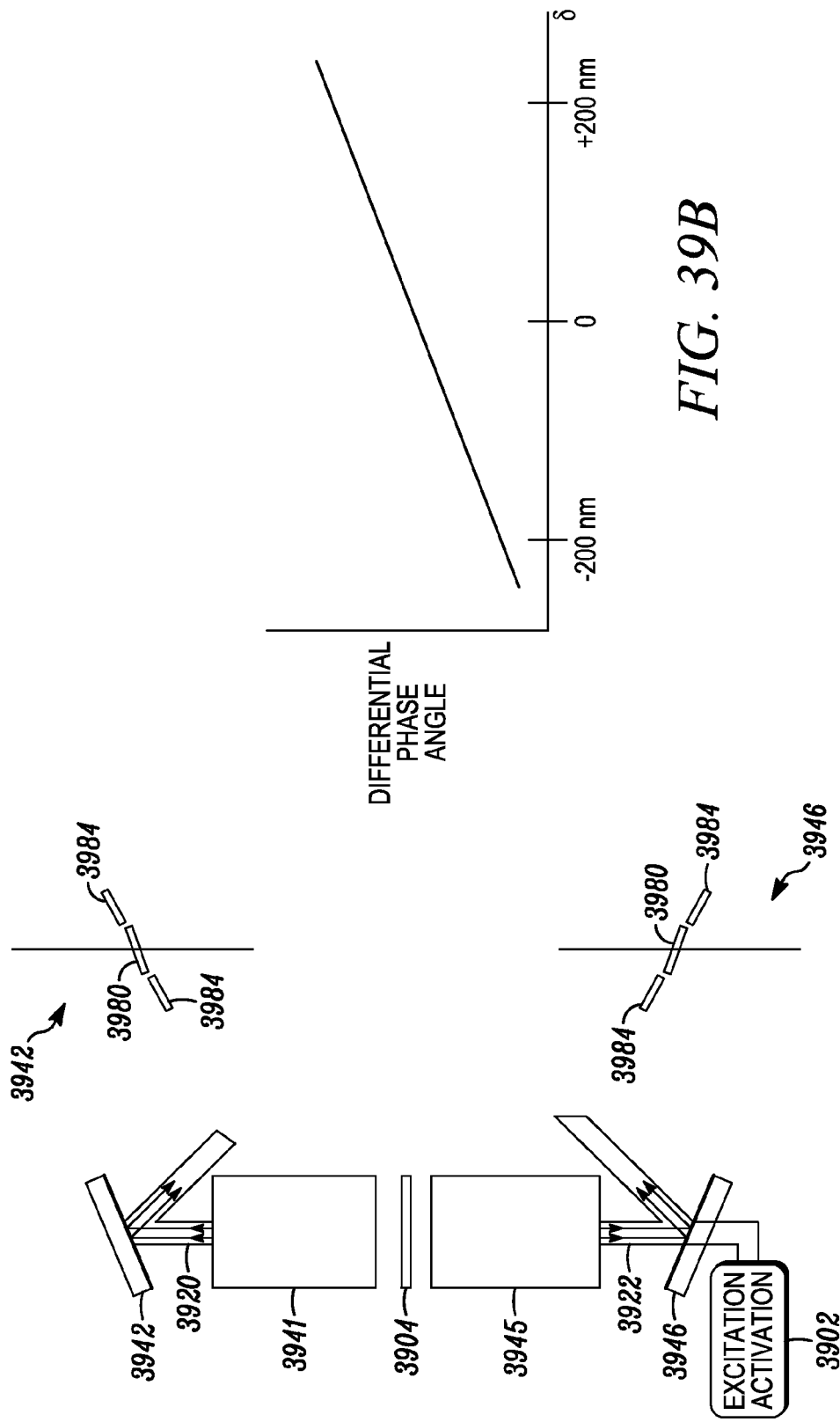

THREE-DIMENSIONAL INTERFEROMETRIC MICROSCOPY

CROSS-REFERENCE TO RELATED APPLICATION

This application is a continuation-in-part of U.S. application Ser. No. 11/961,601, filed on Dec. 20, 2007 and entitled "Systems and Methods for 3-Dimensional Interferometric Microscopy," which claims priority to U.S. Application No. 60/871,366, filed on Dec. 21, 2006 and entitled "System and Methods for 3-Dimensional Interferometric Microscopy" and to U.S. Application No. 60/908,307, filed on Mar. 27, 2007 and entitled "System and Methods for 3-Dimensional Interferometric Microscopy." All of these applications are incorporated herein by reference in their entirety.

TECHNICAL FIELD

The disclosed subject matter relates to interferometric microscopy including, for example, interferometric microscopy of samples that include or are labeled with spatially resolvable point sources.

BACKGROUND

Microscopy systems that measure interferometric phase are known. For example, one known microscopy system measures interferometric phase by illuminating an extended surface of an object with an external light source. Light reflected from the sample interferes with a reference beam in a beam splitter. The interfered beam is imaged onto a detector. The optical path difference between the reference beam and the sample beam can modulate the amplitude of the output interfered beam and provide a measure of an object height. Also known are microscopy systems that interfere two beams from a sample via opposing objectives to measure only one interfered output beam.

SUMMARY

In one general aspect, an optical source in a sample that extends generally along a sample plane defined by first and second orthogonal dimensions is optically actuated to cause the optical source to emit optical beams in a plurality of propagation directions. Two or more optical beams emitted from the optical source are interfered with each other to produce a plurality of output beams directed to a plurality of detectors. A position of the optical source in the first orthogonal dimension and the second orthogonal dimension is determined based on a center region of an image of each output beam from the plurality of output beams. A set of possible positions of the optical source in a third orthogonal dimension that is perpendicular to the sample plane is determined based on separately detected intensities of each of the plurality of output beams. The shape of an image of one or more of an optical beam and an output beam is analyzed based on a wavefront modification that varies with the position of the optical source in the third orthogonal dimension. The wavefront modification is a modification of one or more of a curvature and a shape of a wavefront of at least one optical beam emitted from the optical source. The position of the optical source in the third orthogonal dimension is determined out of the possible set of positions based on the analyzed shape.

Implementations can include one or more of the following features. For example, the shape of the one or more images can be analyzed by comparing the wavefront modification with predetermined wavefront modifications. The shape of the one or more images can be analyzed by comparing the wavefront modification with modeled wavefront modifications. The shape of the one or more images can be analyzed by analyzing a complex phase that is induced by the wavefront modifications and varies with the position of the optical source in the third orthogonal dimension.

The position of the optical source in the third orthogonal dimension can be determined out of the possible set of positions by comparing the shape of the one or more images to predetermined shapes of images that are determined based on predetermined wavefront modifications.

The wavefront modification can be actively introduced in the at least one optical beam. The wavefront modification can be introduced in the at least one optical beam by introducing a separation along a propagation direction between focal planes each having a focus in a respective transverse direction relative to the beam propagation direction. The wavefront modification can be introduced in the at least one optical beam by introducing a curvature in the wavefront along one or more transverse directions relative to the beam propagation direction.

The wavefront modification can be introduced in the at least one optical beam by varying a brightness of the image of the at least one optical beam. The brightness of the image can be varied along one transverse direction in a way that is distinct from the second transverse direction of one or more of the optical beams and output beams.

In another general aspect, an apparatus includes an optical actuation system, an interference system, at least two detectors, and a processor. The optical actuation system is configured to cause an optical source in a sample that extends generally along a sample plane to emit optical beams in a plurality of optical paths. The interference system is configured to receive first and second optical beams emitted from the optical source, divide each of the optical beams into two or more divided beams, and combine at least two or more of the divided beams to form a plurality of combined beams. Each of the combined beams includes an interference between the two or more divided beams caused at least in part by a difference in a source phase between the optical beams due to a difference in the optical path length of the optical beams relative to the location of the optical source. The at least two detectors are configured to separately detect one or more of an intensity and a profile of each of the combined beams output from the interference system. The processor is configured to receive the output from the at least two detectors; calculate a position of the optical source in the sample plane to sub-diffractive accuracy based on a center region of an image of each combined beam; calculate a set of possible positions of the optical source in a third orthogonal dimension that is perpendicular to the sample plane based on separately detected intensities of each combined beam; analyze the shape of an image of one or more of an optical beam and a combined beam based on a wavefront modification that varies with the position of the optical source in the third orthogonal dimension; and determine the position of the optical source in the third orthogonal dimension out of the set of possible positions based on the analyzed shape. The wavefront modification is a modification of one or more of a curvature and a shape of a wavefront of at least one optical beam emitted from the optical source.

Implementations can include one or more of the following features. For example, the optical actuation system can be optically coupled to the sample and can be configured to activate a statistically sparse subset of switchable optical sources in the sample and to excite the activated switchable optical sources such that the optical beams are emitted from the activated switchable optical sources along at least two optical paths that are directed to the interference system.

The apparatus can also include first optical components configured to receive the first optical beam emitted along a first optical path and to at least redirect the first optical beam toward the interference system; and second optical components configured to receive the second optical beam emitted along a second optical path and to at least redirect the second optical beam toward the interference system.

The apparatus can include a wavefront modification system in at least one of the optical paths configured to introduce the variable wavefront modification of at least one optical beam. The wavefront modification system can include a defocusing system in at least one of the optical paths configured to separate focal planes along transverse directions of one or more optical beams and combined beams. The defocusing system can include a first defocusing system in a first optical path of a first optical beam between the optical source and the interference system and configured to separate focal planes along the transverse directions of the first optical beam; and a second defocusing system in a second optical path of a second optical beam between the optical source and the interference system and configured to separate focal planes along the transverse directions of the second optical beam. The defocusing system can be between the sample and the interference system.

In another general aspect, a method includes activating a statistically sparse subset of switchable optical sources in a sample; exciting the activated switchable optical sources such that optical beams are emitted from the activated switchable optical sources along at least two optical paths; introducing a first wavefront modification in a first optical beam emitted from the activated switchable optical sources along a first optical path and introducing a second wavefront modification in a second optical beam emitted from the activated switchable optical sources along a second optical path, the second wavefront modification being distinct from the first wavefront modification; interfering the first and second optical beams to produce a plurality of output beams; and determining three-dimensional position information of the optical sources based on an intensity of each output beam from the plurality of output beams.

Implementations can include one or more of the following features. For example, the second wavefront modification can be opposite in direction to the first wavefront modification.

The first wavefront modification can be introduced by shifting, by a first shift value, the focal plane of the first optical beam along a first transverse direction relative to the focal plane of the first optical beam along a second transverse direction, in which the first and second transverse directions are transverse to the first optical path.

The second wavefront modification can be introduced by shifting, by a second shift value, the focal plane of the second optical beam along a first transverse direction relative to the focal plane of the second optical beam along a second transverse direction, in which the first and second transverse directions are transverse to the second optical path and the second shift value is opposite to the first shift value.

The first wavefront modification can be introduced by under-focusing the first optical beam emitted from the activated switchable optical sources along at least one direction that is transverse to the first optical path; and the second wavefront modification can be introduced by over-focusing the second optical beam emitted from the activated switchable optical sources along at least one direction that is transverse to the second optical path.

The method can also include forming collimated optical beams before introducing the first and second wavefront modifications to the first and second optical beams.

The three-dimensional position information can be determined by determining the position of the optical source in a dimension that is perpendicular to a sample plane across which the sample generally extends.

The first wavefront modification can be introduced in the first optical beam by introducing a wavefront curvature in the first optical beam; and the second wavefront modification can be introduced in the second optical beam by introducing a wavefront curvature in the second optical beam.

Each wavefront modification can be a modification of one or more of a curvature and a shape of a wavefront of the respective optical beam.

In another general aspect, a method includes directing first and second optical beams emitted from an optical point source along first and second distinct directions associated with respective first and second distinct optical paths; shifting by a first shift value focal planes for transverse directions of the first optical beam in the first optical path and shifting by a second shift value focal planes for transverse directions of the second optical beam in the second optical path, in which the second shift value is opposite to the first shift value; after shifting the focal planes of the first and second optical beams, dividing each of the first and second optical beams into two or more divided beams and combining at least two or more of the divided beams to form a plurality of combined beams, in which each of the combined beams includes an interference between the two or more divided beams caused at least in part by a difference in the lengths of the optical paths of the first and second optical beams; separately detecting an image of each of the combined beams; determining a position of the optical source in a first orthogonal dimension and a second orthogonal dimension; and determining a position of the optical source in a third orthogonal dimension based on the separately detected images of each of the combined beams.

Implementations can include one or more of the following features. For example, the position of the optical source in the third orthogonal dimension can be determined based on the separately detected images of each of the combined beams includes determining the position of the optical source by comparing the intensities of separately detected images to predetermined values.

In some general aspects, an apparatus comprises an optical system with multiple detectors and a processor. The optical system is configured to produce images of an optical source in a first dimension and a second dimension substantially orthogonal to the first dimension at each detector at a given time. Each image from the images is based on an interference of an emission from the optical source, the emission forming two different optical beams. The processor is configured to calculate a position in a third dimension based on the images. The third dimension is substantially orthogonal to the first dimension and the second dimension.

In some general aspects, molecules of interest that are tagged with fluorescent labels can be localized in 3 dimensions to an accuracy better than the diffraction limit. In such implementations, the phase information associated with the image can be used to determine information about the position of a molecule in the z coordinate such that a 3D (three-dimensional) representation with sub-diffractive accuracy $<<\lambda/2$ in the 3 dimensions can be achieved. In other words, information about the position of a molecule in the third dimension (for example, the z coordinate) can be obtained from the same set of images that are used to obtain the information about the position of the molecule in the two other dimensions (for example, the x and y coordinates).

In some general aspects, at least two optical beams emitted from an optical point source are directed along at least two distinct directions, each direction being associated with a distinct optical path. Each of the optical beams is divided into two or more divided beams, and at least two or more of the divided beams are combined to form a plurality of combined beams, each of the combined beams including an interference between the two or more divided beams caused at least in part by a difference in source phase between the optical beams due to a difference in the optical path length of the optical beams. An intensity and an image profile of each of the combined beams is separately detected. A position of the optical source in a first orthogonal dimension and a second orthogonal dimension is determined, and a position of the optical source in a third orthogonal dimension is determined based on the separately detected intensities and image profiles of each combined beams.

Implementations can include one or more of the following features. The at least two optical emission beams can be directed by directing each of the at least two optical beams through opposing lenses. The at least two optical emission beams can be directed by directing each of the at least two optical beams through different portions of a lens. The intensity of each of the combined beams can be separately detected by simultaneously detecting the intensity of each of the combined beams. Each of the optical emission beams can be divided by dividing at least one of the optical emissions beams into three or more divided beams.

In another general aspect, an apparatus includes a beam splitter configured to receive at least two optical beams emitted from an optical point source along two distinct optical paths, divide each of the optical emission beams into two or more divided beams, and combine at least two or more of the divided beams to form a plurality of combined beams. Each of the combined beams includes an interference between the two or more divided beams caused at least in part by a difference in phase between the divided optical beams due to a difference in the optical path length of the optical beams. At least two detectors are configured to separately detect an intensity and image profile of each of the combined beams output from the beam splitter. A processor is configured to receive the output from the at least two detectors, and to calculate a position of the optical source in first, second, and third orthogonal dimensions to sub-diffractive accuracy.

In another general aspect, a statistically sparse subset of switchable optical sources in a sample are activated, the activated switchable optical sources are excited such that optical energy is emitted from the activated switchable optical sources in a plurality of directions, the optical energy emitted from the activated switchable optical sources in the plurality of directions is interfered to produce a plurality of output beams, and three-dimensional position information of the optical sources is determined based on an intensity and image profile of each output beam from the plurality of output beams.

DESCRIPTION OF DRAWINGS

FIGS. 7A and 7B are graphs displaying the phase of the beam intensities of the components for a given output beam detected at a respective detector of FIG. 6.

FIGS. 7C and 7D are graphs displaying the intensities of the output beams associated with FIGS. 7A and 7B, respectively.

FIG. 19 is a cross-sectional view of the annular expander shown in FIG. 18.

FIG. 20 is an end view of the annular expander shown in FIG. 18.

FIG. 39A is a block diagram of an exemplary portion of the interferometric microscope system of FIG. 28.

FIG. 39B is a generalized graph of a differential phase angle versus vertical position of the optical source of a sample in the system of FIG. 39A.

DESCRIPTION

Figure 1:
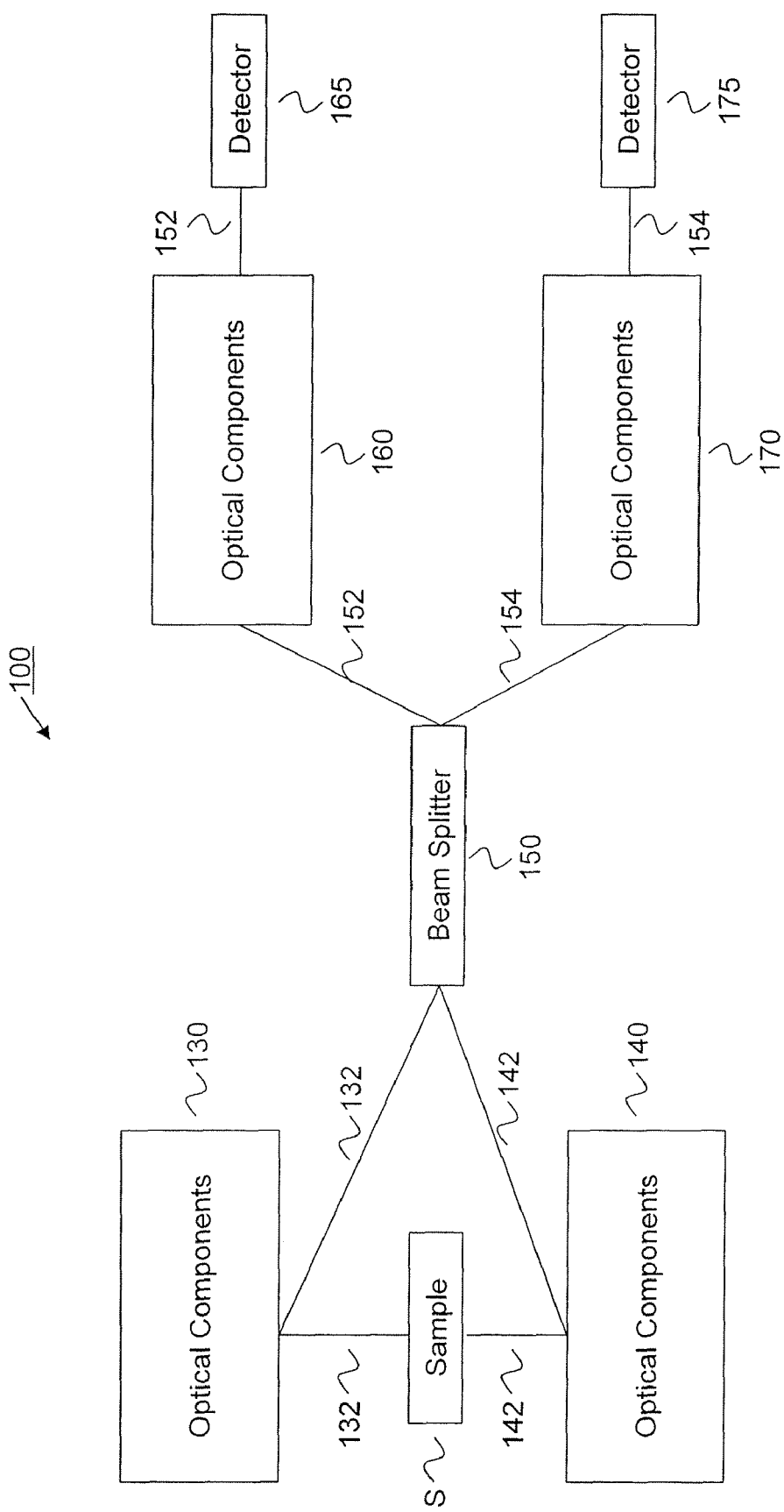
FIG. 1 is block diagram of a multi-phase interferometric microscopy system and a sample.

In broad terms, one or more implementations described herein can produce three-dimensional renderings of a sample with resolution better than known optical microscopy. In some implementations, a widefield interferometric microscope can measure a phase difference to determine position information of switchable optical sources in a sample in a third dimension (for example, along the z coordinate or vertical direction) while simultaneously measuring position information in the two other orthogonal dimensions (for example, along the x and y coordinates or along the sample plane). In some implementations, an interferometric microscope can measure samples containing or labeled with a collection of spatially resolvable point-sources such as samples that internally radiate light from photo-activated fluorescent labels in protein molecules.

For example, three-dimensional (3D) renderings of specific labeled proteins in a sample can be produced. Contrast can be given by specific labeled proteins and still be acquired with a specialized optical microscope. For example, one or more implementations can be used to locate a fluorescently labeled protein in a cell with full 3D location.

One known microscope system is the Photo-Activated Localization Microscopy ("PALM") system. The PALM system is described in the following references, which are incorporated herein by reference: U.S. Application No. 60/683,337, entitled "Optical Microscopy with Phototransformable Optical Labels" and filed May 23, 2005; U.S. Application No. 60/780,968, entitled "Imaging Intracellular Fluorescent Proteins at Near-Molecular Resolution" and filed Mar. 10, 2006; PCT Patent Application Serial No. PCT/US2006/019887, entitled "Optical Microscopy with Phototransformable Optical Labels," filed May 23, 2006 and published on Nov. 11, 2005 as PCT Publication No. WO/2006/127682; Betzig, E. et al., "Imaging Intracellular Fluorescent Proteins at Nanometer Resolution," Science, Vol. 313, Sep. 15, 2006; and Betzig, E. et al., "Supporting online Material for 'Imaging Intracellular Fluorescent Proteins at Nanometer Resolution'," Science Express, Aug. 10, 2006, [online] www.sciencemag.org/cgi/content/full/1127344/DC1 (collectively referred to herein as the "Betzig references").

The PALM system localizes molecules predominantly in two dimensions (2D), that is, in the x,y image plane (or sample plane) to provide high-resolution images that exceed that of diffraction-limited microscopes. In the 2D PALM system, switchable optical labels can be the photo activatable fluorescent proteins such as PA-GFP. PA-GFP is a photo activatable fluorescent protein mutant of GFP where irradiation with 405 nm light can transform it from a non-fluorescent version into an anionic form that absorbs excitation radiation at 500 nm and emits fluorescent radiation at 520 nm. Other photo-activatable proteins include Dronpa, Eos, PA-Cherry, Kaede, Kikume, Kindling-FP, PA-CFP, many of which are useable in monomeric, dimeric and tetrameric forms. Such proteins can be genetically expressed and genetically attached to label a protein of interest. This enables protein specific images to be constructed. Various caged dye molecules can also be used but they typically require immuno-labeling or alternate attachment schemes. Because some of these proteins/labels have sufficiently different photophysical properties such as emission wavelength, excitation wavelength, or bleaching rates, it is possible to make images with two different switchable optical labels. In this case, the addition of dichroic mirrors in the beam paths can result in a new second or even third set of images for this 3D interferometric microscopy. Sequencing the acquisition to image and bleach one protein and then image the second is another way to image different labeled proteins.

By convention, the z position of the labeled molecule is along the direction of the optical axis of the objective or objectives, and the x and y positions are along x and y directions that extend along the plane of the sample, the x and y directions are orthogonal to the z direction.

One way to obtain information about the location of labeled molecules in the third dimension (the z direction) uses the phase angle information of the optical path length difference such that both two-dimensional intensity image, from which the x,y position of labeled molecules can be determined, and the phase dependent images, from which the z position of the labeled molecules can be determined, can be simultaneously acquired and can be reconstructed. In other words, two or more emission beams from a sample are further split into two or more beams and pairwise interfered with each other (based on their differing phases) and the resulting interfered beams form images that are recorded simultaneously to reconstruct the path length difference (that is, the z position) of the localized sources of a sample. In addition, in some implementations, the interference amplitude can also be extracted and used as a supplemental measure of vertical position.

Such implementations are advantageous in many respects. For example, as mentioned above, in some implementations described herein, the phase difference can be measured to determine position information in the third dimension (for example, the z direction) while simultaneously measuring position information in the two other dimensions (for example, the x and y directions). This allows for a measurement of all three orthogonal dimensions that can be more accurate than known systems where these measurements occur at different times. Such a measurement technique described herein can be particularly advantageous, for example, for samples that are not static such as photo-activated samples that have a time-varying brightness.

As also mentioned above, in some implementations described herein, the component of the sample being measured is separable and identifiable as a sub-diffractive sized point source. This allows for a measurement that can be well defined and more accurate than known systems where the measured sample component is an extended source with a distribution of positions and various portions of the source can interfere with other portions of the source. Such a measurement technique described herein can be particularly advantageous for performing measurements with an accuracy better than the diffraction limit.

Referring to FIG. 1, a two-phase interferometric microscopy system 100 is used to determine position information in a third dimension (for example, the z direction) while simultaneously measuring position information in two other dimensions (for example, the x and y directions) at a sample S. The microscopy system 100 includes optical components 130 and 140, an interference system (which is also referred to as a multi-way beam splitter) 150, optical components 160 and 170, and detectors 165 and 175. The optical components 130 and 140 can be any type of optical component(s) that define an optical path 132 and 142, respectively, from the sample S to the beam splitter 150. For example, each of the optical components 130 and 140 can include a set of mirrors, lenses, or objectives. The optical components 130 and 140, for example, can include lenses or objectives that collimate optical energy emitted from the point source of the sample. Although FIG. 1 shows two diametrically opposite paths 132 and 142 into two optical components 130 and 140, in some implementations discussed below, a single optical component such as optical component 140 can encompass two non-opposing paths 132 and 142. The interference between the emission of the optical source (that is, the optical energy emitted at the sample S) in the first direction (that is, along the optical path 132) and the emission of the optical source in the second direction (that is, along the optical path 142) is caused at least in part by a difference in path length between the emission that travels along the first direction and the emission that travels along the second direction.

Optical components 130 and/or 140 can include additional components and/or features that allow the sample S to receive one or more sources of activation. For example, in some implementations, optical energy from optical sources (not shown in FIG. 1 but shown in FIG. 28, for example) can be used to activate the fluorescent response of the sample S to excitation photons. In such implementations, for example, the optical components 130 and/or 140 can include an aperture through which the optical energy from the optical sources can irradiate the sample S while minimizing stray radiation from the excitation laser traveling back towards the detectors 165 and/or 175. Laser line filters can also be in the beam path to the detectors 165 and/or 175 so that predominantly fluorescent light reaches the detectors. A first laser source can radiate the sample S, for example, with an activation beam and a second laser source can radiate the sample S, for example, with an excitation beam. In other implementations, an optical source other than a laser, such as a light-emitting diode, incandescent lamp, can be used as the source for activation and/or excitation. As described in further detail in the Betzig references incorporated by reference above, the activation beam is configured to activate sufficiently sparse subsets of individually resolvable photo-activatable labels in the sample, and the excitation beam is configured to excite the activated portions of the sample S to emit fluorescence-based photons.

In alternative implementations, the fluorescent response of the sample can be activated with one or more chemicals. In such alternative implementations, the sample can be exposed to a first chemical to activate the fluorescent sparse subsets of molecules of the sample and subsequently to a second chemical to deactivate the fluorescence of the sample if photobleaching is not used.

The beam splitter 150 can be any type of appropriate optical component that receives and combines the optical energy along optical paths 132 and 142, and sends the combined and mixed optical energy along two or more optical paths 152 and 154 (each also referred to herein as "a leg") to respective optical components 160 and 170. For example, the beam splitter 150 can be a 50:50 beam splitter in which the combined optical energy is split such that substantially 50 percent of the combined optical energy is sent on optical path 152 and substantially 50 percent of the combined optical energy is sent on optical path 154. As optical energy from the optical paths 132 and 142 is interfered and mixed by the beam splitter 150, the resulting optical energy along the optical path 152 is based on a relative phase difference between the optical energies from optical paths 132 and 142. Similarly, as optical energy along optical paths 132 and 142 is interfered and mixed in the beam splitter 150, the resulting optical energy along optical path 154 is based on a relative phase difference between the optical energies from optical paths 132 and 142, which is different from the relative phase difference associated with the optical energy along optical path 152. In this implementation, the resulting optical energy along optical path 152 and the optical energy along optical path 154 differ in phase by approximately 180 degrees.

Alternatively, the beam splitter 150 can divide the beam into any desired proportions such as, for example, 66:33 or 70:30. In other implementations, the beam splitter 150 can be a combination of multiple beam splitters. Such beam splitters can be constructed, for example, from a block of two glass segments and a thin film coating disposed between the two glass segments. Such beam splitters could produce three or more outputs, that is, more than the two of 152 and 154. This enables three or more output beams to be expressed with three or more interference phase angles (for example, 0 degrees, 120 degrees and 240 degrees), rather than 0 and 180 degrees in the two beam cases. In yet other implementations, in addition to or alternative to a beam splitter having a thin film coating, diffractive gratings can be used as beam splitters and can divide a beam into two or more beams. Gratings can also take multiple input beams and mix and interfere them into various output beams. In some implementations, the diffraction gratings can be used in conjunction with a sample having point sources emitting at the substantially same wavelength such as a label having a switchable scattering center (for example, a photoswitchable label with an activatable scattering characteristic). Such a sample having point sources emitting at substantially the same wavelength advantageously allows the diffraction gratings to deflect input beams at a relatively narrow deflection angle, which is a function of the wavelength of the input beam.

In another implementation, one or more of the beam splitters can include striped mirror portions instead of diffraction gratings or thin-film coatings. In one implementation, the striped mirror portions have a stripe period that is sufficiently small such that the diffractive order does not refocus into the image plane. For a wavelength λ, focal length f, and image size d, this means a period less than fλ/d. Other patterns could be used such as square or hexagonal polka dots. To prevent ghosting in the image, however, the same condition of the polka dot period (that is, less than fλ/d) must be maintained.

Similar to the optical components 130 and 140, the optical components 160 and 170 can be any type of optical component(s) that defines an optical path 152 and 154, respectively, from the beam splitter 150 to the detectors 165 and 175, respectively. For example, the optical components 160 and 170 can be lenses that de-collimate optical energy from optical paths 152 and 154, respectively, so that the optical energy is focused at the detectors 165 and 175, respectively. In some implementations, one or more of the optical components such as the optical components 130, 140, 160 and 170, and/or the beam splitter 150 can include adaptive optics.

In use, a statistically sparse subset of separately-imaged labels in the sample S is activated before a measurement is made. As mentioned above, the statistically sparse subset of the labels in the sample S can be activated by an appropriate technique such as by photo activation or chemical activation. Once activated, the sample S can be excited by an excitation source such as a laser, which causes photons to be emitted from the sample S along at least the optical paths 132 and 142 through the optical components 130 and 140 to the beam splitter 150. The optical energies from the optical paths 132 and 142 are combined at the beam splitter 150 and sent along the paths 152 and 154 through the optical components 160 and 170 to the detectors 165 and 175, respectively. A phase difference due to the path length difference between the beams 132 and 142 causes interference at the beam splitter 150 and modulates the intensity of the detected signals at the detectors 165 and 175. This modulated intensity can used to determine a position in the z coordinate, as described below in further detail. In addition, the detected signals at the detectors 165 and 175 provide position information in the x, y directions. After the detected signals are collected, the activated sparse subsets of the labels in the sample S can be bleached by repeated excitation so that no further optical signals can be detected from those labels, and further sparse subsets of labels can then be activated and excited for additional measurements, and the process repeated.

Figure 2:
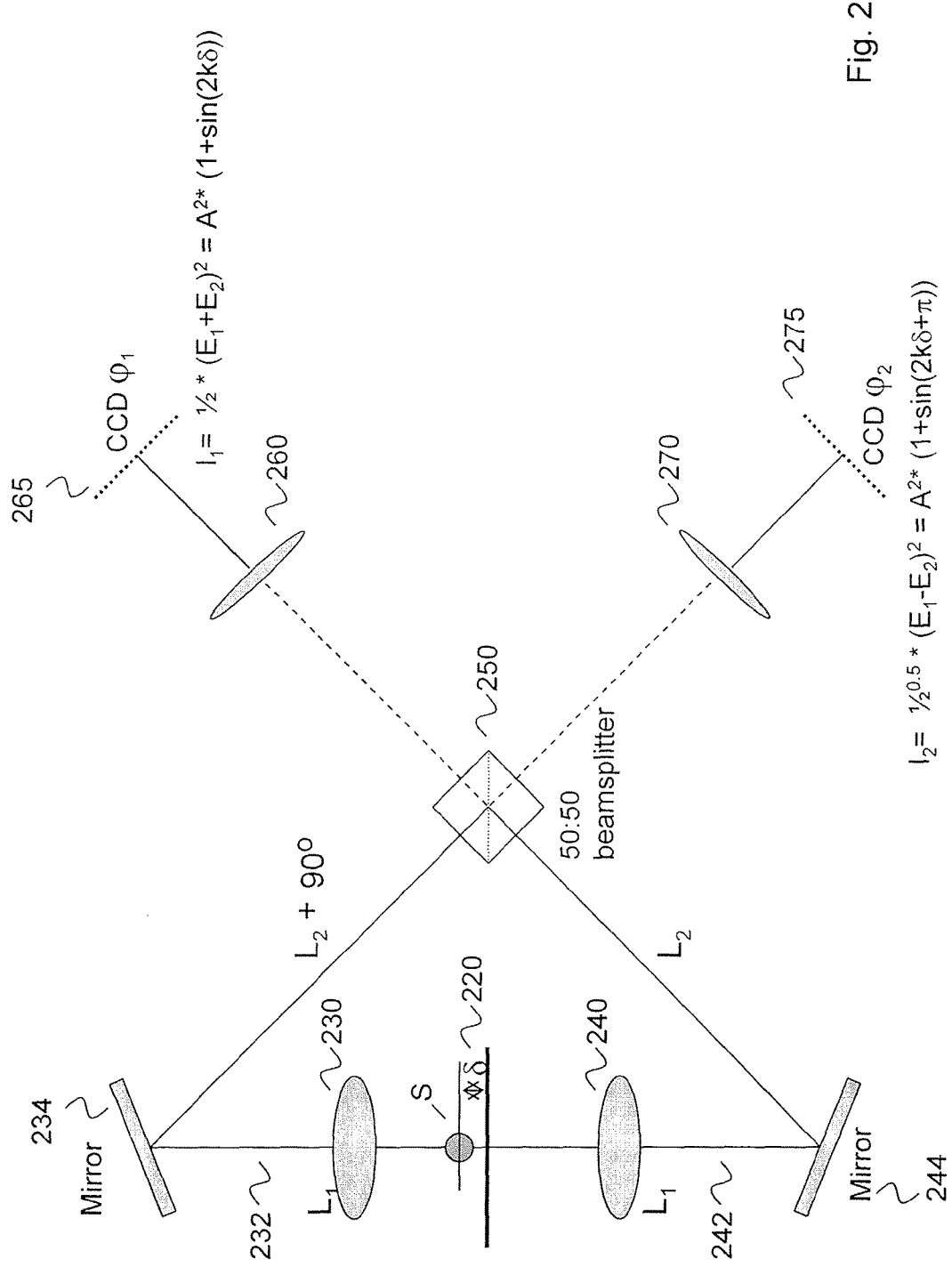
FIG. 2 is a block diagram of a two-phase interferometric microscope system and a single emitter sample.

FIG. 2 shows a system block diagram of a two-phase interferometric microscopy system and a sample with a single active emitter. As shown in FIG. 2, a single quantum emitter S is located a distance, δ, from a center location 220 along the z direction. The single quantum emitter S can be, for example, a fluorescent molecule, a quantum dot or a sub-wavelength scattering center. A radiated photon can escape from the quantum emitter S both upwards into lens 230 and downwards into the lens 240, where two collimated beams 232 and 242, respectively, are formed. The collimated beams 232 and 242 reflected by mirrors 234 and 244, respectively, and are received at the beam splitter 250.

Two beam paths are defined: a first beam path (also referred to as the top path) from the quantum emitter S to the mirror 234 and from the mirror 234 to beam splitter 250; and a second beam path (also referred to as the bottom path) from the quantum emitter S to the mirror 244 and from the mirror 244 to the beam splitter 250. The mirrors 234 and 244 and the beam splitter 250 are positioned relative to the quantum emitter S such that the lengths of the beam paths are matched to within about a wavelength $(L_1+L_2)_{top}=(L_1+L_2)_{bottom}$, with the exception of a positional displacement δ of the emitter along the z direction and a 90 degree phase shift on the top beam path, where $L_1$ is the path length between the center location 220 and the mirrors 234 or 244, and $L_2$ is the path length between the mirrors 234 or 244 and the beam splitter 250.

In this case the electric field of the optical beam in the top beam path is $E_1=A*\exp(-ik\delta+ikL_1+ikL_2+\pi/2)$, where $k=2\pi/\lambda$. The electric field of the optical beam in the bottom beam path is $E_2=A*\exp(ik\delta+ikL_1+ikL_2)$.

When received at the beam splitter 250, the optical beams are split, combined, and transmitted to the two detectors 265 and 275 through lenses 260 and 270, respectively. The electric field from one source of the optical beam going towards each detector 265 and 270 is $E_{12}=\frac{1}{2}^{0.5}*(E_1 \pm E_2)=\frac{1}{2}^{0.5}*(A*\exp(-ik\delta+ik \cdot L_1+ikL_2+\pi/2) \pm A*\exp(ik\delta+ikL_1+ikL_2))$.

Figure 3:
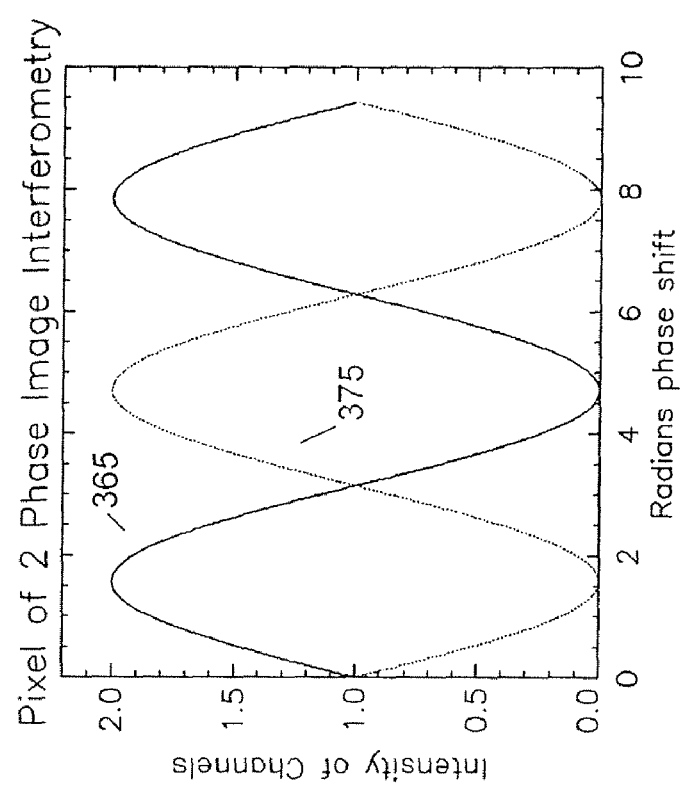
FIG. 3 is a graph of the intensities of the radiated light detected at the two detectors of FIG. 2.

In this implementation, each of the detectors 265 and 275 is a charged coupled device (CCD) detector or (for improved sensitivity to single fluorescent molecules) an electron-multiplying charged coupled detector (EMCCD). As shown in FIG. 3, the intensity 365 of the radiated light detected at detector 265 and the intensity 375 of the radiated light detected at detector 275 vary with a sine pattern with phase $4\pi\delta/\lambda$. More specifically, the intensity 365 of the radiated light detected at detector 265 is $I_1=\frac{1}{2}*(E_1+E_2)^2=A^2*(1+\sin(2k\delta))$. The intensity 275 of the radiated light detected at detector 275 is $I_2=\frac{1}{2}*(E_1-E_2)^2=A^2*(1+\sin(2k\delta+\pi))$. As can be seen from these two equations, the positional displacement δ leads to a source phase $2k\delta$ and the interference leads to an interference phase π. The z displacement δ can then be calculated by combining and inverting the two intensity equations: $(I_1-I_2)/(I_1+I_2)=\sin(4\pi\delta/\lambda)$ or $\delta=\lambda \arcsin((I_1-I_2)/(I_1+I_2))/4\pi$.

Figure 4:
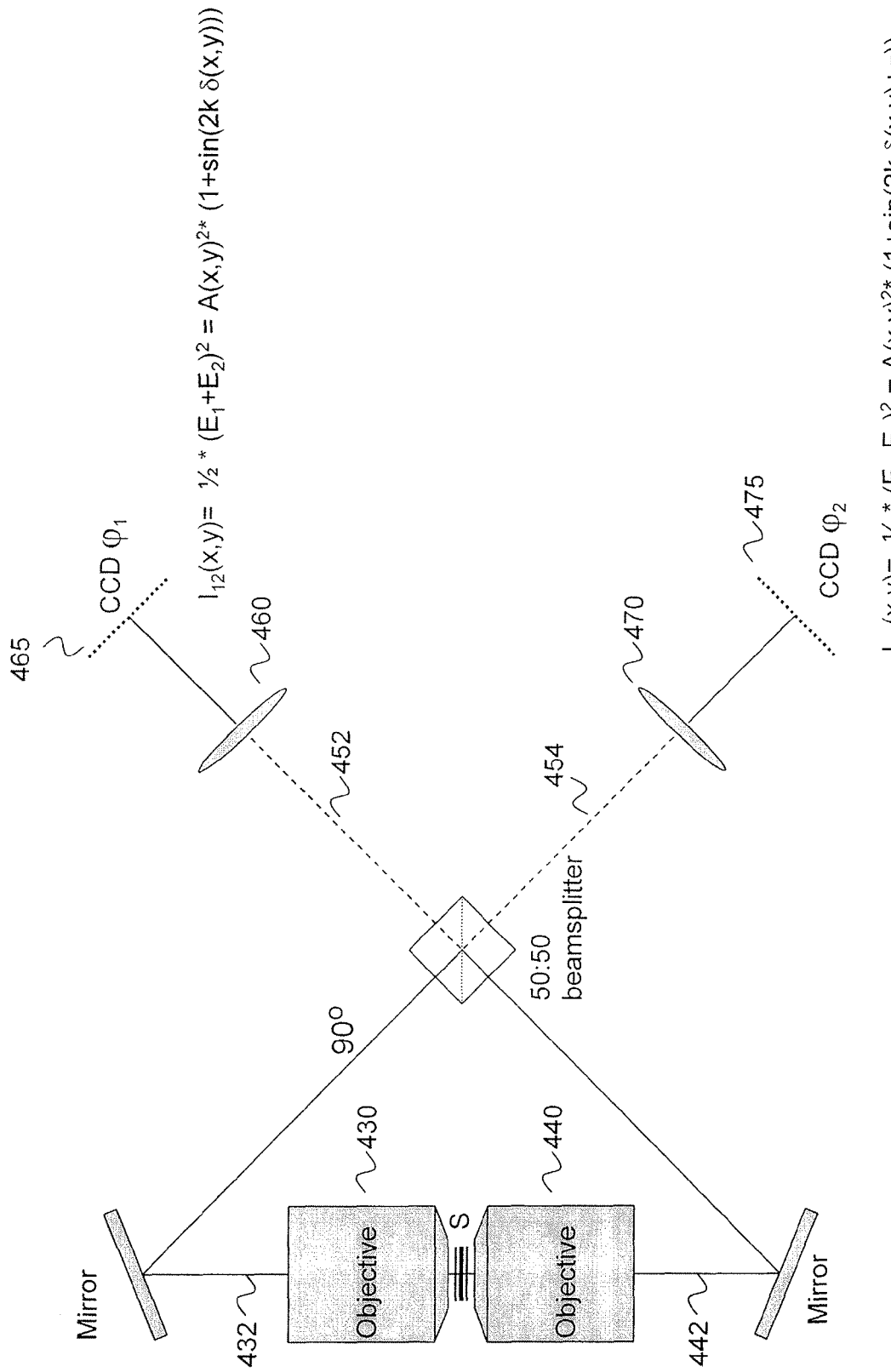
FIG. 4 is a block diagram of a two-phase interferometric microscope system and an extended sample.

This calculation can be generalized to a microscopy system such as that shown in FIG. 4. More specifically, FIG. 4 shows a system block diagram of a two-phase interferometric microscopy system and an extended sample. As shown in FIG. 4, the microscopy system includes microscope objectives 430 and 440 and lenses 460 and 470 such that an image plane is defined at detectors 465 and 475. Any point source at sample S will form a resolution limited spot on each image plane defined at detectors 465 and 475.

The intensity of the spatially integrated spot can then be used to calculate the z displacement (that is, the z coordinate position) of the point source of the sample S using an intensity equation described above. By using a CCD, EMCCD, or other large area detector, multiple image spots can be detected simultaneously and the z displacement δ of each associated portion of the sample 310 can be established at substantially the same time. The phase of the detected optical signals can be determined to a fraction of a radian so that positional information can be determined to better than a fraction (for example, <20%) of a wavelength. For example, for a wavelength of λ=600 nm, the positional information can be determined to less than 1 radian, which corresponds to δ=50 nm. Such an interferometric system can be configured such that the x,y locations of the source emitters can also be measured to the nanometer scale resolution.

Figure 5:
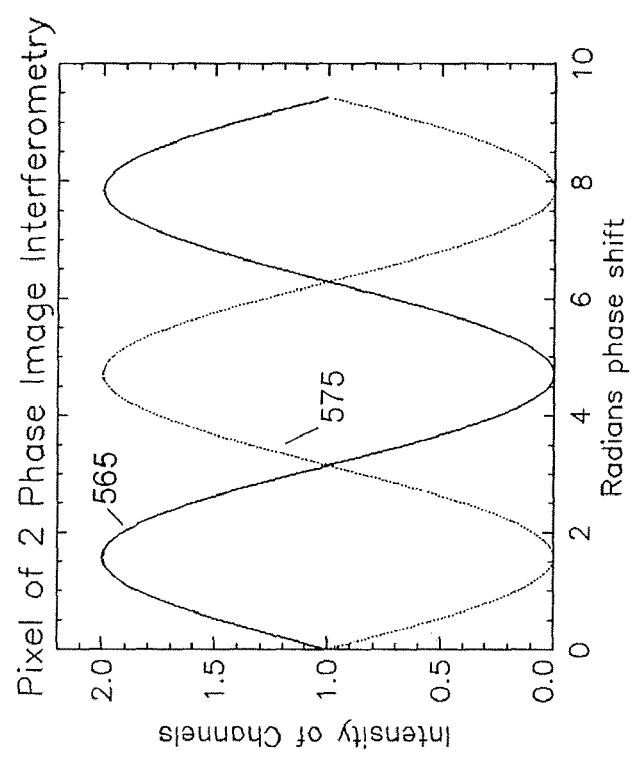
FIG. 5 is a graph of the intensities of the radiated light detected at the two detectors of FIG. 4.

The thickness of the sample S can affect the extent to which a unique z-coordinate position can be determined. For example, in the two-phase implementations shown in FIG. 2 or 4, if the thickness of the sample 210 is less than λ/4, then a unique z-coordinate position can be determined. The sensitivity to the z displacement, δ, for these implementations is non-uniform. In other words, if the phase is such that intensity is determined close to the minimum or maximum of the sine wave, then the slope approaches zero and therefore the sensitivity approaches to zero as shown in FIGS. 3 and 5. If, however, the phase is such that the intensity is determined away from the minimum or maximum of the sine wave, then the sensitivity to the z displacement, δ, for these implementations is measurable and nonzero.

Figure 6:
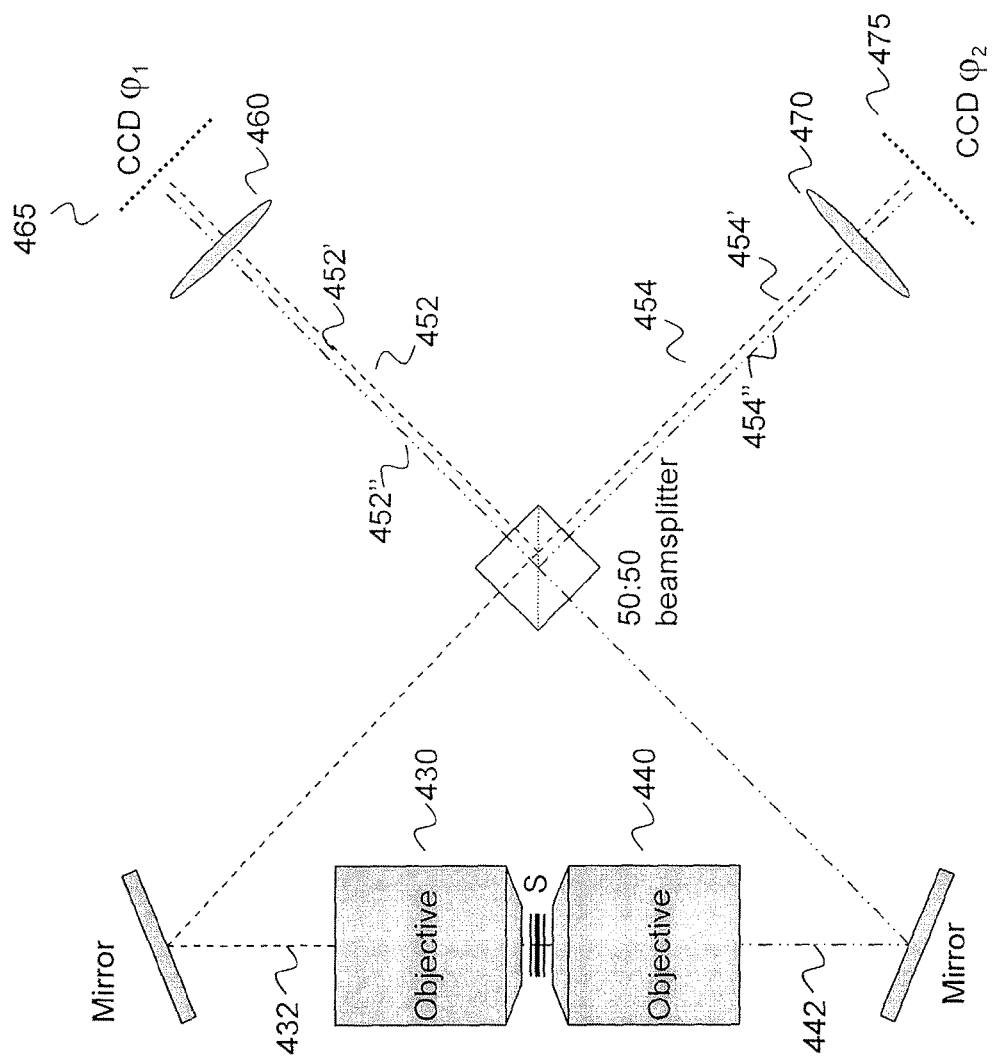
FIG. 6 is a block diagram of a two-phase interferometric microscope system with representations of beam phases.

FIG. 6 shows a system block diagram of a two-phase interferometric microscope system with representations of beam phases. In this two-phase interferometric microscope system, an interference phase of either 0 or π is imparted to the beam. Beam 432 has a phase different from the phase of beam 442 due to the displacement of the sample, and output beam 452 includes components 452' and 452" that differ in phase. Although beam components 452' and 452" are shown as being separated in FIG. 6, this is for illustration purposes and it should be understood that the beam components are coincidental and interfering with each other. Beam component 452' originates from beam 432 and beam component 452" originates from beam 442. Similarly, output beam 454 includes components 454' and 454" which differ in phase. Although beam components 454' and 454" are show as being separated in FIG. 6, this is for illustration purposes and it should be understood that the beam components are coincidental and interfering with each other. Beam component 454' originates from beam 432 and beam component 454" originates from beam 442. In this implementation, the phase difference (that includes both the source phase 2kδ and the interference phase 0) between beam components 452' and 452" determines an intensity $I_1$ that is detected at detector CCD $\phi_1$ and the phase difference (that includes both the source phase 2kδ and the interference phase π) between beam components 454' and 454" determines an intensity $I_2$ that is detected at detector CCD $\phi_2$.

FIGS. 7A and 7B each show a graph displaying the phase of the beam intensities of the components for a given output beam detected at a respective detector of FIG. 6. Output beams 452 and 454 in FIG. 6 include components of input beams 432 and 442. As shown in FIG. 7A, 452' and 452" are components of output beam 452 and are separated in phase by a phase difference 480 (which is the combination of the source phase 2kδ plus the interference phase 0). As shown in FIG. 7B, 454' and 454" are components of output beam 454 and are separated in phase by a phase difference 490 (which is the combination of the source phase 2kδ plus the interference phase π). The difference in these phase differences varies as a function of the position of the object. The squared sum of the beams represented in FIG. 7A produces a beam with the intensity $I_1$ shown in FIG. 7C, and likewise the squared sum of the beams represented in FIG. 7B produce a beam with the intensity $I_2$ shown in FIG. 7D. The relative intensity of these two beams, $I_1$ and $I_2$, determines the source phase and thereby the vertical displacement δ.

Figure 8:
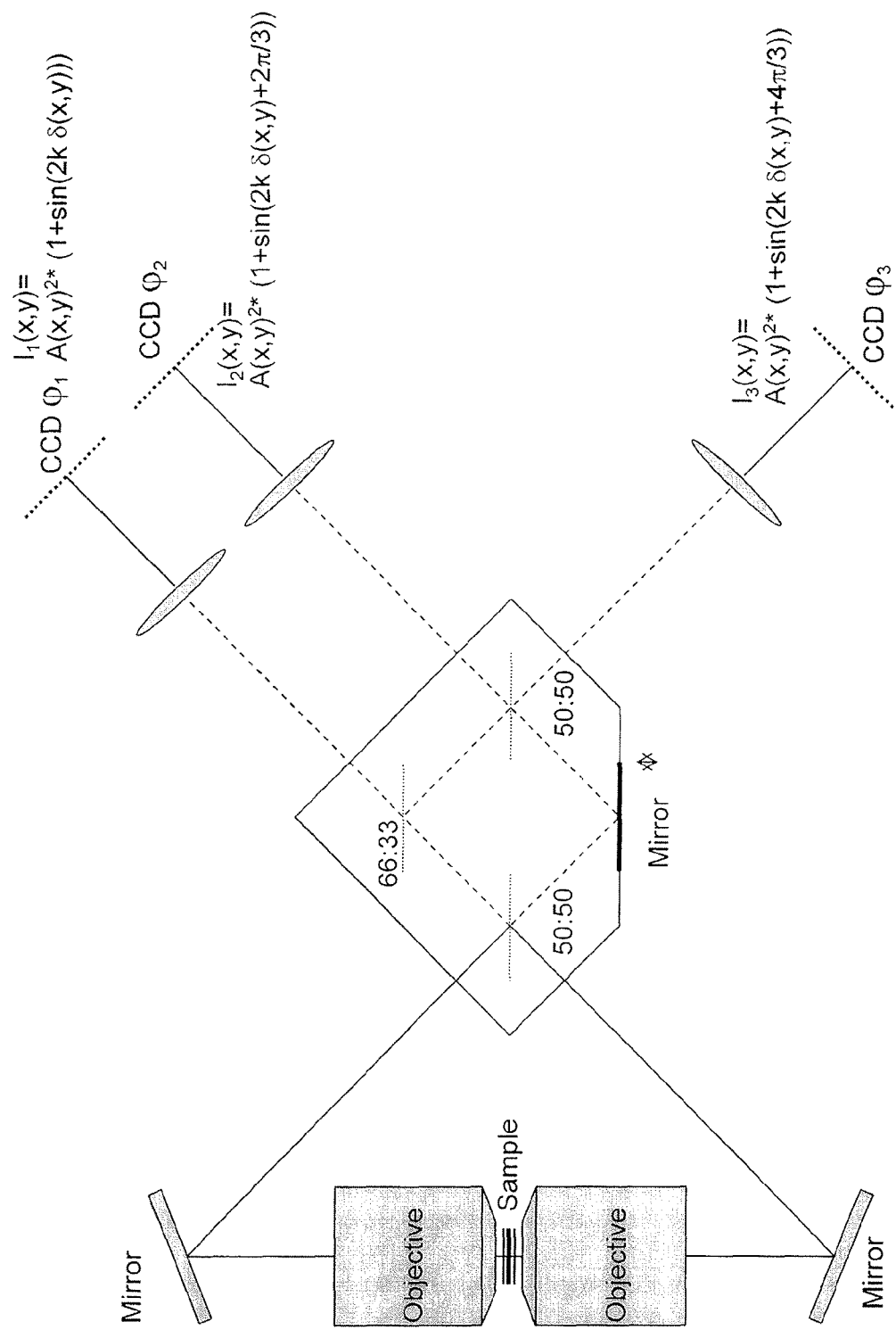
FIG. 8 is a block diagram of a three-phase interferometric microscope system.
Figure 9:
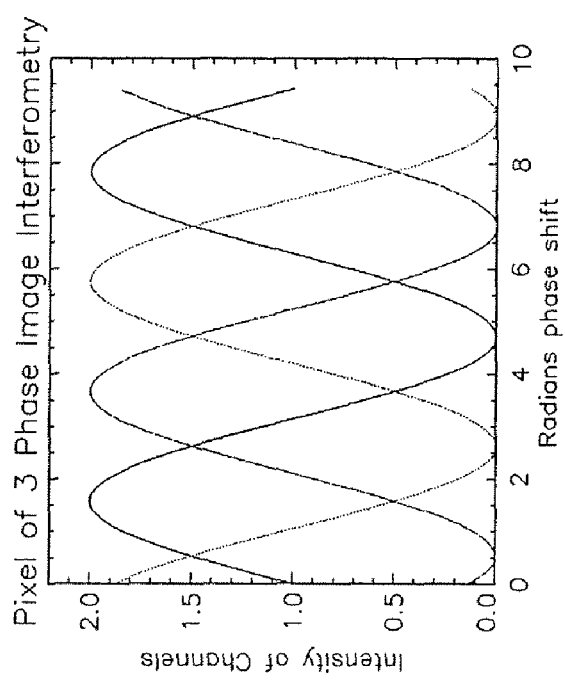
FIG. 9 is a graph of the intensities of the radiated light detected at the three detectors of FIG. 8.

In alternative implementations, the interferometric microscopy system can have more than two-phases. For example, FIG. 8 shows a system block diagram of a three-phase interferometric microscopy system. FIG. 9 shows a graph of the intensities of the radiated light from a point source when properly interfered and detected at the three detectors of FIG. 8.

Figure 10:
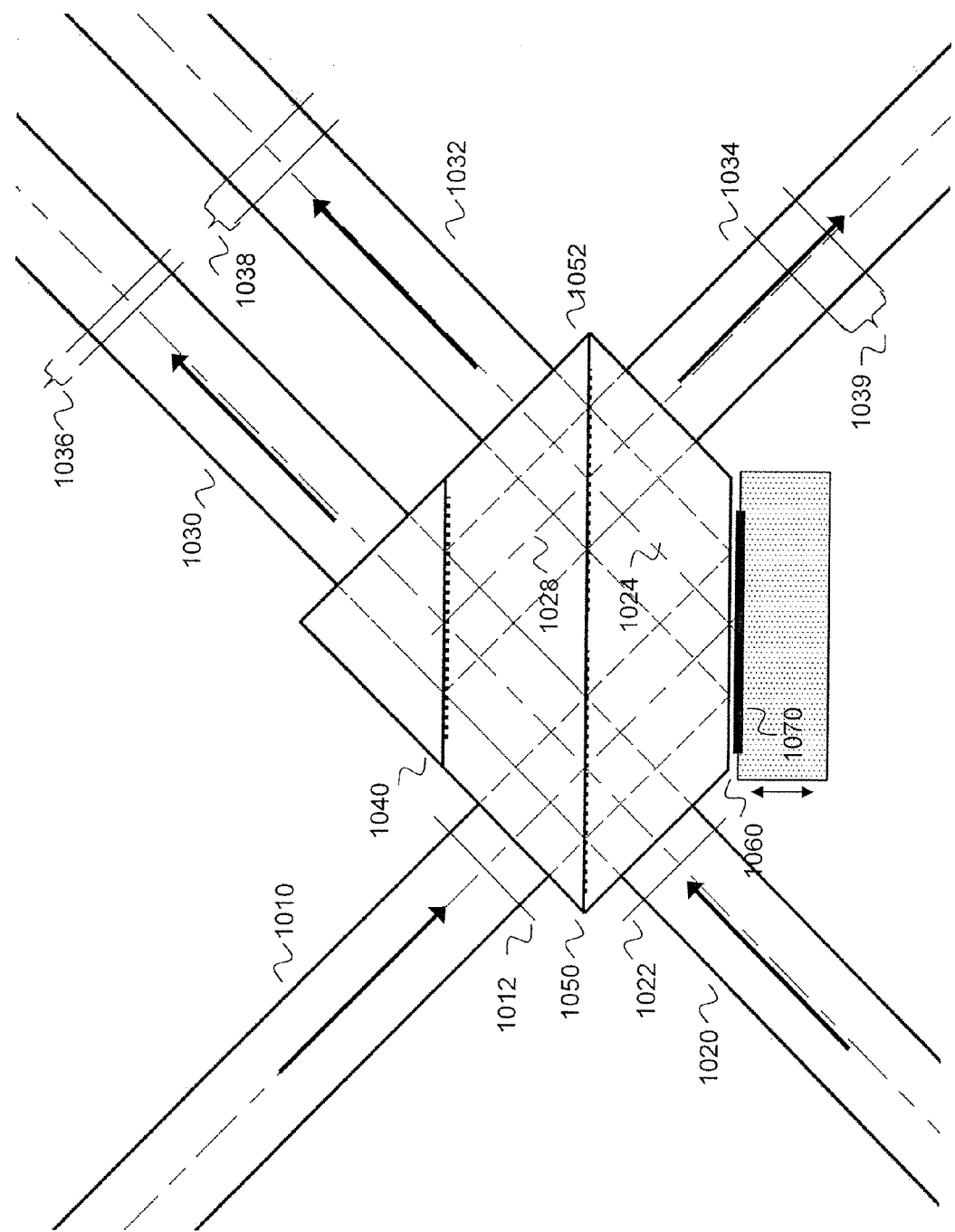
FIG. 10 is a diagram of a side view of a three-way beam splitter.
Figure 11:
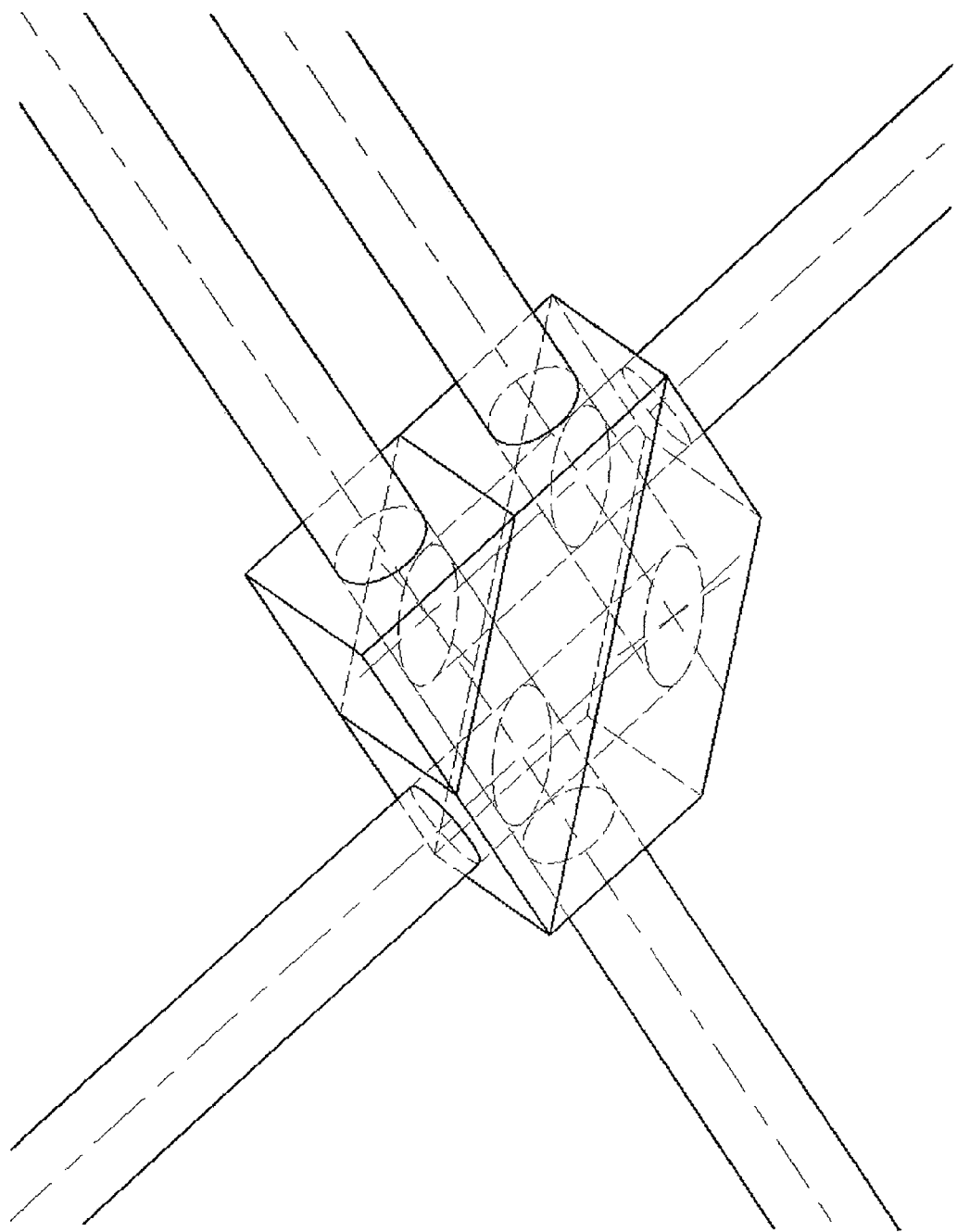
FIG. 11 is a perspective view of the three-way beam splitter of FIG. 10.

FIGS. 10 and 11 show an implementation of a three-way beam splitter. In this three-phase interferometric microscope system, an interference phase of either 0, 2π/3, or 4π/3 is imparted to the beam. The two emission beams 1010 and 1020 enter a 50-50 beam splitting surface 1050. The two resulting interfered beams proceed to an upper 66:33 beam splitting surface 1040 and a lower mirror surface 1070. Most of the upper beam, 66%, exits into output path 1030 and 33% goes to path 1028 and interferes with the beam 1024 that has been reflected from the mirrored surface 1070. This final interference takes place on a 50:50 beam splitting surface 1052 resulting in the second and third output beams 1032 and 1034. To have a balanced three-way interference (that is, similar amplitudes for output beams 1030, 1032 and 1034) between the three outputs, the interference phase of the interfering beams 1028 and 1024 can be tuned by changing the position of the mirror 1070 relative to the beam splitter and thereby change the size of the gap 1060. The gap 1060 can be filled with index matching oil to minimize residual reflectivity on the bottom of the glass prism.

Figure 10C:
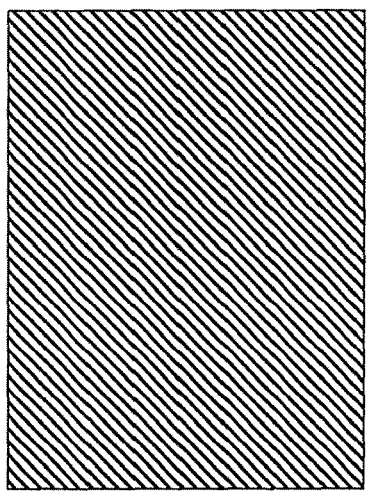
FIGS. 10A, 10B and 10C are diagrams of striped mirrors used as beam splitting devices in the three-way beam splitter of FIG. 10.
Figure 10B:
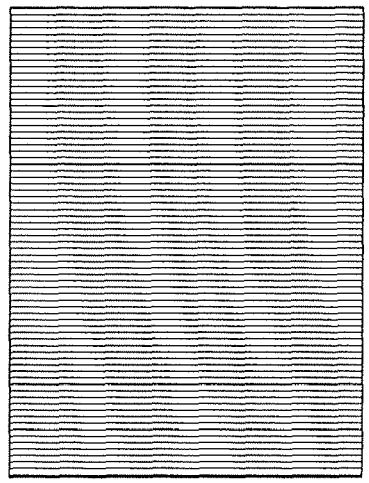
Figure 10A:
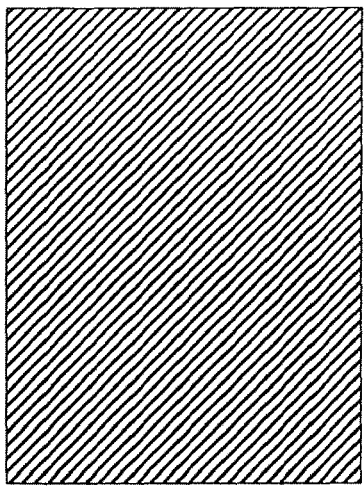

FIGS. 10A, 10B and 10C show striped mirrors used as beam splitting devices in the three-way beam splitter of FIG. 10. Each striped mirror shown in FIGS. 10A, 10B and 10C is rotated with respect to the other striped mirrors shown in FIGS. 10A, 10B and 10C to reduce undesirable interference in the beam paths.

FIGS. 10 and 11 further represent propagation of wavefronts associated with object and image planes through an implementation of a three-way beam splitter. Emission beams 1010 and 1020 having wavefronts 1012 and 1022 enter beam splitting surface 1050. Wavefronts 1012 and 1022 are associated with the object plane of the sample and are interfered with each other at beam splitting surface 1050. The resulting wavefronts interfere with each other at beam splitting surfaces 1040 and 1052, as they propagate through the three-way beam splitter. The beam splitting surfaces 1040, 1050 and 1052 have sufficient surface area to accommodate distortion and/or spreading of the wavefronts during interference at beam splitting surfaces 1040, 1050 and 1052. Output beams 1030, 1032 and 1034 emerge from the three-way beam splitter having combined the beams 1010 and 1020 with a relative phase shift of 1036, 1038 and 1039, with phase shift 1036 of 2kδ (source phase)+0 (interference phase), phase shift 1038 of 2kδ (source phase)+2π/3 (interference phase), and phase shift 1039 of 2kδ (source phase)+4π/3 (interference phase). This results in different intensities of beams 1030, 1032 and 103, which are intact, interfered versions of the wavefronts 1012 and 1022 and propagate to the image planes of the detectors.

Figure 12:
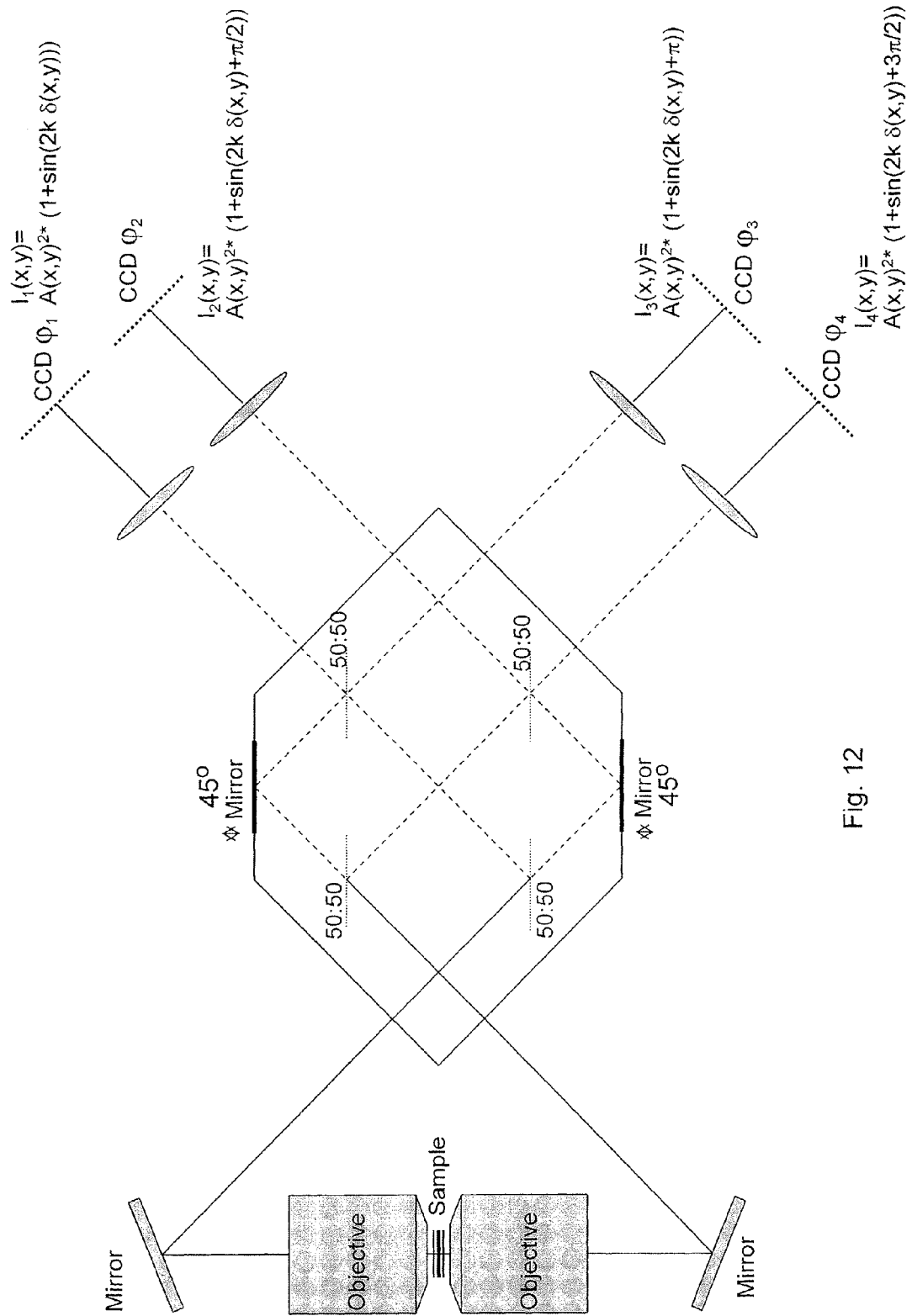
FIG. 12 is a block diagram of a four-phase interferometric microscope system.
Figure 13:
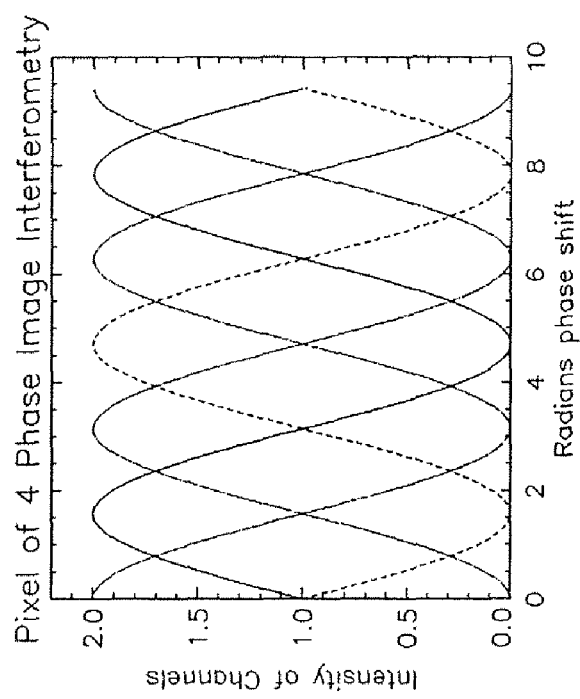
FIG. 13 is a graph of the intensities of the radiated light detected at the four detectors of FIG. 12.

FIG. 12 shows a system block diagram of a four-phase interferometric microscopy system. FIG. 13 shows a graph of the intensities of the radiated light detected at the four detectors of FIG. 12. Although FIGS. 8 through 12 show implementations having three- or four-phase interferometric microscopy systems, systems having more than four phases are possible such as five-phase interferometric microscopy systems, six-phase interferometric microscopy systems, etc.

Figure 8A:
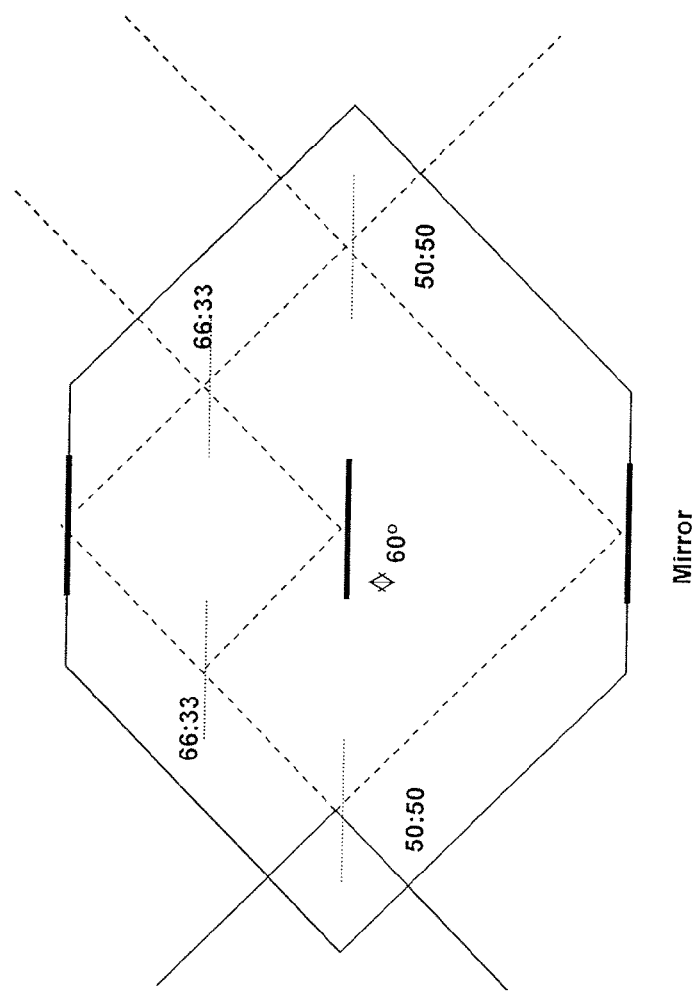
FIG. 8A is a diagram of a side view of a three-way beam splitter.

While a two-phase interferometric microscopy system can use, for example, a beam splitter such as the 50:50 beam splitter 250 as shown FIG. 2, the beam splitter for microscopy systems having more than two phases (for example, as shown in FIG. 8) can be implemented in several different ways. For example, as shown in FIG. 8, the beam splitter can include multiple components: two 50:50 beam splitters, a 66:33 beam splitter, and a mirror. These beam splitter components can be positioned manually, for example, on an optical bench. Alternatively, these beam splitter components can be manufactured and disposed between a pair of optical flats; the position of such beam splitter components can be adjusted, for example, by piezoelectric transducers. Such adjustments can insure that the phase shifts of the three legs are spaced by 2π/3 or for a N leg implementation by 2π/N and also parallelness of the splitting planes is established. An alternative implementation of a three-way beam splitter is shown in FIG. 8A.

Figure 8B:
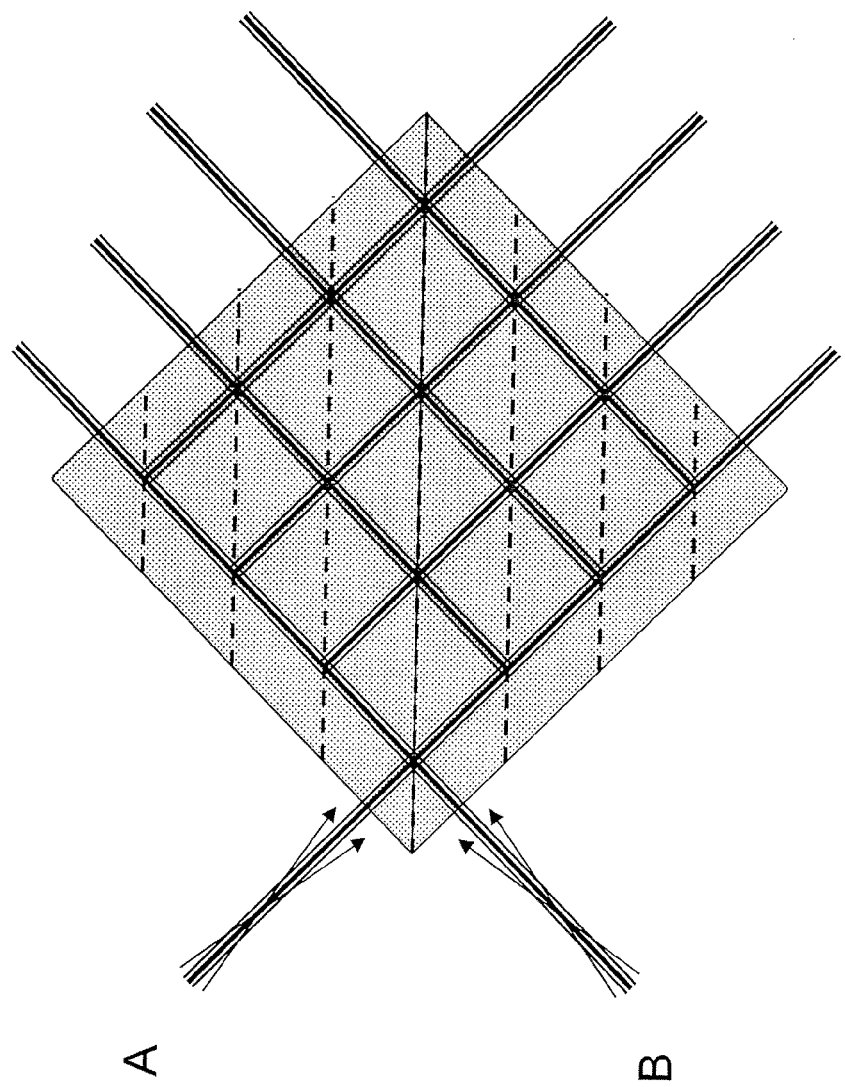
FIG. 8B is a diagram of a side view of an eight-way beam splitter.

FIG. 8B shows a system block diagram of an eight-way beam splitter. As shown in FIG. 8B, the beam splitter includes multiple beam splitter components each of which is represented by a dashed line. Although FIG. 8B explicitly shows a beam splitter with 16 beam splitter components that produces eight output beams, it should be understood that the basic structure can be followed for a greater or lesser number of beam splitter components to produce N number of output beams. These beam splitter components can have a reflectivity that ranges between 0 to 100%. Transmission can be nominal. When the surfaces of the beam splitter components are substantially parallel to each other, substantially the whole extent of a beam (or beam portion) (having a diameter, D) can interfere coherently with reflected beam portions of or other beam portions split from the original input beams A and B. The surfaces of the beam splitter components can be substantially parallel, for example, with each being within an angle of $<\lambda/D$. Also the beam splitter components are equally spaced to within a coherence length $\lambda^2/(n\Delta\lambda)$ of the input beams, where $\lambda$ is wavelength, $\Delta\lambda$ is a range of wavelengths, and n is the index of refraction of the medium. This spacing insures that the interference is substantially coherent across the beam wavelength range d1 of interest. Input beams A and B enter the beam splitter with a direction vector so that A-B is a vector normal to the planes of the beam splitter. Both input beams are aimed to the same point on the first beam splitter component. The parallel planar structure of the beam splitter allows a range of beams angles to self interfere; this range of beam angles can correspond to the range of angles associated with an image in a collimated portion of a beam before it is focused onto an image plane of, for example say a CCD detector (not shown in FIG. 8B). In some implementations, both the reflectivity of each beam splitter component and the fine spacing between beam splitter components (less than the coherence length but enough to control interference angle) can be varied to ensure a substantially equal splitting into the N output beams (FIG. 8B shows N=8) for the case where only one input beam (for example, input beam A or input beam B) is applied. Furthermore, in some implementations, the interference angle between the input beam A and the input beam B can be set to different intervals of 360 degrees/N. So, in the example shown in FIG. 8B where N=8, the intervals of 45 degrees, 90 degrees, 135.degrees can be established.

Figure 14:
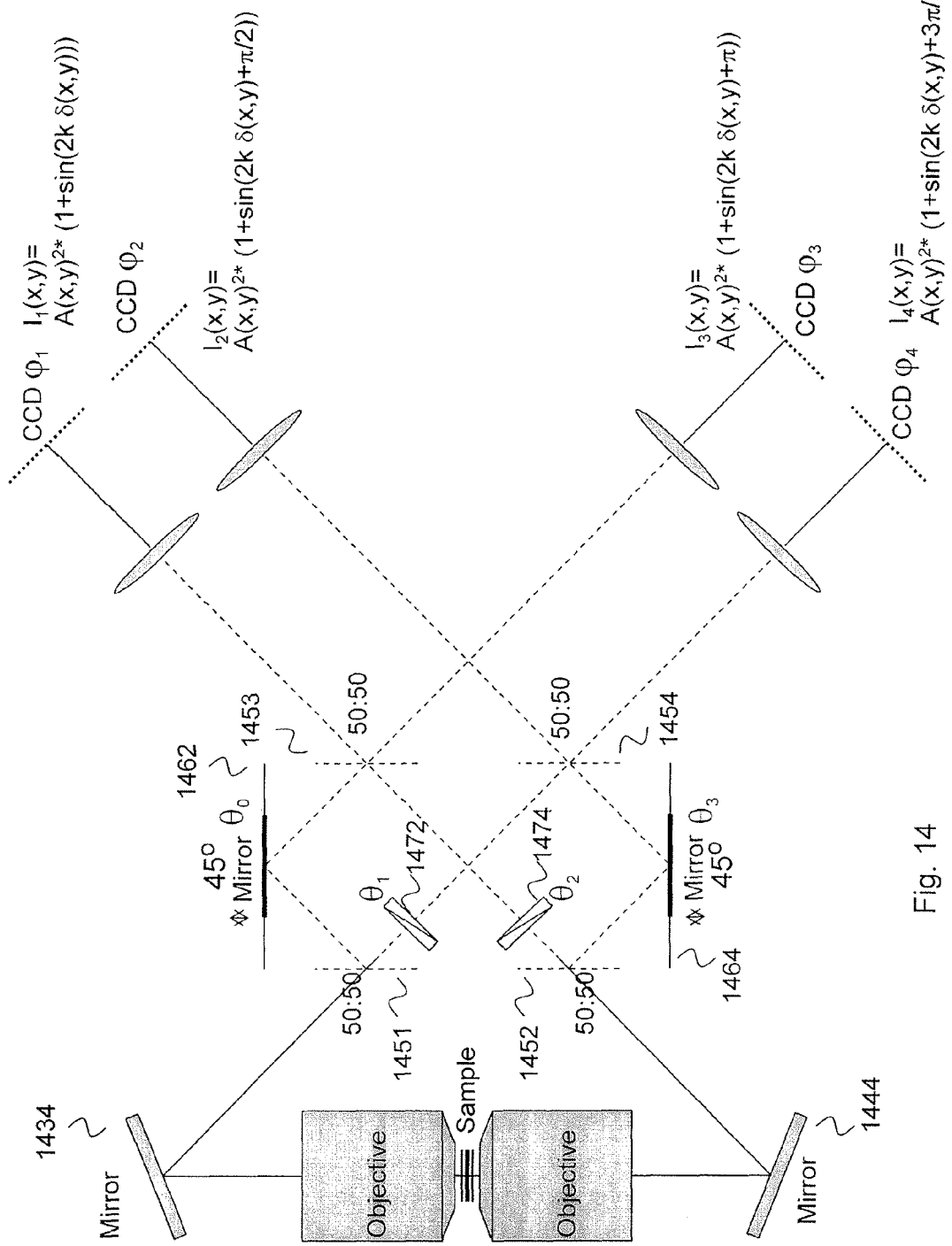
FIG. 14 is a block diagram of a four-phase interferometric microscope system having diffractive gratings.
Figure 15:
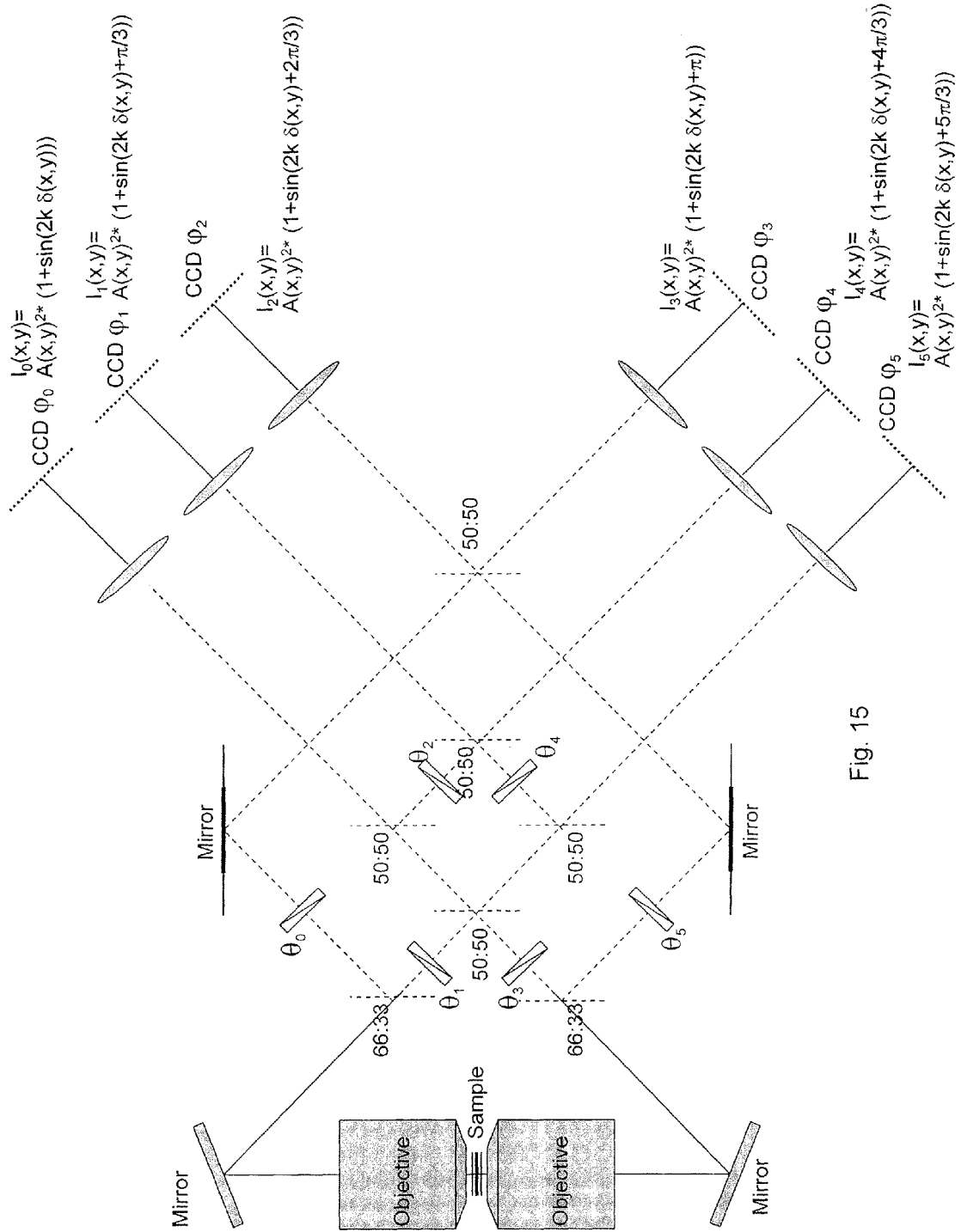
FIG. 15 is a block diagram of a six-phase interferometric microscope system having diffractive gratings.

As mentioned above, in some implementations, one or more beam splitters can be based on diffraction gratings instead of beam splitters having thin-film coatings. For example, FIG. 14 shows a system block diagram of a four-phase interferometric microscope system having diffractive gratings. In this implementation, the beam splitter 1450 includes diffraction gratings 1451 through 1454, mirrors 1462 and 1464, and phase shifters 1472 and 1474. Diffraction gratings 1451 and 1452 receive optical energy from mirrors 1434 and 1444, respectively. Diffraction grating 1451 divides the received optical energy and sends the divided portions to mirror 1462 and phase shifter 1472. Diffraction grating 1452 divides the received optical energy and sends the divided portions it to mirror 1464 and phase shifter 1472. Diffraction grating 1453 receives and mixes the optical energy from mirror 1462 and phase shifter 1474, divides the mixed optical energy, and sends each of the divided portions to a different detector. Similarly, diffraction grating 1454 receives and mixes the optical energy from mirror 1464 and phase shifter 1472, divides the mixed optical energy, and sends each of the divided portions to a different detector. FIG. 15 shows a system block diagram of a six-phase interferometric microscope system having diffractive gratings.

In some implementations, spectral filters (for example, bandwidth filters, low-pass filters or high-pass filters) can be disposed in the optical paths to reduce or prevent particular optical energies from contributing to the optical energy emitted from the switchable optical source. For example, optical energy used during photo-activation and/or photo-excitation can be removed from the optical paths to decrease stray light and noise within the optical paths and propagating towards the detectors.

In some implementations, one or more of the sample, objectives, mirrors, optical components, beam splitters, lenses, spectral filters and other elements along the optical paths can be coupled individually to multi-axis positioners including, for example, piezoelectric actuators. Such multi-axis positioners can allow for automated or non-automated calibration and positioning. Additionally, such multi-axis positioners can improve precision and accuracy in positioning and calibration over manual methods.

During setup and as a guide to positioning and alignment of the interferometer system, it can be useful to have a shutter incorporated into the two input beam paths. This allows one to observe the image from each path independently, and make sure that each path is optimally focused. Furthermore, because the images of the two portions can be observed, it is possible to shift one image with respect to the other so that they overlayed for optimal interference when the shutters are open for both beams.

In alternative implementations having more than two-phases, the sensitivity can be phase invariant. In addition, the unique range of operation can be extended to $\lambda/2$. Larger displacements will result in a positional ambiguity modulo $\lambda/2$. This can be lifted with supplemental techniques, such as, for example, selective illumination (excitation or activation) in both space and time domain, or sample sectioning. In such implementations, for example, having three-phase or four-phase interferometry, the position of the measured portion of the sample is determined by the intensities: $I_{ij}=G_j*(A_{Ui}^2+A_{Li}^2+2*\beta_j*A_{Ui}*A_{Li}*\cos((\phi_i+\phi_j)+Ofs_j)$, where $j=0, 1, 2, \ldots$ indicates the leg of multiphase interferometer; $I_j$=intensity of the j leg of point source, with offset no correction; j=interference correction factor of $j^{th}$ leg; $G_j$=gain of the $j^{th}$ leg; $Ofs_j$=offset of the $j^{th}$ leg; $A_{Ui}$=Amplitude of $i^{th}$ point source upper objective; $A_{Li}$=Amplitude of $i^{th}$ point source lower objective; $\phi_j=j^{th}$ leg phase shift (this is the interference phase); and $\phi_i$=point source (that is, fluorescent molecule) phase due to the path length difference.

Dark calibration (in which $A_{Ui}=A_{Li}=0$) allows one to determine the dark signal from the $j^{th}$ detector $I_{oj}=G_j*Ofs_j$, $I_{ij}=G_j*(A_{Ui}^2+A_{Li}^2+2*\beta_j*A_{Ui}*A_{Li}*\cos(\phi_i+\phi_j)+Ofs_j)$. The total amplitude is $A_{Ti}^2=A_{Ui}^2+A_{Li}^2$. The rescaled interfering fraction is $X_i=2*A_{Ui}*A_{Li}/A_{Ti}^2$. So, with these variables, the intensities are: $I_{ij}=I_{oj}+G_j*A_{Ti}^2(1+\beta_j*X_i*\cos(\phi_i+\phi_j))$.

A calibration in which a fiducial source is moved by $\delta$ along the z direction can be used to determine the remaining apparatus parameters $G_j$, $\beta_j$ and $\phi_j$. This results in an intensity signal that oscillates in each leg similarly to FIG. 7 for the three phase case as the phase $\phi_i(z) \sim 4*n/(n\lambda)\delta(z)$ winds. Here, n is the index of media with the shifted path length (for example, immersion oil).

A fit to a set of such calibration data determines the following equation for each leg j on a reference fiducial with interference fraction of the emitting fiducial $X_f$ and its intensity $A_{Ti}^2=I_f$ where the apparatus parameters $G_j$, $\beta_j$, and $\phi_j$ are now determined. Such calibration can be useful if the phase-shift values are not exactly 120 degrees (for three legs) or $2\pi/N$ (for N legs).

$$I_{ij}(z)=I_{oj}+G_j*I_f(1+\beta_j*X_f*\cos(\phi_i(z)+\phi_j)).$$

$G_j$, $\beta_j$ can be defined by normalizing to fiducial units: $I_f=1$ and $X_f=1$ and $\alpha_i=A_{Ti}^2/I_f$ $$I_{ij}=I_{oj}+G_j*A_{Ti}^2(1+\beta_j*X_i*\cos(\phi_i+\phi_j)).$$

$$D_{ij}=(I_{ij}-I_{oj})/(G_j*I_f) \text{ rescaled intensity data.}$$

$$D_{ij}=\alpha_i*(1+\beta_j*X_i*\cos(\phi_i+\phi_j)).$$

Figure 26:
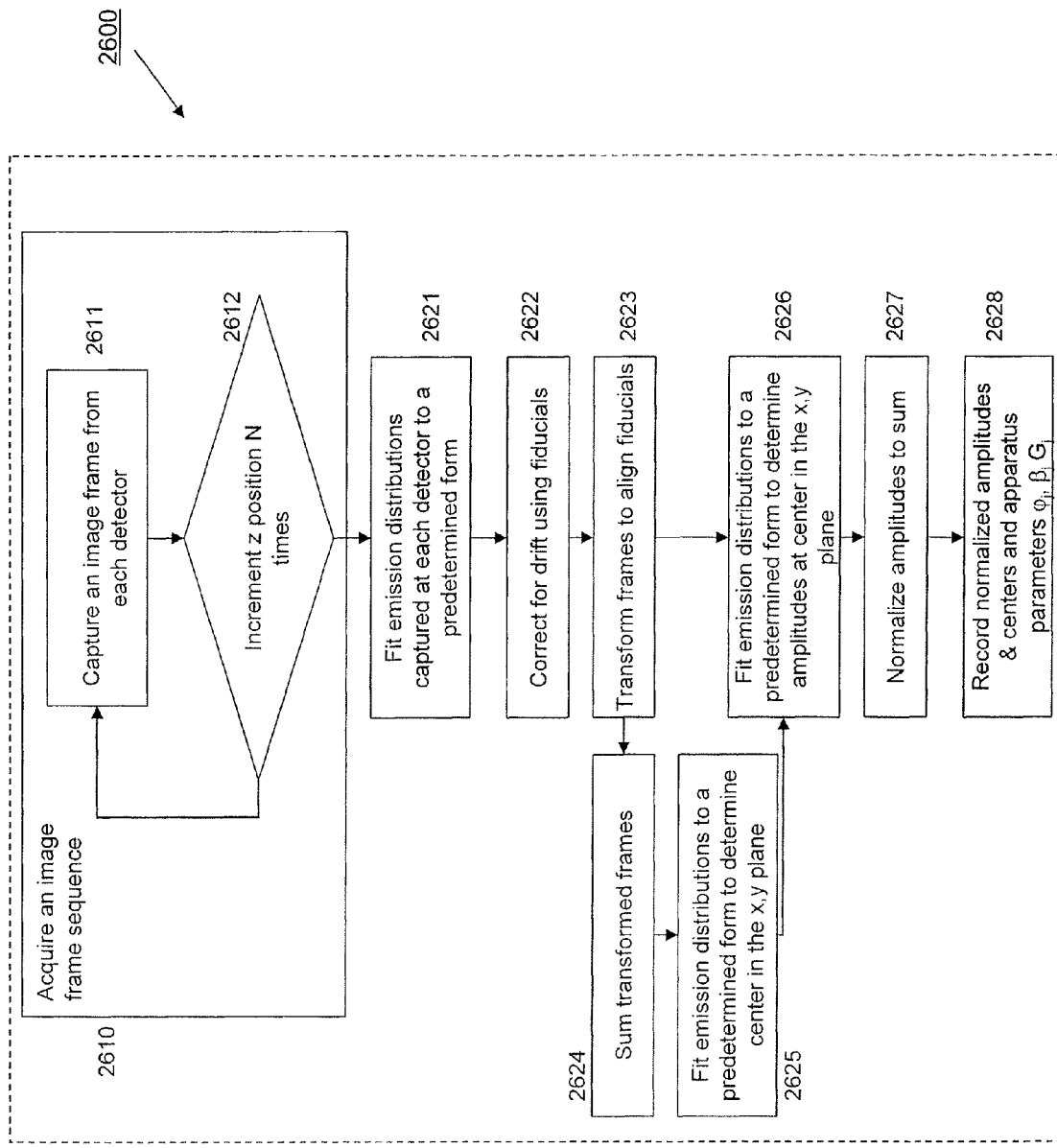
FIG. 26 is a flowchart of a calibration process for a multi-phase interferometric microscope system.

FIG. 26 shows a flowchart of a calibration process 2600 for a multi-phase interferometric microscope system using an automated calibration method. At 2610, an optical emitter including sub-diffractive fiducials is imaged at various positions in the z direction to produce an image frame sequence. This process at 2610 includes sub-processes 2611 and 2612, which are repeatedly performed for various positions in the z direction to produce the image frame sequence. At 2611, an image of the optical emitter is captured at each detector in the interferometric microscope system. The image frames captured at each detector contain phase-related characteristics (for example, $\phi_j$ $\beta_j$ of the $j^{th}$ detectors) that are phase-shifted relative to the information in the image frames captured at the other detectors. The z position of the optical emitter is incremented at 2612 and 2611 is repeated N times to produce an image frame sequence. Each image frame in an image frame sequence is based optical energy intensities in the x,y plane relating to the emission distribution of the optical emitter.

At 2621, the emission distributions of the optical emitter are fit to a predetermined distribution to localize the optical emitter emission distribution in the x,y plane. For example, certain optical emitters have emission distributions that can be accurately fit to Gaussian distributions. Such Gaussian distributions can represent, for example, a likelihood a point spread function of the images of optical emitters. At 2622, the image frames are corrected for drift using the fiducials included in the image frames. The drift-corrected frames are then transformed at 2623 to produce transformed frame that align the fiducials in the image frames in the x,y plane.

At 2624, the image frames captured at each of the image detectors for each position in the z direction are summed into summed image frames. The summed image frames are a composite of the phase-shifted image frames captured by each detector. At 2625, the summed image frames are fit to a predetermined distribution to determine the center of the optical emitter in the x,y plane.

The transformed frames are fit at 2626 to a predetermined distribution, such as a Gaussian distribution, and the amplitude of the optical emitter emission distribution in each frame is measured at the center of the optical emitter in the x,y plane determined in 2625. The center of the optical emitter can be based on, for example, the centroid of a Gaussian distribution (for example, a three-dimensional distribution) representing a likelihood of the location of an optical emitter. At 2627, the amplitudes of the optical emitter emission distribution are normalized to the sum determined at 2624. The normalized amplitudes determined at 2627 for each image and the associated z position is recorded at 2628. For example, the normalized amplitudes and the associated z positions for each frame can be stored within a look-up table or parameterized by the previous equations to determine $\phi_j$ and $\beta_j$.

The following equations set forth an explanation by which the z displacement, $\delta$, of the optical source (that is, the relative z-coordinate position of the sample) can be determined from the intensity data collected by the interferometry microscopy system.

Once the calibration is complete, the data can be scaled and then the values $\beta_j$ and $\phi_j$ are also known for each output beam of the interferometer. The j equations: $D_{ij}=\alpha_i*(1+\beta_j*X_i*\cos(\phi_i(z)+\phi_j))$ can be used to determine the position of an emitter along the axial direction. Thus three or more data values $D_{i0}$, $D_{i1}$, $D_{i2}$, ... for the intensity of the $i^{th}$ molecule result in three or more equations to determine the three unknown values: $\alpha_i$, $X_i$, and (of most interest) $\phi_i(z)$. If there are only three phases, then the three equations will yield a unique solution for these three unknowns. This and the value of $\phi_i$ in particular can be solved for example by Newton's Method.

If there are more than three phases, then four or more equations can determine the three unknown values and the system of equations is over constrained. In that case, the best values for the unknowns can be determined using a chi-squared minimization method. By minimizing the error of the equations: $\chi_i=\Sigma_j[D_{ij}-\alpha_i(1+\beta_j\cos(\phi_i+\phi_j))]^2$.

In the approximation of a well balanced interferometer system (meaning phase shift increment between cameras and equalized gain and equalized interference efficiency) we can obtain a best value for $\phi_i$ given by the equation: $\tan(\phi_i)\cong-\Sigma_j D_{ij} \sin(\phi_j)/\Sigma_j D_{ij} \cos(\phi_j)$.

Once the phase $\phi_i$ of the $i^{th}$ emitter is known then the vertical position (the z displacement) $\delta$, along the z axis can be deduced to a first approximation by the equation. Note that n is the index of refraction of the sample environment. $\delta_i \cong \lambda*\phi_i/(4\pi n)=\lambda/(4\pi n)*\text{atan}(\Sigma_j D_{ij}\sin(\phi_j)/\Sigma_j D_{ij}\cos(\phi_j))$.

This last equation solving for displacement, $\delta$, describes the phase shift determined from the intensity data. In other words, this last equation shows how the displacement, $\delta$, can be calculated based on the intensity data detected at the detector for each leg of the interferometry microscope system. For example, for a three-phase interferometry microscope system $(\phi_j)\cong-2\pi/3, 0, 2\pi/3$. For a four-phase interferometry microscope, $(\phi_j)\cong 0, \pi/2, \pi, 3\pi/2$.

Note that the above equation for calculating displacement, $\delta$, is based on various assumptions. In alternative implementations, other assumptions can be used resulting in one or more alternatives for calculating the displacement, $\delta$. For example, higher order corrections can be calculated from the real part and taking out the approximations that the N phases of each interferometer leg are equally spaced or that the sensitivity of interferometer leg is equal. Alternative implementations can include further refinements that provide a means to calibrate and correct for non-balanced intensity sensitivities and phase mixing angles.

In summary, the N spot intensities of an N phase interferometer become the data $D_j$ that can be converted to the vertical position displacement $\delta$.

Because $\phi_i$ is a cyclic solution, for every $2n$, the uniquely determinable range extends $\lambda/2n$. For samples thicker than this, an ambiguity exists in determining $\delta$ by $\pm N \lambda/2n$ for an integer N. Other attributes, such as measured point spread function and interference efficiency, can be used to find the most likely N and chose the best of a multi-valued solution. In effect the extent of defocus is an alternate, less precise but adequate method to estimate to within $\lambda/2n$ where the emitter is located. This combined with the interferometricly-deduced position can give a unique vertical position of the emitter. One further consideration in estimating the vertical position is to account for the Gouy phase, an extra term that advances the phase by an extra it at the focus over about a Rayleigh length distance $z_R$. In this case $\delta$ is given by the solving the following equation: $\phi_i \cong 4\pi\delta/(n\lambda)+\text{atan}(\delta/z_R)$.

Figure 27:
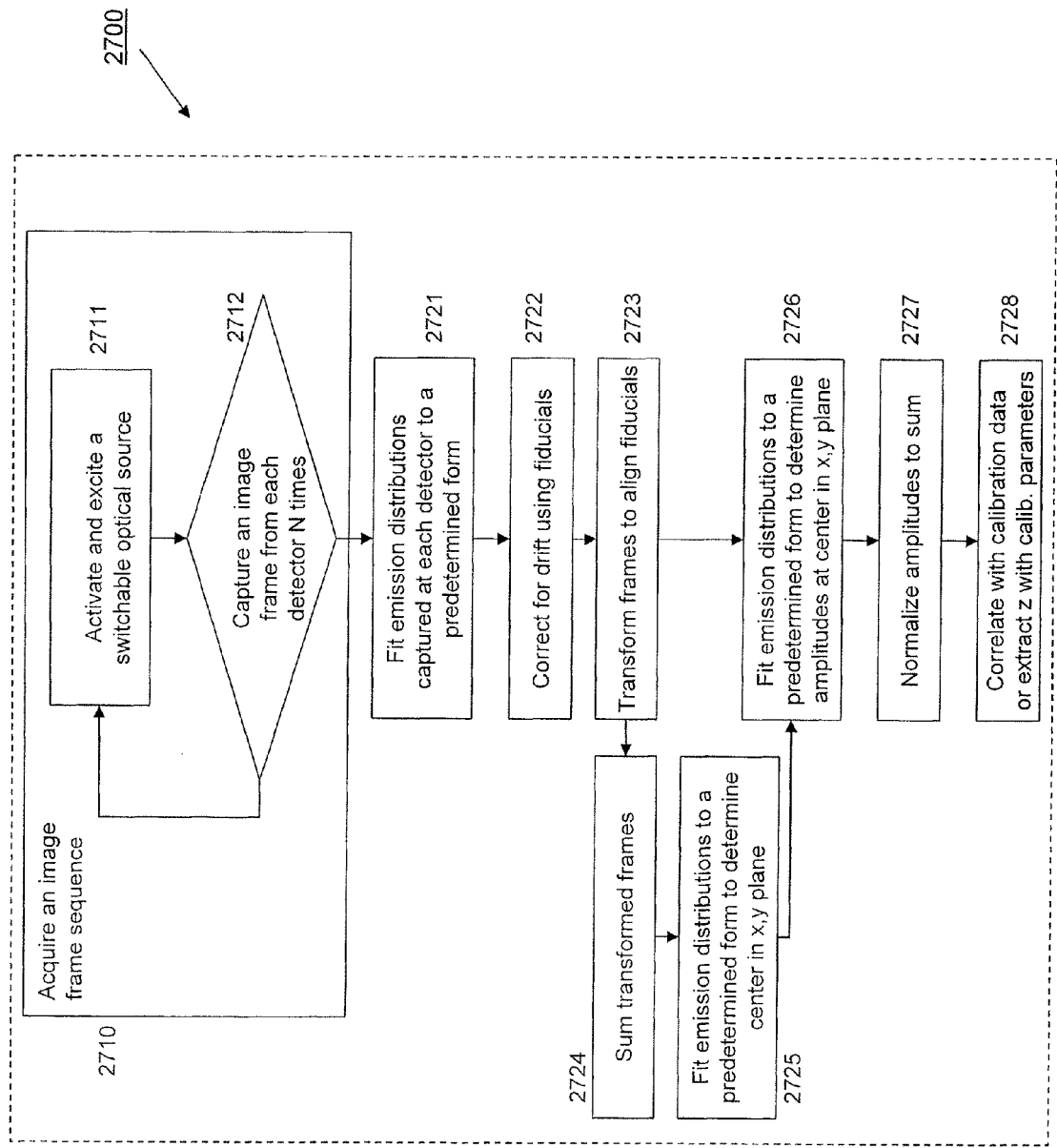
FIG. 27 is a flowchart of a process for obtaining 3-dimensional position information of photo-activated samples within a multi-phase interferometric microscope system.

FIG. 27 shows a flow chart of a process for obtaining three-dimensional position information of photo-activated samples within a multi-phase interferometric microscope system. At step 2710, various switchable optical sources including sub-diffractive fiducials are imaged to produce an image frame sequence. Step 2710 includes sub-steps 2711 and 2712, which are repeatedly performed to activate and excite different sparse subsets of the fluorescent labels to produce the image frame sequence. At step 2711, a switchable optical source is activated and excited using optical energy from an optical source (such as shown and described in FIG. 28). At step 2712, an image frame is captured at each detector in the interferometric microscope system and step 2711 is repeated N times to produce an image frame sequence. The image frames captured at each detector contain phase-related characteristics that are phase-shifted relative to the information in the image frames captured at the other detectors. The image frames are based on optical energy intensities in the x,y plane relating to the emission distributions of the switchable optical sources.

At step 2721, the emission distributions of the switchable optical sources are fit to a predetermined distribution to localize the emission distributions of the switchable optical sources in the x,y plane. For example, certain switchable optical sources have emission distributions that can be accurately fit to Gaussian distributions. Such Gaussian distributions can represent, for example, a point spread function of the images of optical emitters. At step 2722, the image frames are corrected for drift using the fiducials included in the image frames. The drift-corrected frames are then transformed at step 2723 to produce transformed frames that align the fiducials in the image frames of the image frame sequence in the x,y plane.

At step 2724, the image frames captured at each of the image detectors for each position in the z plane are summed into summed image frames. At step 2724, the transformed image frames captured at each of the image detectors are overlayed and summed (that is, the sum total is the image at the first detector plus the image at the second detector plus the image at the third detector for a three-phase system so that there may be many thousands of such summed triplets in a three-phase case). The summed image frames are a composite of the interfered image frames captured by each detector. At step 2725, the summed image frames are fit to a predetermined distribution to determine the centers of the switchable optical sources in the x,y plane.

The transformed frames are fit to a predetermined distribution, such as a Gaussian distribution, and the amplitude of the emission distribution of the switchable optical source in each frame is measured at the centers of the switchable optical sources in the x,y plane determined in step 2725 (step 2726). The center of the optical emitter can be based on, for example, the centroid of a Gaussian distribution representing a likelihood of the location of an optical emitter. At step 2727, the amplitudes of the emission distributions into each of the detectors of the switchable optical source are normalized to the sum determined at step 2724. At 2728, the normalized amplitudes determined at 2727 are used to obtain the z coordinate of the switchable optical source by correlation with calibration data recorded at previous step 2628. Such calibration data can be stored, for example, in a lookup table. The z coordinate can be calculated based on the normalized amplitudes, for example, by determining the minimum chi-square of: $[CA_1(z)-PA_1]^2+[CA_2(z)-PA_2]^2+[CA_3(z)-PA_3]^2+ \ldots + [CA_N(z)-PA_N]^2$, where N is the number of detectors in the system; $CA_i(z)$ is the normalized peak optical energy intensity amplitude at detector i determined during calibration for a particular sample position in the z coordinate; and $PA_i$ is the normalized peak optical energy intensity amplitude at detector i determined from the current PALM image frame.

Figure 16:
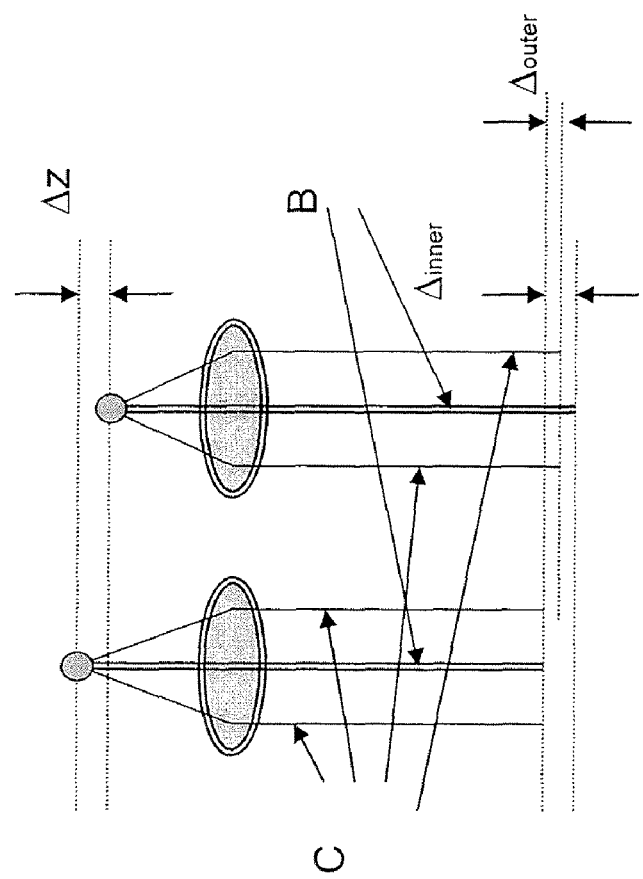
FIG. 16 is a diagram of a single quantum emitter in two different potential locations.
Figure 17:
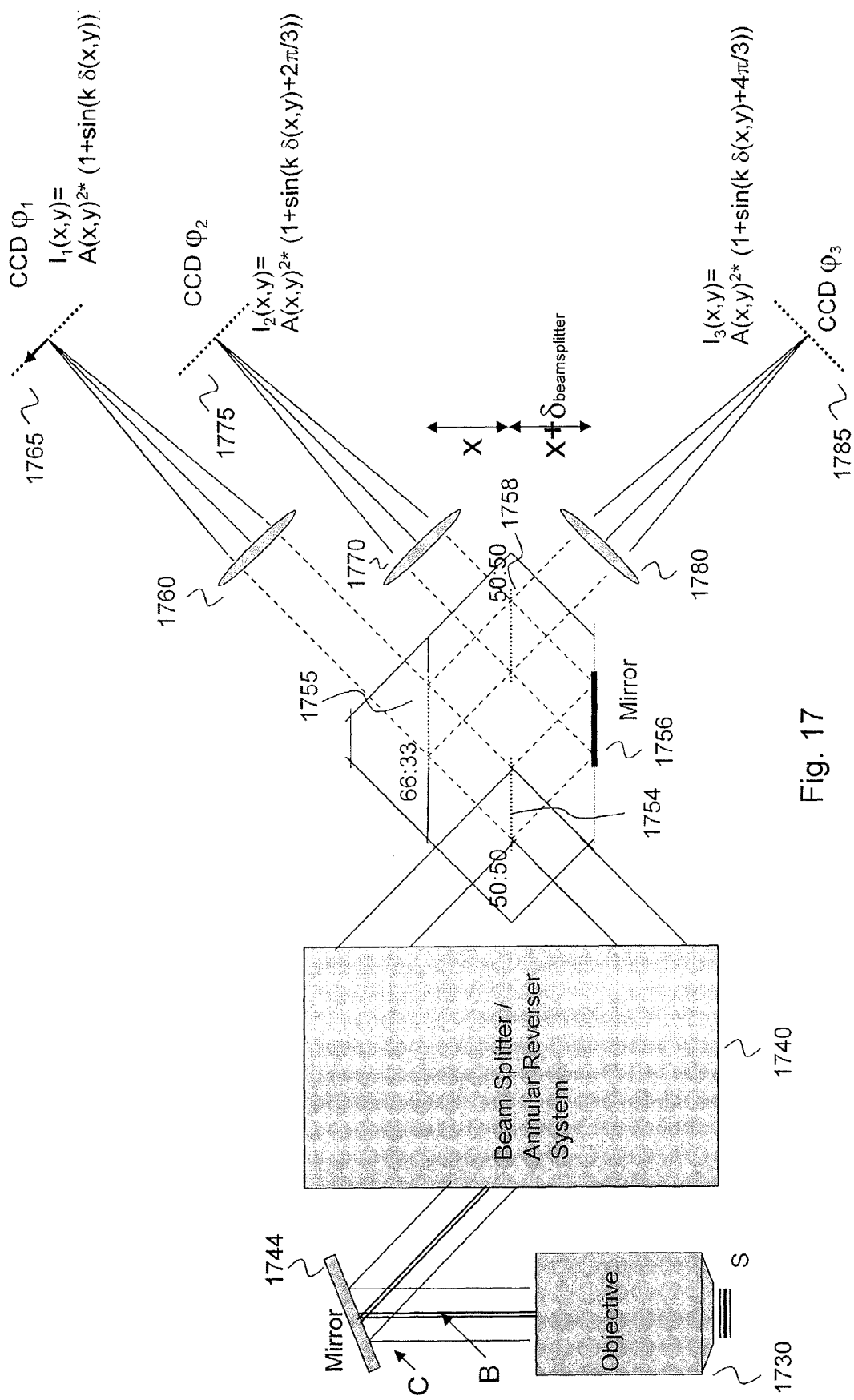
FIG. 17 is a block diagram of a three-phase interferometric microscopy system having a single objective.
Figure 18:
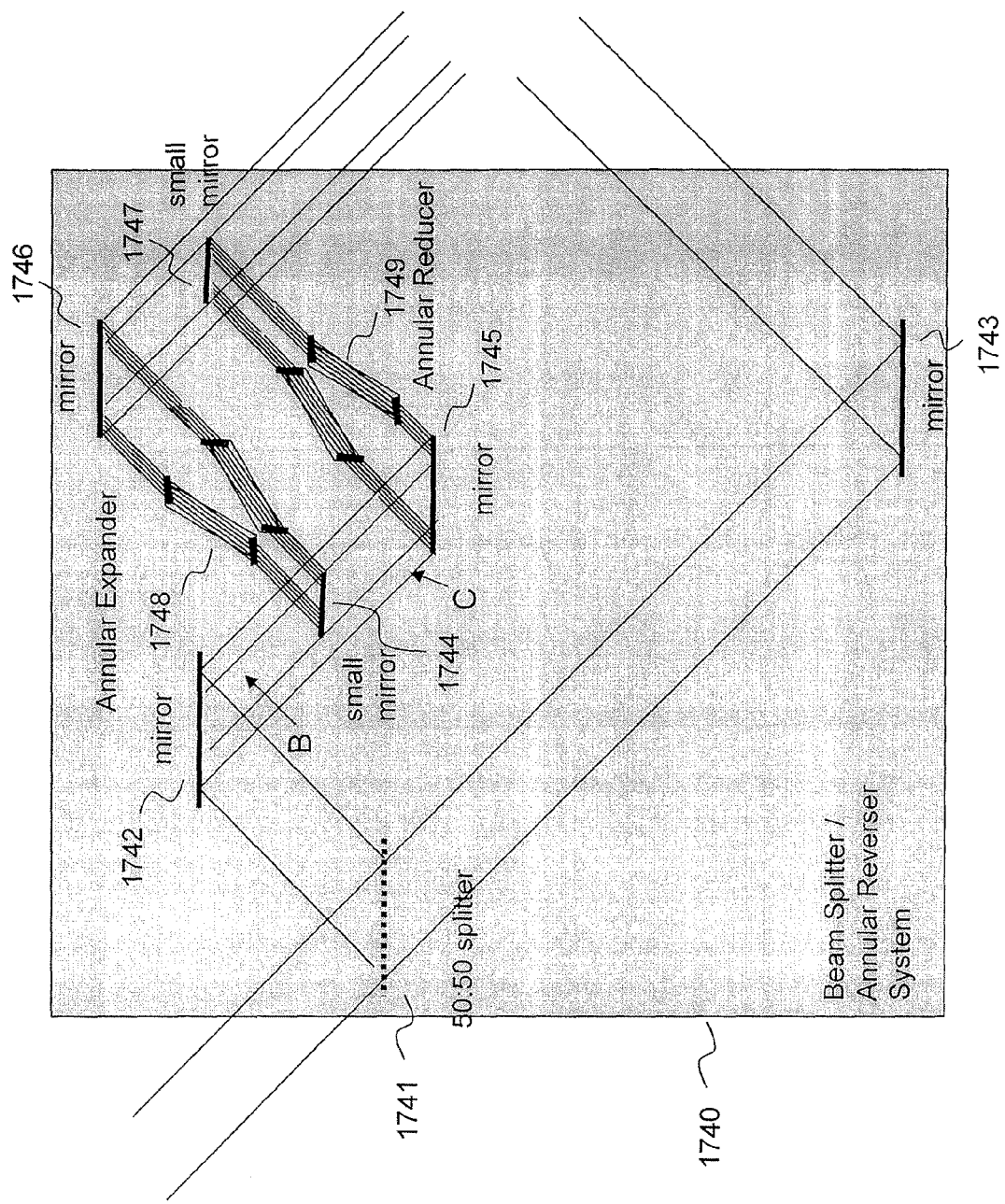
FIG. 18 is a block diagram of an example of the beam splitter/annular reverser system shown in FIG. 17.
Figure 21:
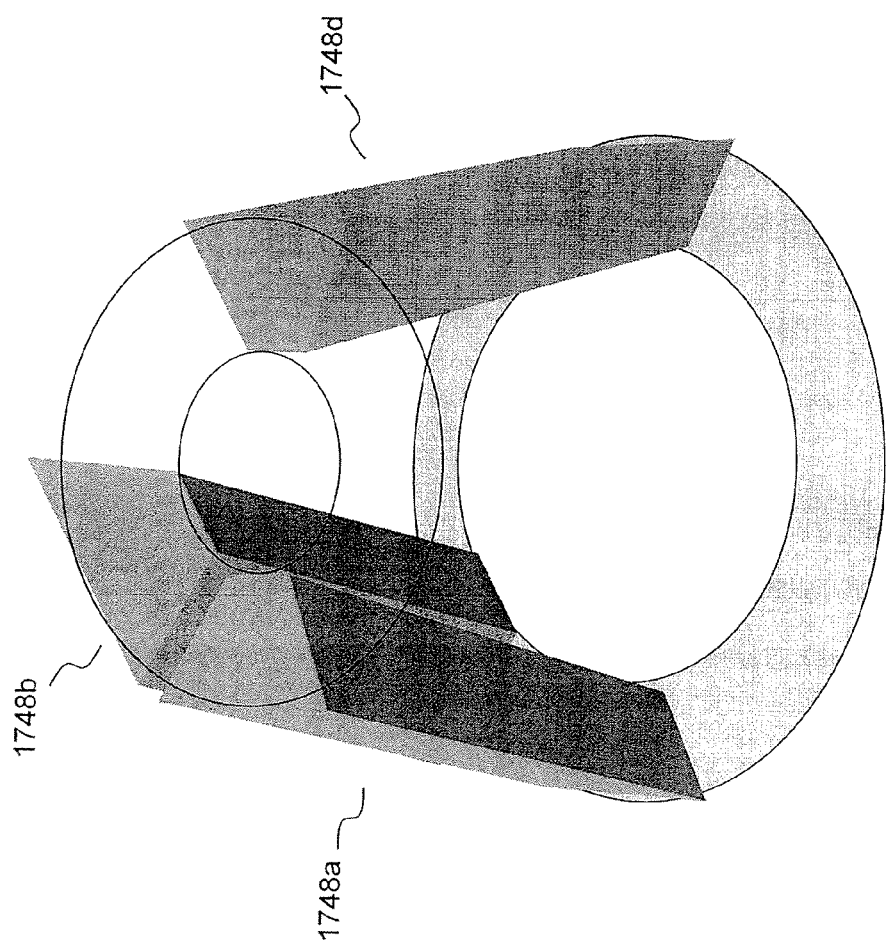
FIG. 21 is a perspective view of three out of the six prism components of the annular expander shown in FIG. 17.
Figure 22:
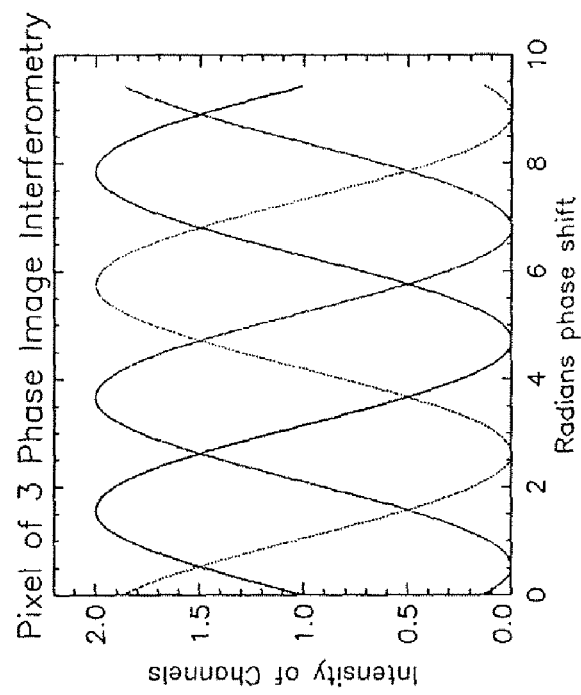
FIG. 22 is a graph of the intensities of the radiated light detected at the three detectors of FIG. 17.

In another implementation, an interferometric microscopy system can use different portions of the emitted beam that still generate a path length difference that varies with a third dimension z. Such an alternative implementation is discussed in connection with FIGS. 16-22. More specifically, FIG. 16 shows a diagram of a single quantum emitter in two different potential locations; FIGS. 17 and 18 show an example of a system block diagram of a three-phase interferometric microscopy system having a single objective; FIGS. 19-21 show an example of an annular expander of FIG. 18; FIG. 22 shows a graph of the intensities of the radiated light detected at the three detectors of FIG. 17. These figures are discussed below.

FIG. 16 shows an example of a single quantum emitter, in two possible locations. Such a quantum emitter can be, for example, a fluorescent molecule, a quantum dot or a sub-wavelength scattering center. A radiated photon (wavelength λ) propagates in all directions including a downward direction away from the objective shown in FIG. 17 and an upward direction into the objective shown in FIG. 17. The portion of the energy of the radiated photon propagating into the objective can be considered as two collimated beams of roughly equal strength: an inner cylindrical beam labeled "B" and an outer annular beam labeled "C." The size of inner beam portion B and outer beam portion C can be selected such that their intensities are substantially equal; such substantially equal intensities correspond to different beam portion areas due to the non-linear intensity profile of the beam (for example, the peak of the beam energy is in the center of the beam with the intensity reducing towards the edges of the beam). For example, the inner beam portion labeled "B" can have a radius equal to approximately one third of the total beam radius; the outer beam portion labeled "C" can have an inner radius corresponding to the radius of the inner beam portion "B" and an outer radius corresponding to the radius of the total beam.

When the sample is exactly in focus, these beam portions are matched and in phase (as shown in the left side of FIG. 16). When, however, there is a positional displacement Δz of the emitter (as shown in the right side of FIG. 16), the phase beam portions B and C are displaced by $\Delta_{inner}$ and $\Delta_{outer}$, respectively, where $\Delta_{inner}$ equals Δz and $\Delta_{outer}$ equals Δz*cos(θ). This displacement of the phase beam portions B and C is due to the fact that the outer beam portion C undergoes less of an optical path change by a factor of cos(θ), where θ is the initial cone angle of rays from the emitter. Consequently, a differential phase shift between the two beams remains and equals: $\delta=2\pi(\Delta_{inner}-\Delta_{outer})/\lambda=\Delta z^*(1-\cos(\theta))^* 2\pi n/(\lambda)$.

The z range over which the phase increases through 360 degrees and repeats is: λ/(n(1−cos(θ))). This z range for this single-objective implementation is longer than the z range of the opposing-objective implementations discussed above in connection with FIGS. 1-11. The index of refraction, n, of the optical environment around the emitter rescales the phase shift. An implementation of a single-objective system is discussed in more detail below in connection with FIGS. 17-20.

FIG. 17 shows an example of a system block diagram of a three-phase interferometric microscopy system having a single objective. FIG. 18 shows an example of a system block diagram of the beam splitter/annular reverser system shown in FIG. 17. As shown in FIG. 17, the interferometric microscopy system includes an objective 1730; a mirror 1744; a beam splitter/annular reverser system 1740; mirror 1756;

beam splitters 1754, 1755, and 1758; lenses 1760, 1770, and 1780; and detectors 1765, 1775, and 1785. As shown in FIG. 18, the beam splitter/annular reverser system 1740 includes a beam splitter 1741, mirrors 1742-1747, annular expander 1748, and annular reducer 1749.

The annular expander 1748 can be any type of device that receives light having a given radius and expands the radius of the light. For example, the annular expander 1748 can receive the inner cylindrical beam of light from the mirror 1742 (similar in cross-sectional shape to the inner beam "B" discussed in reference to FIG. 17) and can produce light having an annular shape with a larger outer diameter (for example, similar in cross-sectional shape to the outer beam "C" discussed in reference to FIG. 17). Similarly, annular reducer 1749 can be any type of device that receives light having a given radius and reduces the radius of light. For example, the annular reducer 1749 can receive the outer annular beam of light from the mirror 1742 (similar in cross-sectional shape to the outer beam "C" discussed in reference to FIG. 17) and can produce light having an inner cylindrical shape (or smaller annular shape) with a smaller inner diameter (for example, similar in cross-sectional shape to the inner beam "B" discussed in reference to FIG. 17).

FIGS. 19-21 show an example of an annular expander shown in FIG. 18. More specifically, FIG. 19 shows a cross-sectional view of the annular expander shown in FIG. 18; FIG. 20 shows an end view of the annular expander shown in FIG. 18; and FIG. 21 shows a perspective view of three out of the six prism components of the annular expander shown in FIG. 18. As shown in FIG. 19-21, the annular expander 1748 has six prisms 1748a-1748f spaced about a centerline of the annular expander 1748 such that one end of the six prisms 1748a-1748f collectively defines an annular-like, multi-faceted surface having a size different from the size of the annular-like, multi-faceted surface collectively defined by the other end of the six prisms 1748a-1748f. The light enters the end of the prisms 1748a-1748f defining the smaller, annular-like, multi-faceted surface and exits the end of the prisms 1748a-1748f defining the larger, annular-like, multi-faceted surface, as shown in FIG. 19. FIG. 20 shows the end view of the annular expander 1748 from the larger, annular-like, multi-faceted surface towards the smaller, annular-like, multi-faceted surface into the page. Although not explicitly shown, the annular reducer 1749 would be configured similar to the annular expander 1748 except that light enters the end of the prisms defining the smaller, annular-like, multi-faceted surface and exits the end of the prisms defining the larger, annular-like, multi-faceted surface.

Returning the FIGS. 17 and 18, the three-phase interferometric microscopy system will now be described with reference to light propagating through the system. As shown in FIG. 17, energy is radiated as an optical beam from the sample (labeled "S" in FIG. 17) and is reflected by the mirror 1744 toward the beam splitter/annular reverser system 1740. The 50:50 beam splitter 1741 of beam splitter/annular reverser system 1740 (shown in FIG. 17) sends a portion of the light to mirror 1742 and a remaining portion of the light to mirror 1743. To separate the light into two beam portions, the mirror 1742 reflects an outer beam portion C towards the mirror 1745 while reflecting an inner beam portion beam B to the mirror 1744. The mirrors 1745 and 1744 reflect the outer beam portion C and the inner beam portion B, respectively, to the annular expander 1748 and the annular reducer 1749, respectively. The annular expander 1748 expands its received light towards the mirror 1746, which reflects the expanded light towards the beam splitter 1754 (shown in FIG. 17).

Similarly, the annular reducer 1749 reduces the radius of its received light towards the mirror 1747, which reflects the reduced light towards the 50:50 beam splitter 1754.

The 50:50 beam splitter 1754 reflects half of the light received from the mirrors 1746 and 1747 to the 66:33 beam splitter 1755 and transmits the other half of the light to the mirror 1756. The 50:50 beam splitter 1754 also reflects half of the light received from the mirror 1743 to the mirror 1756 and transmits the other half of the light to the 66:33 beam splitter 1755. The 66:33 beam splitter 1755 reflects 33% of the received beam towards the 50:50 beam splitter 1758 and transmits the remaining 66% of the received beam towards the lens 1760. The mirror 1756 reflects the received beam to the 50:50 beam splitter 1758 while also adding an extra phase shift. The 50:50 beam splitter 1758 reflects 50% of the received beam from the mirror 1756 towards the lens 1780 and transmits 50% of the received beam from the mirror 1756 towards the lens 1770. The 50:50 beam splitter 1758 also reflects 50% of the received beam from the 66:33 beam splitter 1755 towards the lens 1770 and transmits 50% of the received beam from the 66:33 beam splitter 1755 towards the lens 1780.

Note that the 50:50 beam splitters 1754 and 1758, the mirror 1756, and the 66:33 beam splitter 1755 can be arranged such that a difference exists in the light path lengths. More specifically, the optical path distance, x, between the 50:50 beam splitters 1754 and 1758 and the 66:33 beam splitter 1755 can be less than the distance, $x+\delta_{beamsplitter}$, between the 50:50 beam splitters 1754 and 1758 and the mirror 1756. Assuming, for example, that the optical path difference between the two distances, $\delta_{beamsplitter}$, can be selected to be ⅛ of the wavelength, λ, and the wavelength, λ, is 580 nm, the difference between the two distances, $\delta_{beamsplitter}$, can be selected at 72 nm.

The beam sent to the lens 1760, the beam sent to the lens 1770, and the beam sent to the lens 1780 each have substantially equal amplitudes. The lenses 1760, 1770 and 1780 focus the respective beams to the detectors 1765, 1775, and 1785. The intensity of the emitted image on each of the three detectors 1765, 1775, and 1785 changes as a function of the source phase (that is, the z position at the sample) because the relative intensities among the three detectors 1765, 1775, and 1785 have about a 120-degree phase shift. FIG. 22 shows a graph of the intensities of the radiated light detected at the three detectors shown in FIG. 17. By monitoring the intensities detected by the three detectors 1765, 1775, and 1785, the phase shift from the initial offset between the inner beam portion B and the outer beam portion C can be estimated as described above in connection with FIGS. 1-11.

This source phase shift, δ, can be used to calculate the z position of the emitter: $\Delta z=\delta\lambda/(n(1-\cos(\theta)))$.

In some implementations, calibration techniques can be used to correct for non-balanced intensity sensitivities of the detectors and phase mixing angles. Although the implementations shown in FIGS. 17-22 are described with respect to three detectors having approximately 120-degree phase shifts, other implementations having a different number of detectors are possible. In yet other implementations, the imaged spot shape can be used to resolve any cyclic or positional ambiguity. Alternatively, the imaged spot shape can be used as additional information for the positional calculation.

Figure 23:
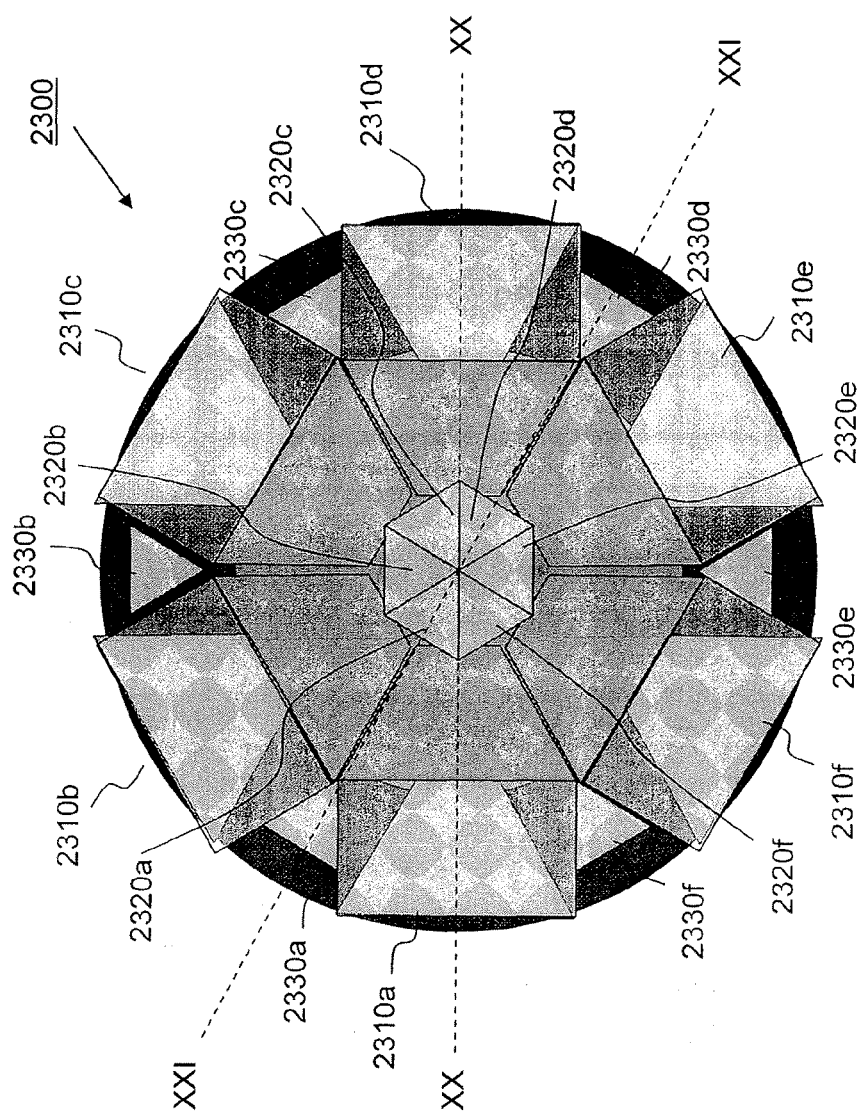
FIG. 23 is a plan view of the annular expander.
Figure 25:
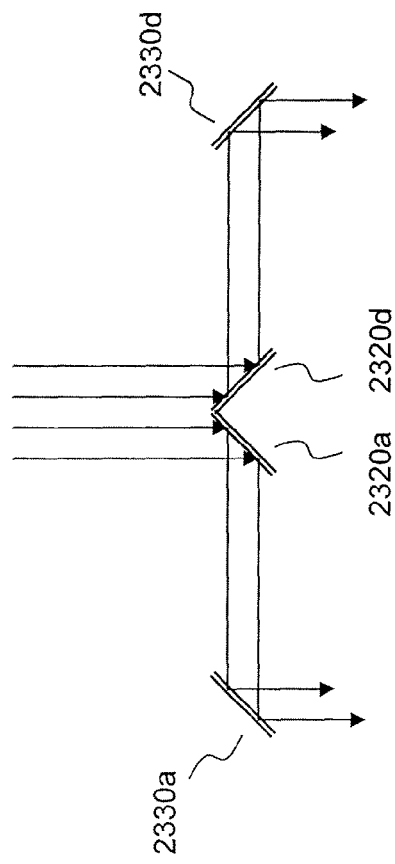
FIG. 25 is a cross-sectional view of the annular expander shown in FIG. 23 taken along line XXI-XXI.
Figure 24:
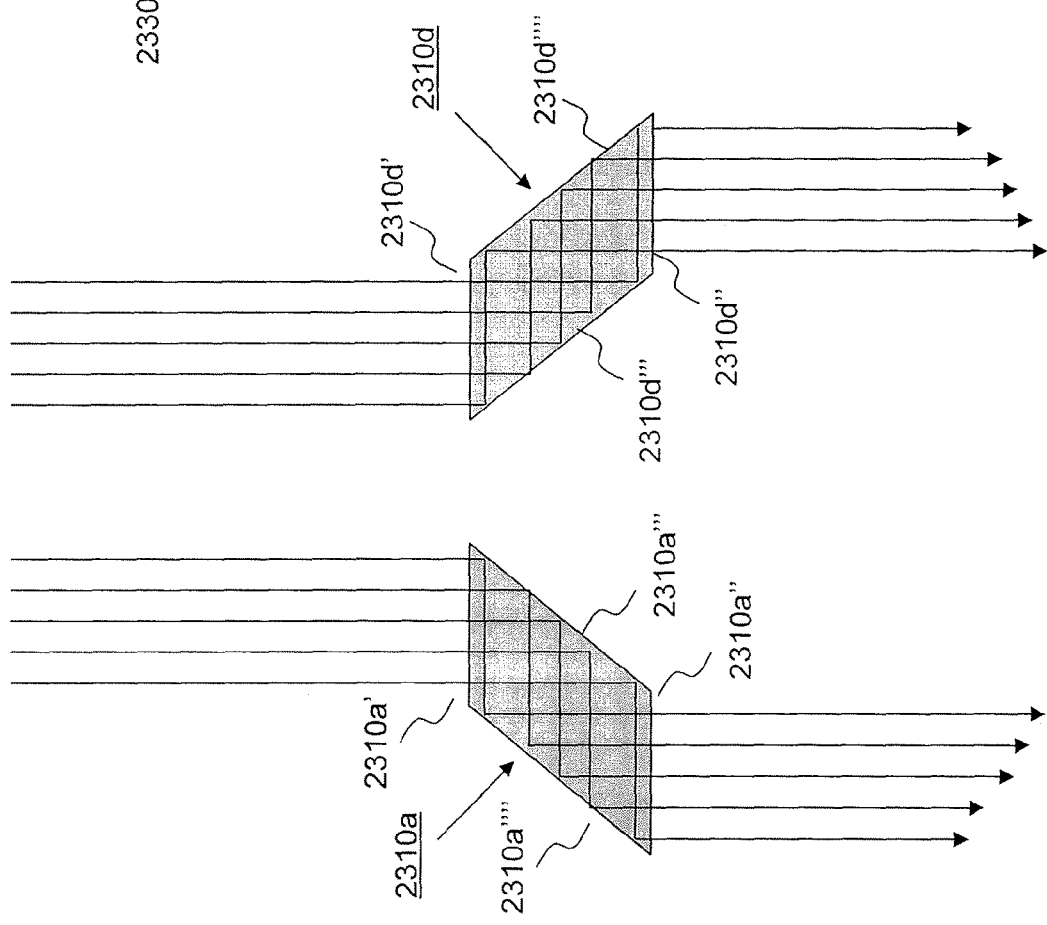
FIG. 24 is a cross-sectional view of the annular expander shown in FIG. 23 taken along line XX-XX.

FIGS. 23-25 show an example of an annular expander. More specifically, FIG. 23 shows an end view of the annular expander; FIG. 24 shows a cross-sectional view of the annular expander of FIG. 23 along the line XX-XX; FIG. 25 shows a cross-sectional view of the annular expander of FIG. 23 along the line XXI-XXI. As shown in FIGS. 23-25, the annular expander 2300 has six prisms 2310a-2310f, six mirrors 2320a-2320f and six mirrors 2330a-2330f. The prisms 2310a-2310f are spaced about a centerline of the annular expander 2300 such that one end of the six prisms collectively defines an annular-like surface having a size different from the size of the annular-like surface collectively defined by the other end of the six prisms. The mirrors 2320a-2320f are arranged about the centerline of the annular expander 2300 and within an interior central portion defined by the six prisms 2310a-2310f. The mirrors 2330a-2330f are arranged about the centerline of annular expander 2300 and about an outer portion defined by the gaps between the adjacent prisms 2310a-2310f.

As shown in FIG. 24, each prism 2310 includes an ingress face 2310' and an egress face 2310". The ingress face 2310' is parallel to and has a smaller inner radius and outer radius than egress face 2310". Each prism 2310 also includes two side walls 2310''' and 2310'''' angled relative to the ingress face 2310' and the egress face 2310" such that the condition for total internal reflection (TIR) is satisfied. Thus, light enters each prism 2310 at the ingress face 2310', undergoes a reflection due to TIR at side wall 2310''' and a reflection due to TIR at side wall 2310'''', and then exits from the egress face 2310". This allows the radius of the incident light to be expanded as it exits the annular expander 2300.

As shown in FIG. 25, the mirrors 2320a-2320f reflect the light along and near the centerline of annular expander 2300 outwardly towards the mirrors 2330a-2330f, respectively. The mirrors 2330a-2330f reflect the received light between the gaps defined by the adjacent prisms 2310a-2310f. For example, the mirror 2320a reflects a portion of light near the centerline of the annular expander 2300 towards the mirror 2330a, which reflects this light between the gap defined between the prism 2310a and the prisms 2310b. Collectively, this allows the central portion of the light to be expanded, providing increased throughput.

Although not explicitly shown, an annular reducer can be configured similar to the annular expander 2310 except that light enters the end of the prisms defining the larger, annular-like surface and exits the end of the prisms defining the smaller, annular-like surface. Although the implementations shown in FIGS. 19-20 and 23-25 shown with specific refractive and/or reflective components, other implementations and arrangements are possible including, for example, implementations having diffractive components or any combination thereof.

Determining the Unique Vertical Position

As discussed above, $\phi_i$ is a cyclic solution, therefore, for every $2\pi$, the uniquely determinable range extends $\lambda/2n$. Thus, a set of possible z positions $\delta_i$ is initially determined as discussed above and is given by the general formulas noted above depending on the setup. For example, for the system that has two objectives, the general formula for the set of possible z positions is $\delta \cong \lambda^* \phi_i/(4\pi n) = \lambda/(4\pi n)^* \mathrm{atan}(\Sigma_j D_{ij} \sin(\phi_j)/\Sigma D_{ij} \cos(\phi_j))$. As discussed below with respect to FIGS. 28-40B, the system and method described above can be modified to determine the position of the optical source in the third orthogonal dimension (the z dimension) out of the set of possible positions.

Figure 28:
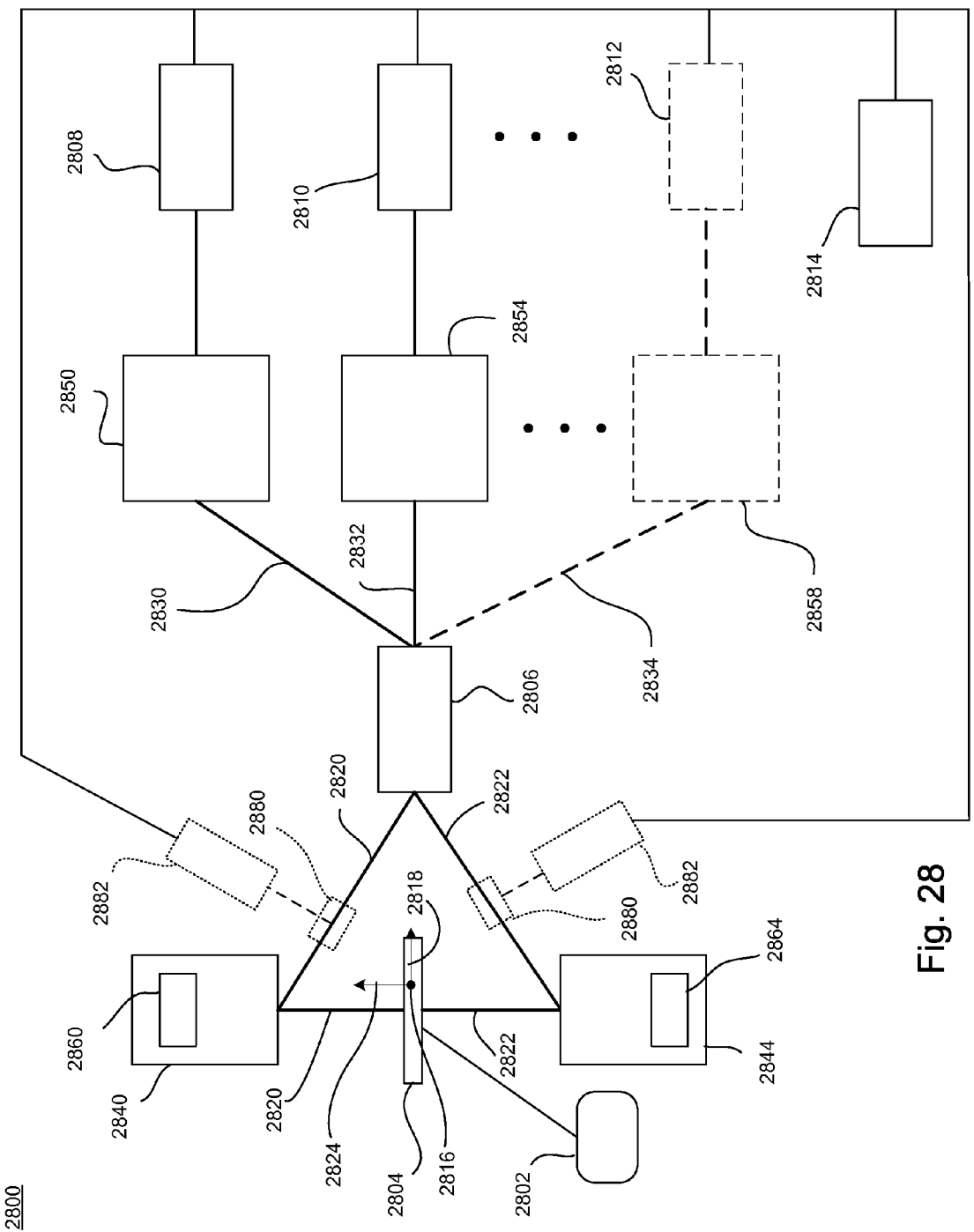
FIG. 28 is block diagram of a multi-phase interferometric microscopy system and a sample.

Referring to FIG. 28, a multi-phase interferometric microscopy apparatus 2800 includes an optical actuation system 2802 optically coupled to a sample 2804, an interference system 2806, at least two detectors 2808, 2810, 2812, and a controller (for example, a processor) 2814 connected to the at least two detectors 2808, 2810, 2812. At least two detectors 2808, 2810 are shown, but additional detectors (such as detector 2812) can be used, depending on the geometry and of the interference system 2806.

Throughout the remaining part of the specification, the following conventions are followed when describing coordinate systems. There are two coordinate systems or frames of reference used. The first coordinate system is the sample (or object) coordinate system, which is a stationary coordinate system at the location of the sample. The sample coordinate system is defined by a set of orthogonal dimensions at the sample location: a first sample dimension 2816 (also referred to as the x dimension, which is directed out of the page), a second sample dimension 2818 (also referred to as the y sample dimension), and a third sample dimension 2824 (also referred to as the z sample dimension or the vertical dimension). The first and second sample dimensions 2816, 2818 are also referred to as lateral dimensions and the third sample dimension 2824 is also referred to as an axial dimension. The second coordinate system is the beam coordinate system, which is a movable coordinate system that travels with beam. The beam coordinate system is defined by the beam propagation direction and two directions that are transverse or perpendicular to the beam propagation direction.

The sample 2804 extends generally along a sample plane defined by the first orthogonal sample dimension 2816 and the second orthogonal sample dimension 2818. The optical actuation system 2802 is configured to cause the optical source in the sample 2804 to emit optical beams in a plurality of optical paths, and specifically emit first and second optical beams along two diametrically opposite optical paths or beam propagation directions 2820, 2822 that are generally parallel with the third orthogonal sample dimension 2824 and that are directed to the interference system 2806 after passing through the objectives within objectives of the optical components 2840, 2844. The optical actuation system 2802 is optically coupled to the sample 2804 and configured to activate a sufficiently statistically sparse subset of switchable optical sources in the sample 2804. Activation can be can be any activity that creates the controlled sparse active label density where the optical sources are separated at least by a diffraction limited distance. Thus, optical sources can be added by activation if there are too few sources that meet this separation or optical source can be depleted by reducing activation if there are too many sources separated by less than the diffraction limited distance. The system 2802 can also excite the activated switchable optical sources such that the optical beams are emitted from the activated switchable optical sources along the plurality of optical paths, and specifically along the optical paths 2820, 2822 that cross the interference system 2806.

Thus, the optical actuation system 2802 can include a first laser that radiates the sample 2806 with an activation beam and a second laser that excites the activated switchable optical sources in the sample 2804 with an excitation beam. In other implementations, the optical actuation system 2802 can include one or more of a light-emitting diode and an incandescent lamp that operate as activation and/or excitation sources. The optical actuation system 2802 operates at a wavelength that is distinct from the wavelength of the optical beam emitted from the sample 2804 to reduce the amount of noise reaching the detectors 2808, 2810, 2812.

The interference system 2806 is configured to receive the first and second optical beams emitted from the optical source, divide each of the first and second optical beams into two or more divided beams, and combine at least two or more of the divided beams to form a plurality of combined beams that are directed along respective optical paths (or beam propagation directions) 2830, 2832, 2834. Each of the combined beams (traveling along paths 2830, 2832, 2834) includes an interference between the two or more divided beams caused at least in part by a difference in phase between the optical beams due to a difference in the optical path length of the optical beams relative to the location of the optical source. The interference system 2806 can be any of the beam splitters described above, for example, beam splitters 150, 250, or 1050, or the beam splitters shown in FIGS. 8, 8A, 8B, 10, 11, 12, 14, 15, 17, and 18.

The apparatus 2800 includes optical components 2840, 2844, which can be any type of optical components that define the respective optical path 2820, 2822 from the sample 2804 to the interference system 2806. Each of the optical components 2840, 2844 can include one or more mirrors, lenses, or objectives. Each of the optical components 2840, 2844 can include lenses or objectives that collimate optical energy emitted from the optical sources in the sample 2804. As discussed above, one or more of the optical components 2840, 2844 can include an aperture through which optical energy from the optical actuation system 2802 can irradiate the sample 2804 while reducing the amount of stray radiation that travels from the excitation laser of the optical actuation system 2802 towards the detectors 2808, 2810, 2812.

The apparatus 2800 also includes optical components 2850, 2854, 2858, each of which receives the respective combined beam traveling along the optical path 2830, 2832, 2834 from the interference system 2806 and redirects the combined beam toward the respective detector 2808, 2810, 2812. The detectors 2808, 2810, 2812 are configured to separately detect an intensity of each of the combined beams output from the interference system, as discussed above.

The processor 2814 is connected to the detectors 2808, 2810, 2812 and is configured to perform a procedure to determine a unique position δ along the vertical dimension of the optical source in the sample 2804 out of the set of possible vertical positions for samples that are thicker than λ/2n, where λ is the wavelength of the light in the combined beams and n is the index of refraction of the medium of the sample 2804. As discussed above, for samples thicker than λ/2n, an ambiguity exists in determining the vertical position δ by ±N λ/2n for an integer N. The processor 2814 uses other attributes (such as image changes that are induced by wavefront modifications of the optical beams or the combined beams) to find the most likely N and chooses the best vertical position of a multi-valued solution. The attributes used by the processor 2814 are attributes that vary with the vertical position of the optical source.

The wavefront modifications of the optical beams or the combined beams used by the processor 2814 can be modifications caused by interactions of the optical beams and/or the combined beams as they travel through the apparatus 2800.

Alternatively or additionally, the apparatus 2800 can include a wavefront modification system 2860, 2864 in at least one of the respective optical components 2840, 2844. The wavefront modification system 2860, 2864 is configured to actively introduce the variable wavefront modification of the at least one optical beam and/or combined beam. As discussed below in detail with respect to FIGS. 31A, 36A, 39A, and 40A, the wavefront modification system 2860, 2864 can include one or more devices that introduce one or more of a defocus, a curvature, and a brightness variance into the combined beams that reach the detectors 2808, 2810, 2812.

In some implementations, the apparatus 2800 includes a beam splitter 2880 positioned in one or more of the optical paths 2820, 2822 to filter out a small percentage of light that would otherwise be directed to the interference system 2806. The beam splitter 2880 directs the light toward a detector system 2882, which can include optical components and a detector that is also connected to the processor 2814, as discussed below with respect to FIGS. 37A and 38. The detector system 2882 can include optical components that actively introduce the variable wavefront modification to the optical beam, as discussed below with respect to FIG. 37A.

Figure 29:
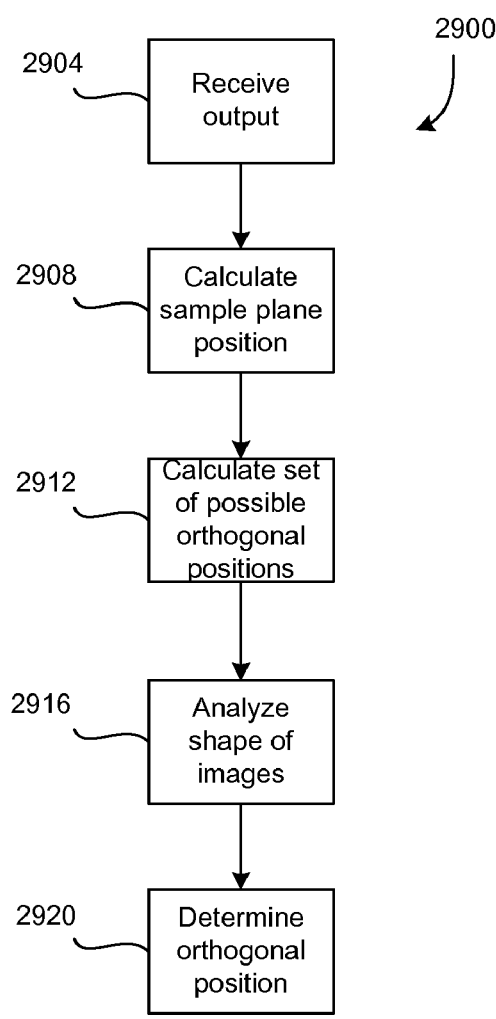
FIG. 29 is flow chart of a procedure performed by a processor of the system of FIG. 28.

Referring to FIG. 29, the processor 2814 performs a procedure 2900 to determine the unique vertical position δ of the optical source in the sample 2804. The processor 2814 receives the electronic output from the detectors 2808, 2810, 2812 (or from the detector in the detector system 2882) (step 2904). The detectors 2808, 2810, 2812 detect the image of each of the combined beams and converts the data of the image into an electronic signal. The processor 2814 calculates a position of the optical source in the sample plane to sub-diffractive accuracy based on a center region of the image of each combined beam from the detectors 2808, 2810, 2812 (step 2908), as discussed in detail above. As also detailed above, the processor 2814 calculates a set of possible positions of the optical source in a third orthogonal dimension (the vertical direction) that is perpendicular to the sample plane based on separately detected intensities of each combined beam from the detectors 2808, 2810, 2812 (step 2912). Thus, in steps 2908 and 2912, the processor 2814 performs the photo-activated localization interferometric microscopy procedure that is detailed above and is not repeated in this section.

The processor 2814 analyzes an attribute (for example, the shape or a peak value) of an image of the combined beam (or of the optical beam if the detector system 2882 is set up in a path 2820, 2822) that varies with the position of the optical source along the third orthogonal dimension based on the wavefront modification (step 2916). As discussed in greater detail below, the wavefront modification is a modification of one or more of a curvature (for example, a defocusing or an astigmatism) and a shape of a wavefront of at least one optical beam emitted from the optical source of the sample 2804.

The processor 2814 determines the position of the optical source in the third orthogonal dimension out of the set of possible positions based the analyzed shape (step 2920).

Figure 30:
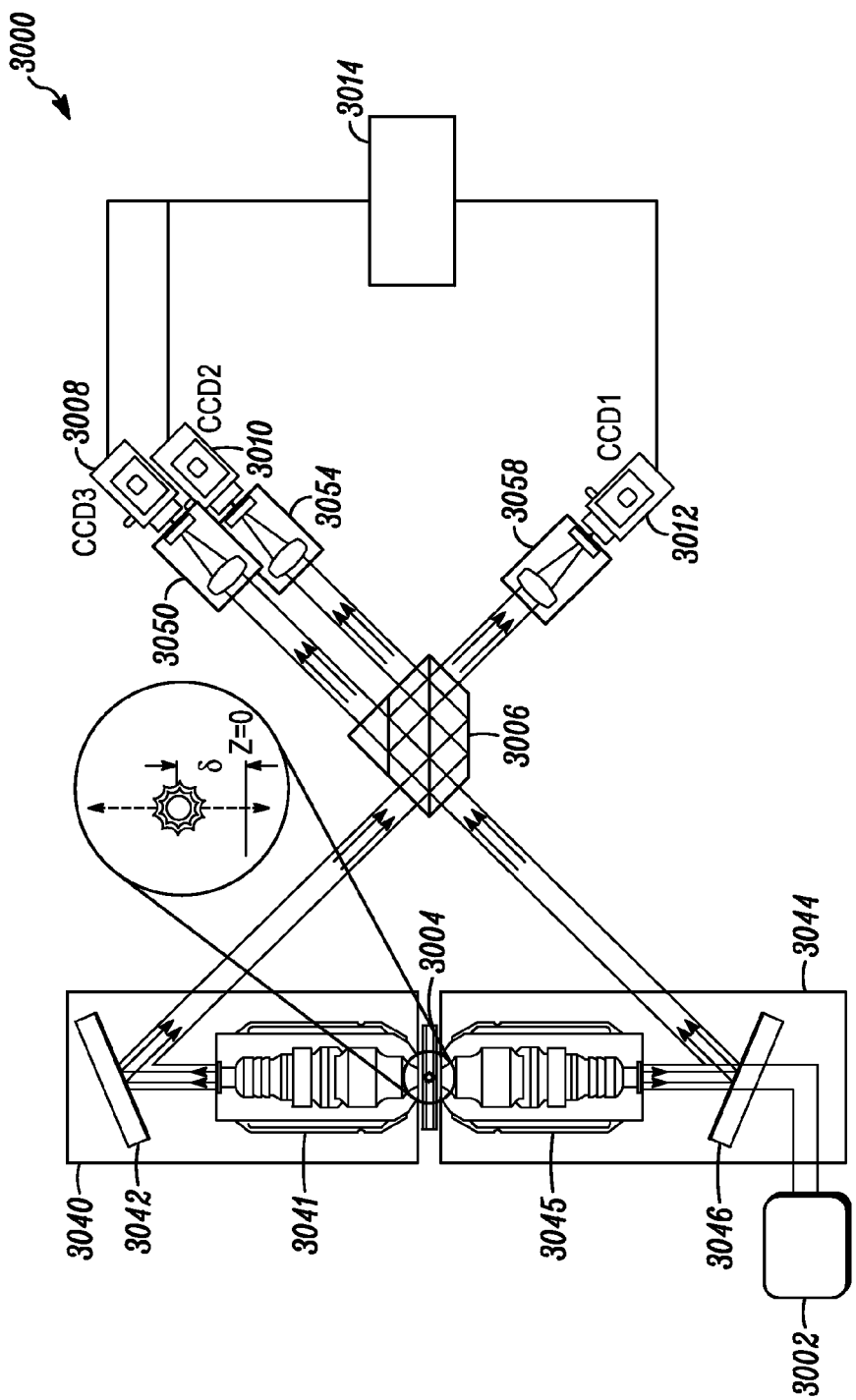
FIG. 30 is a block diagram of a three-phase interferometric microscope system.

Referring to FIG. 30, a multi-phase interferometric microscopy apparatus 3000 includes an optical actuation system 3002 optically coupled to a sample 3004, an interference system 3006, at least two detectors 3008, 3010, 3012, and a controller (for example, a processor) 3014 connected to the at least two detectors 3008, 3010, 3012. The apparatus 3000 includes optical components 3040, 3044 on either side of the sample 3004 and optical components 3050, 3054, 3058 between the interference system 3006 and respective detectors 3008, 3010, 3012.

The optical components 3040, 3044 each include an objective 3041, 3045 and a mirror 3042, 3046. The objectives 3041, 3045 form collimated optical beams that are directed toward the respective mirrors 3042, 3046 and the mirrors 3042, 3046 redirect the optical beams toward the interference system 3006.

The beams that reach the detectors 3008, 3010, 3012 each are changed by a wavefront modification so that the image varies with the position of the optical source in the third orthogonal dimension. This wavefront modification can be actively added to the apparatus 3000 by, for example, adding an optical element between the sample 3004 and the interference system 3006 to modify the wavefront (as shown, for example, in FIG. 36A, 37A, or 38), or by modifying one of the optical elements within the optical components 3040, 3044 (as shown, for example, in FIG. 31A, 39A, or 40A) to modify the wavefront of the optical beams and therefore the combined beams that reach the detectors 3008, 3010, 3012. The wavefront modification can be an inherent property of the configuration of the apparatus 3000 and can be detected as shown in FIG. 38. In any case, the wavefront modification imparts a change to an attribute (for example, the shape) of the image at each of the detectors 3008, 3010, 3012, and that attribute modification can be analyzed to determine the position of the optical source in the third orthogonal dimension.

Figures 31A, 31B:
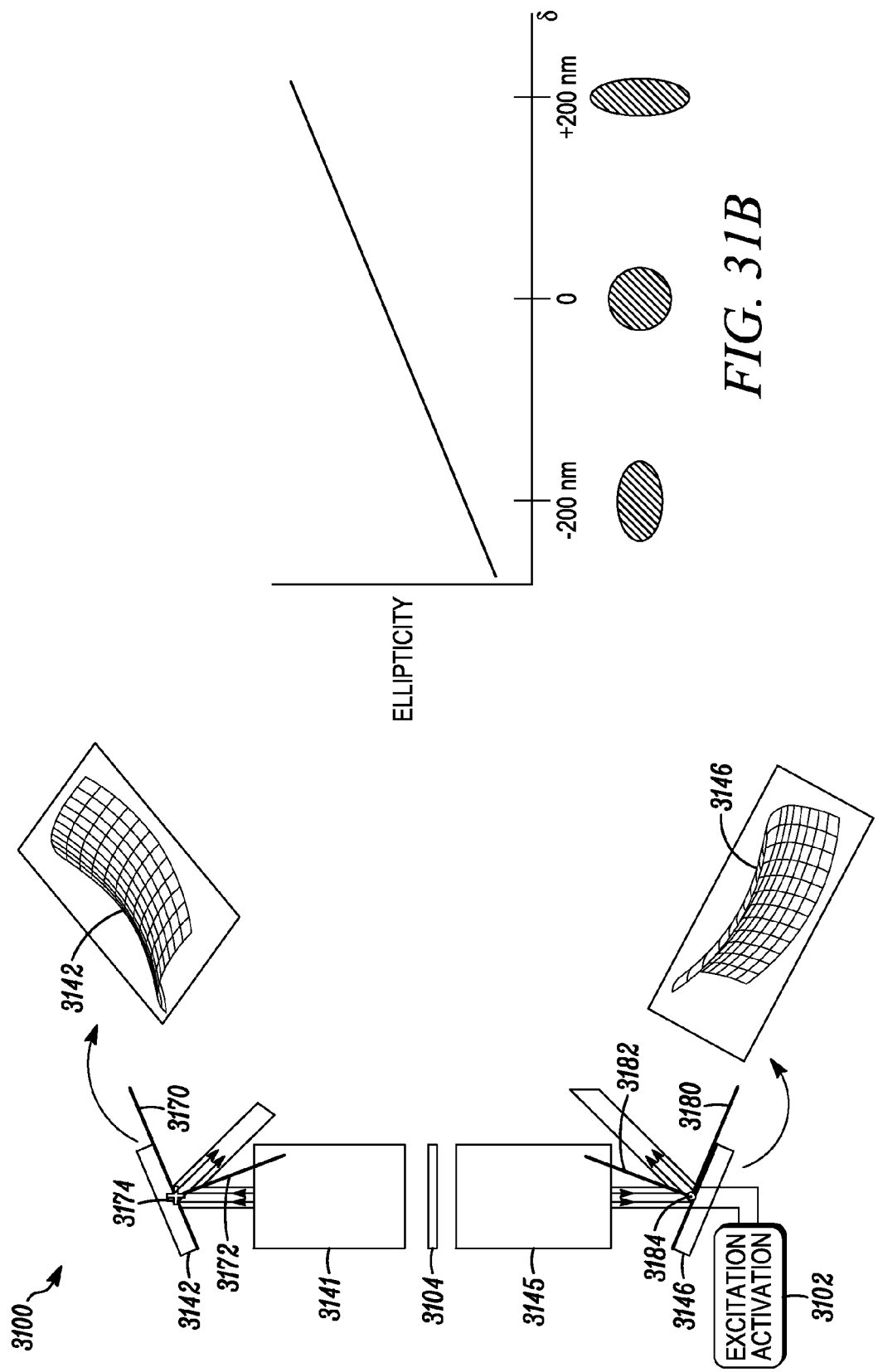
FIG. 31A is a block diagram of an exemplary portion of the interferometric microscope system of FIG. 28.
FIG. 31B is a generalized graph of the ellipticity versus vertical position of the optical source of a sample in the system of FIG. 31A.

Referring to FIG. 31A, a multi-phase interferometric microscopy apparatus 3100 includes mirrors 3142, 3146 that have been modified to each provide a relatively small modification of the wavefront curvature of the respective optical beam emitted from sample 3104. The mirrors 3142, 3146 can each be cylindrical (curved along only one direction) or biconic (that is, curved oppositely along two transverse directions and having a saddle or hyperbolic paraboloid shape). For example, the surface of the mirror 3142 is convex along a first direction 3170 that is transverse to a normal 3172 taken at the center of the mirror 3142 and is concave along a second direction 3174 (into the page) that is transverse to the normal 3172 and the first direction 3170 (as shown in greater detail in the enlarged view of the mirror 3142). Moreover, the surface of the mirror 3146 is concave along a first direction 3180 that is transverse to a normal 3182 taken at the center of the mirror 3146 and is convex along a second direction 3184 (out of the page) that is transverse to the normal 3182 and the first direction 3180 (as shown in greater detail in the enlarged view of the mirror 3146). The mirrors 3142, 3146 are designed to have opposite or complementary shapes so that the wavefronts of the optical beams reflected from the mirrors 3142, 3146 overlay with each other after passing through the interference system 3106, that is, the wavefronts of the combined beams overlay with each other after passing through the interference system 2806.

In some implementations, the mirrors 3142, 3146 are made by applying relevant forces to points along a front and/or back surface of a flat mirror to cause the flat mirror to curve in the manner needed to add the wavefront curvature modification. In other implementations, the mirror 3142, 3146 is made by polishing or coating a flat mirror to obtain the relevant curvature on the mirror surface.

As mentioned above, the optical beam that impinges upon the mirror 3142 or 3146 is collimated in that its wavefront is flat along both directions that are transverse to the beam propagation direction. Thus, the mirror 3142 or 3146 breaks up the symmetry between the transverse directions so that the wavefront is no longer flat in both transverse directions. The wavefront can be made to be curved in only one transverse direction using a cylindrical mirror or curved in both transverse directions (but in approximately opposite amounts) using a biconic mirror. Each mirror 3142, 3146 creates two slightly different focal planes for the two transverse directions relative to the respective beam propagation direction. As a result, the ellipticity and orientation of the image varies as the position of the optical source in the third orthogonal dimension changes relative to the sample plane (which is the location at which the vertical position δ is zero). Thus, an optical source that is at a zero vertical position correlates to an average focal plane at the detector and therefore the image at the detector appears round or symmetric. An optical source that is above the zero vertical position would be more focused in a first transverse direction than in a second transverse direction and would appear ellipsoidal at the detector with its long axis along the second transverse direction while an optical source that is below the zero vertical position would be more focused in the second transverse direction than in the first transverse direction and would appear ellipsoidal at the detector with its long axis along the first transverse direction.

The modification to the wavefront in each of the optical beams ultimately introduces a parabolically-varying phase of a first value along a first transverse direction (relative to the beam propagation direction) at the detector and a parabolically-varying phase of a second value along a second transverse direction (relative to the beam propagation direction) at the detector. In this way, a point source that is nearer to either the top or bottom objective has a focal plane along the first transverse direction that is separated from a focal plane along the second transverse direction.

As mentioned, the amount of curvature is chosen to be enough to impart enough defocus in the combined beams that reach the detectors to enable an accurate determination of the vertical position δ of the optical source in the sample out of the multiple value set determined using interferometry only. The induced curvature should cause a difference in phase between the center of the beam and the outer edge of the beam that is less than 4n or 2λ, where λ is the wavelength of the light. If the induced curvature is greater than this amount, then the image at the detector could be overly elliptical and as a result it would be more difficult to find the center along the extra elongated axis, which is important in order to determine the position of the optical source in the sample plane (along the x and y sample dimensions) or to determine the set of possible positions of the optical source along the z sample dimension. In particular, the precision of the optical source position in the sample plane is directly proportional to the fuzzy radius (that is, the Gaussian sigma) of the molecule image. Therefore, the amount of defocus due to the additional curvature is generally kept to about 20-30% over the operating range.

With the wavefront curvature induced by the mirrors 3142, 3146, the point-spread functions (PSF's) of the point sources become elliptical when measured at the detectors 2808, 2810, 2812. A generalized fit of the ellipticity ε as a function of the vertical position δ is shown in FIG. 31B along with the generalized fluorescent image at the detector at three distinct values of the vertical position δ. The processor 2814 analyzes the shape of the fluorescent images of the combined beams to determine the position of the optical source in the third orthogonal dimension.

Figure 32:
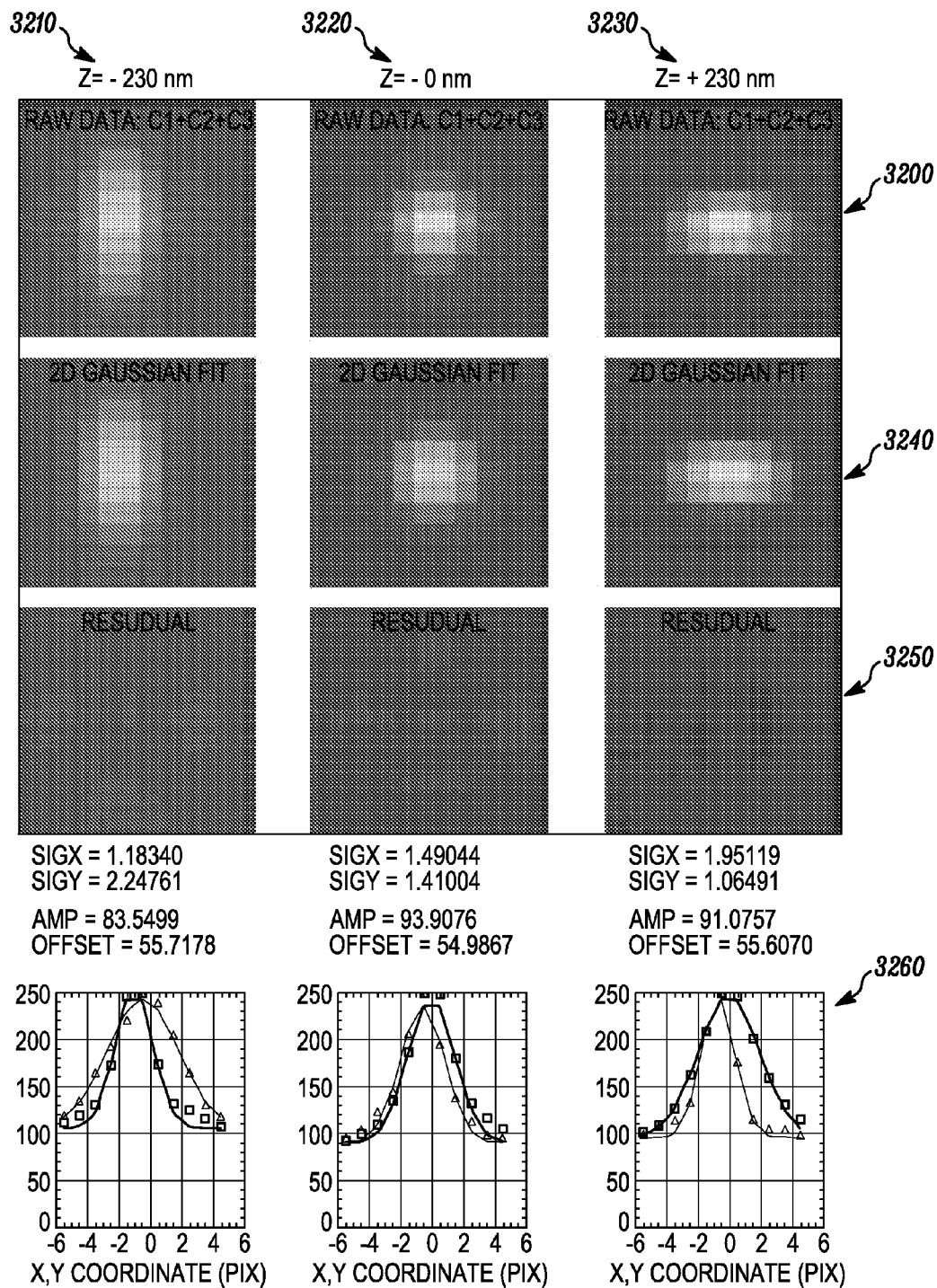
FIG. 32 is a table of the raw image data taken from detectors within the system of FIG. 31A, along with fits to the data, differences between the data and the fits, and cross-sections of the data.

Referring also to FIG. 32, actual diffraction-limited fluorescent images 3200 of a single gold nanoparticle (which acts as an optical source) are taken at the detectors for three distinct and known vertical coordinates Z of the nanoparticle. The nanoparticle is placed at known vertical coordinates Z=−230 nm (left column 3210), at Z=0 nm (center column 3220), and at Z=+230 nm (right column 3230). Gaussian fits 3240 corresponding to the images 3200 and a difference 3250 between images 3200 and the corresponding Gaussian fit 3240 are shown below the respective image 3200. Additionally, x and y cross sections 3260 of the data are shown below the respective image 3200 and Gaussian fit 3240.

The attribute, in this case, the ellipticity ε, is determined from the fluorescent image 3200 by taking the Gaussian fit 3240 of the fluorescent image. The ellipticity ε is determined from the following equation:

$$\varepsilon = \frac{\sigma_x - \sigma_y}{\sigma_x + \sigma_y},$$

where $\sigma_x$ and $\sigma_y$ are the standard deviations (Gaussian widths) of the corresponding Gaussian fits 3240. As described in the other implementations below, other attributes (like differential phase angle or peak brightness) can be used depending on the design of the apparatus.

Figure 33:
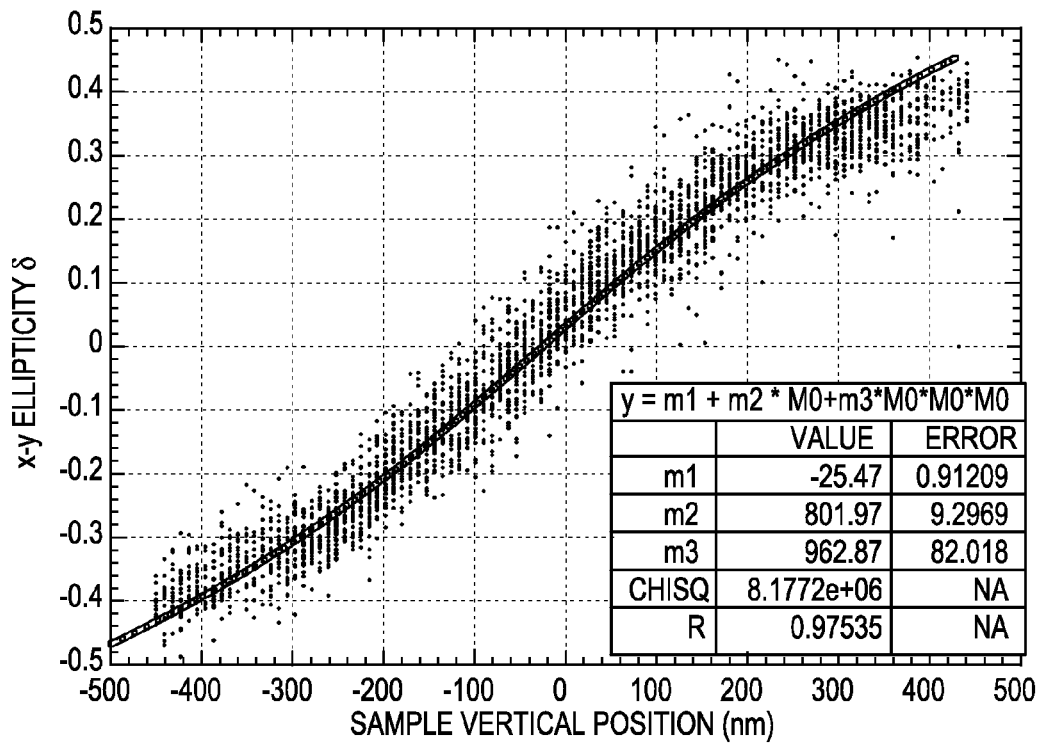
FIG. 33 is a graph of ellipticity versus vertical position of the same optical source of FIG. 31A.

Next, as shown in FIG. 33, ellipticity ϵ is measured relative to the known vertical position Z of a point optical source for a field of about 40 gold nanoparticles spread over a field of about 25 μm×25 μm. The raw data is shown as points. Additionally, the raw data is fit to an equation $Z_\epsilon = m_1 + m_2 \cdot \epsilon + m_3 \cdot \epsilon^3$. Although the measured dependence of the ellipticity ϵ on the vertical position δ of the optical source has a lower accuracy then the accuracy of the determined first and second orthogonal positions, this dependence is not limited to a single interferometric fringe and is merely used to determine the fringe order, which, in turn, allows for accurate determination of the vertical position δ over a wide range of optical source positions. This determination is performed as follows.

Figure 34:
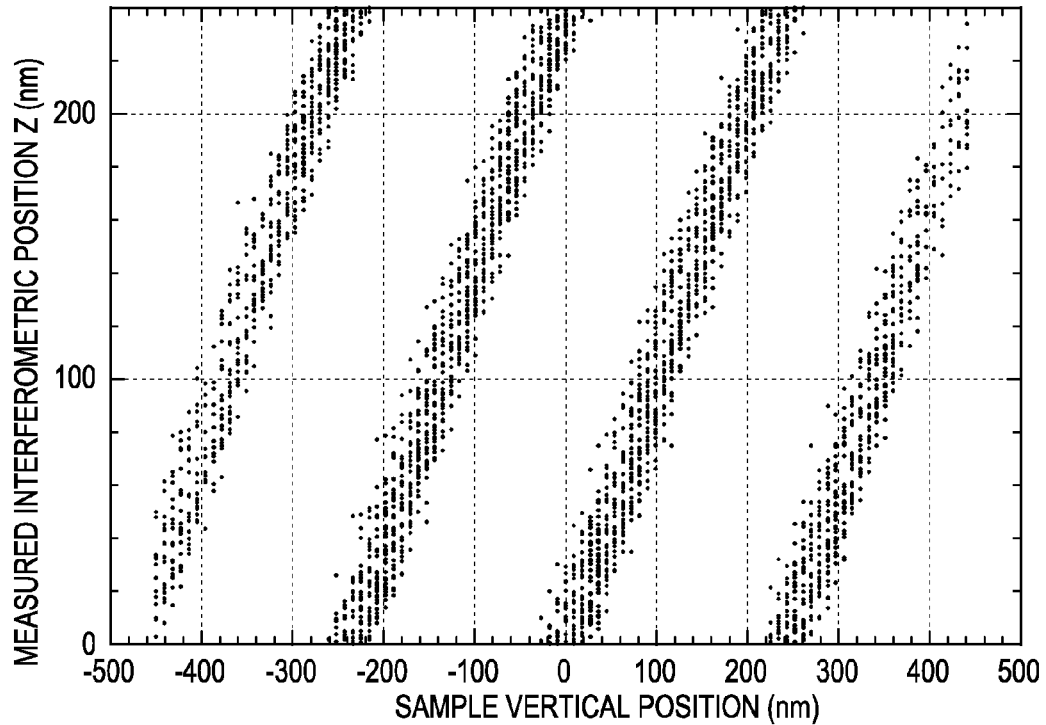
FIG. 34 is a graph of a measured vertical position (a set of orthogonal positions determined using only interferometric data) versus actual vertical position of the sample optical source of FIG. 31A.
Figure 35:
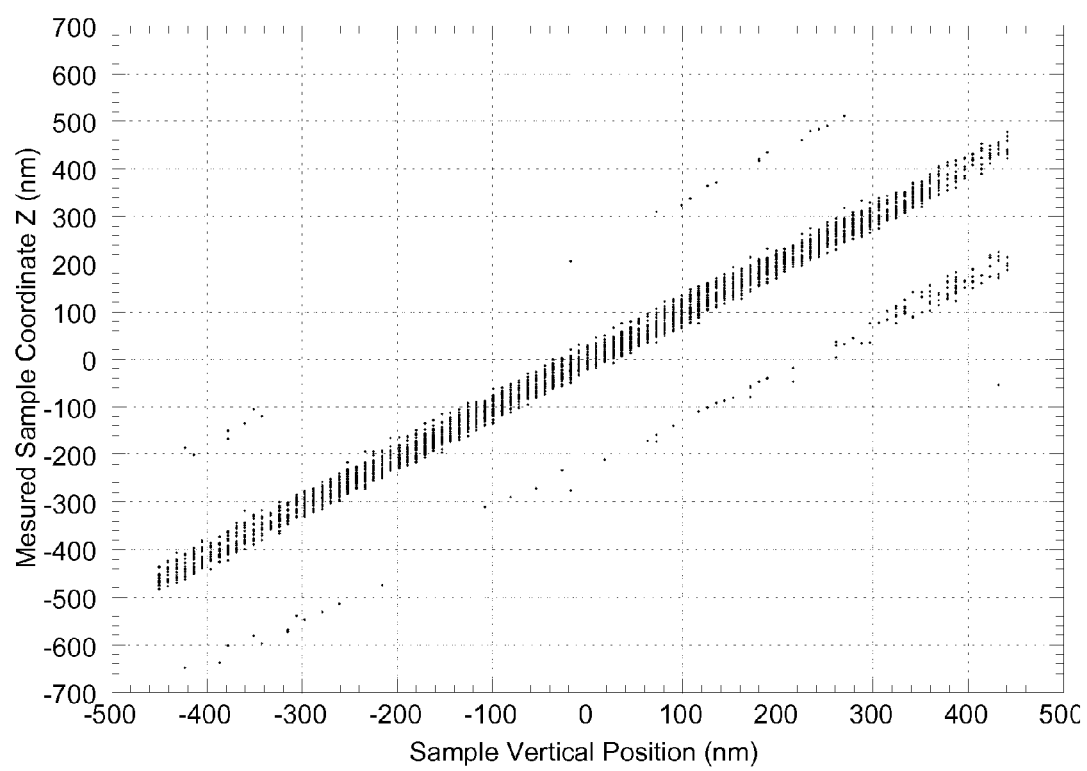
FIG. 35 is a graph of the estimated vertical position versus the actual vertical position of the sample optical source of FIG. 31A using the data from the graphs of FIGS. 33 and 34.

During calibration of the apparatus 2800 or 3000, the raw data of the attribute (in this case, the ellipticity ϵ) versus the sample vertical position Z of the point optical source is recorded (as shown in FIG. 33) and the peak intensity in each of the three detectors versus sample vertical position Z of the point optical source is recorded. From this peak intensity, a set of possible vertical positions, $Z_{interf}$, can be determined. The set of possible vertical positions $Z_{interf}$ versus sample vertical position Z is shown in the graph of FIG. 34. The actual vertical position δ can be calculated using the following formula:

$$Z = Z_{interf} + Z_{interf\text{-}range} \cdot \text{Round}\left(\frac{Z_\epsilon - Z_{interf}}{Z_{inter\text{-}range}}\right),$$

where $Z_{interfrange}$ is the period of the vertical distance that repeats. For example, as shown in FIG. 33, $Z_{interfrange}$ is about 240 nm because for every 240 nm of the sample vertical position, the measured value of $Z_{interf}$ repeats. The value of $Z_{interfrange}$ depends on the wavelength of the optical beam and the index of refraction n of the sample medium, and can be estimated to be about λ/2·n. The term "Round" merely rounds the value of the argument to a nearest integer value to avoid contaminating the more accurate value $Z_{interf}$ with the less accurate second term in the equation. The Round operation essentially extracts only the integer order of the interference fringe. Using the data from FIGS. 33 and 34, the results of the calculation are shown in FIG. 35. As can be seen the calculation works well over a range of about 700 nm, which is close to a depth of field of a high numerical aperture objective that was used in the experiment. An error ratio of the number of incorrectly determined interferometric fringe orders relative to a total number of measured points over the range from about −450 nm to +300 nm is about 2.9%. Moreover, the error rate can be reduced by introducing an uncertainty parameter $Z_u$ given by $Z_\epsilon - Z$ and by filtering out data where $Z_u$ is outside of an acceptable range.

Figures 36A, 36B:
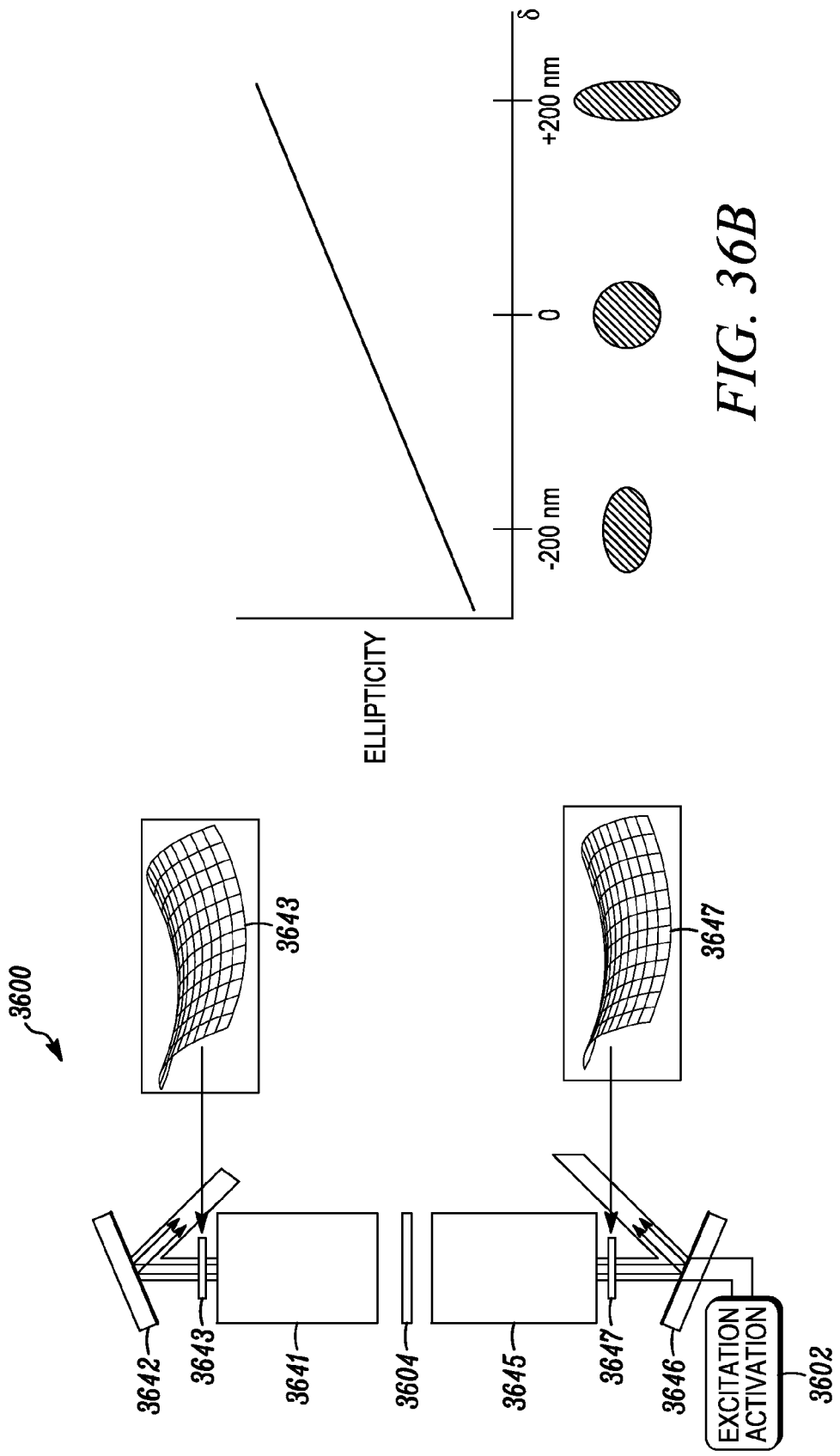
FIG. 36A is a block diagram of an exemplary portion of the interferometric microscope system of FIG. 28.
FIG. 36B is a generalized graph of the ellipticity versus vertical position of the optical source of a sample in the system of FIG. 36A.

Referring also to FIG. 36A, a multi-phase interferometric microscopy apparatus 3600 includes lenses 3643, 3647 placed between respective objectives 3641, 3645 and mirrors 3642, 3646. The mirrors 3642, 3646 can be made flat so that they impart no wavefront modification to the optical beam emitted from the sample 3604. In this case, though, the lenses 3643, 3647 provide the wavefront modification to the curvature of the respective optical beam emitted from sample 3604. Therefore, the lenses 3643, 3647 can each be cylindrical (curved along only one direction) or they can be biconic (that is, curved oppositely along two transverse directions and having a saddle or hyperbolic paraboloid shape, in a similar fashion as the surfaces of the mirrors 3142, 3146).

For example, the surface of the lens 3643 can be convex along a first direction that is transverse to the beam propagation direction and concave along a second direction that is transverse to the beam propagation direction and to the first direction, as shown in the perspective view of the lens 3643. Moreover, the surface of the lens 3647 can be concave along a first direction that is transverse to the beam propagation direction and convex along a second direction that is transverse to the beam propagation direction and to the first direction, as shown in the perspective view of the lens 3647. The lenses 3643, 3647 are designed to have opposite or complementary shapes so that the wavefronts of the optical beams overlay with each other after passing through the interference system, that is, the wavefronts of the combined beams overlay with each other at the detectors (which are shown in FIGS. 28 and 30).

The optical beam that impinges upon the lens 3643, 3647 is collimated in that its wavefront is flat along both directions that are transverse to the beam propagation direction. Thus, the lens 3643 or 3647 breaks up the symmetry between the transverse directions so that the wavefront is no longer flat in both transverse directions. The lenses 3643, 3647 in the apparatus 3600 serve the same purpose as the modified mirrors 3142, 3146 in the apparatus 3100 in that they both serve to modify the curvature of the wavefront to create two slightly different focal planes for the two transverse directions relative to the respective beam propagation direction. As a result, as shown in FIG. 36B, the ellipticity and orientation of the image varies as the position of the optical source in the third orthogonal dimension changes relative to the sample plane (which is the location at which the vertical position δ is zero). This information can be used by the processor, as discussed above, to determine the position of the optical source in the third orthogonal dimension.

Figure 37B:
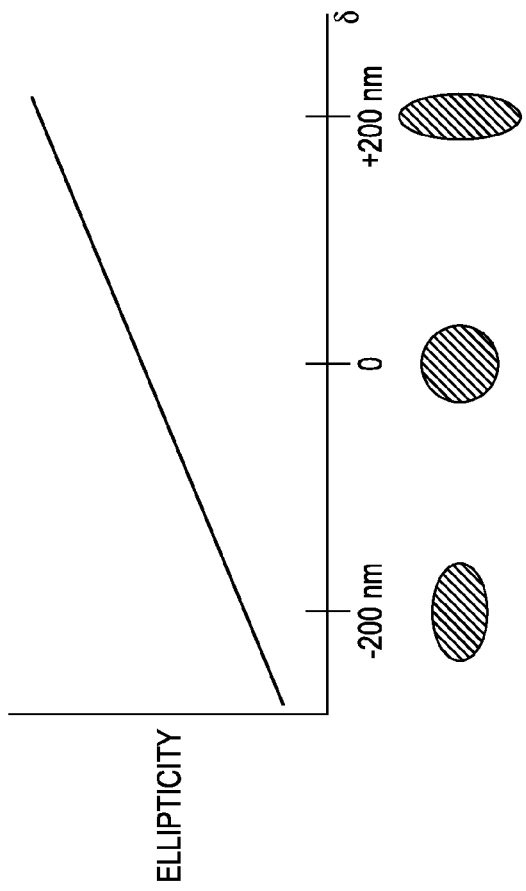
FIG. 37B is a generalized graph of the ellipticity versus vertical position of the optical source of a sample in the system of FIG. 37A.
Figure 37A:
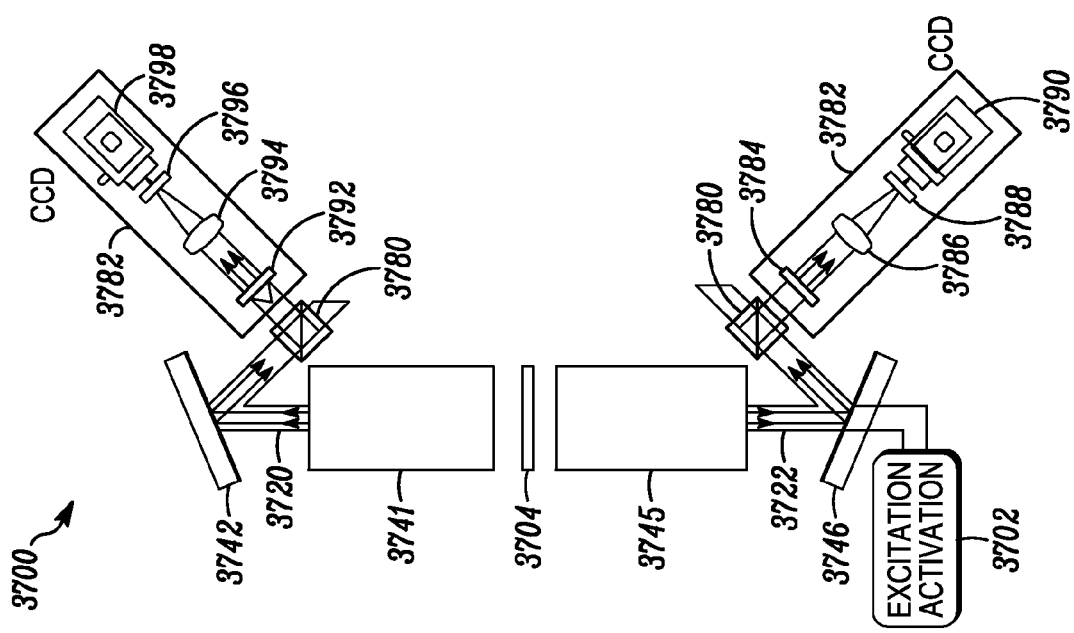
FIG. 37A is a block diagram of an exemplary portion of the interferometric microscope system of FIG. 28.
Figure 38:
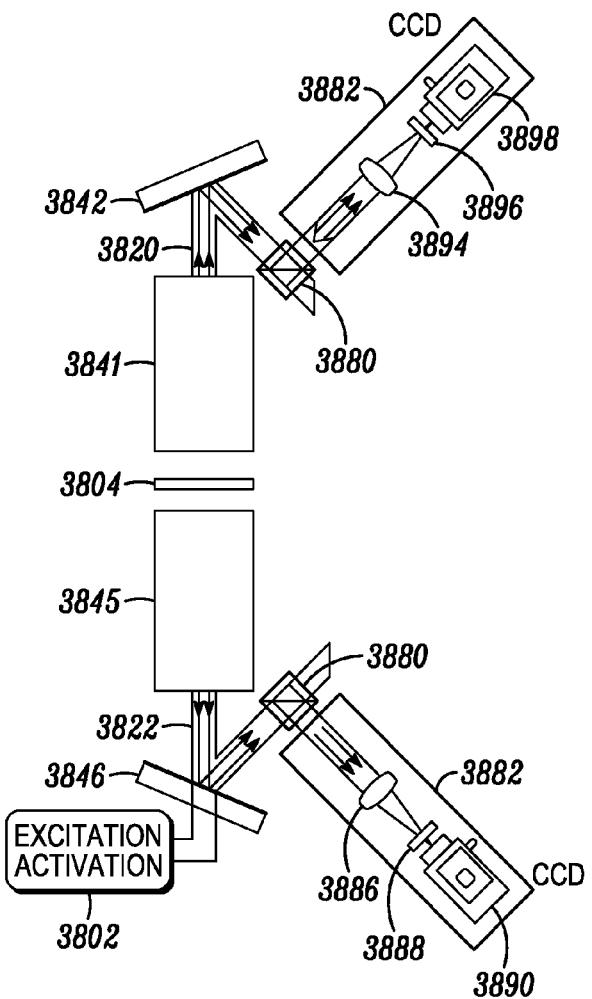
FIG. 38 is a block diagram of an exemplary portion of the interferometric microscope system of FIG. 28.

Referring to FIG. 37A, in another implementation, a multi-phase interferometric microscopy apparatus 3700 includes beam splitters 3780 positioned in each of the optical paths 3720, 3722 to filter out a small percentage of light that would otherwise be directed to the interference system (such as the interference system 2806 of FIG. 28). Each beam splitter 3780 directs the light toward a respective detector system 3782, each of which includes optical components and a detector that is also connected to the processor (such as the processor 2814 of FIG. 28). The detectors can be, for example, charge coupled devices (CCDs) or electron-multiplying charge coupled detectors (EMCCDs). In particular, the bottom detector system 3782 includes a wavefront symmetry breaking lens 3784 that receives the optical beam from the bottom beam splitter 3780, a converging lens 3786 that focuses the optical beam, a filter 3788 that blocks light outside of a certain range of wavelengths, and a detector 3790. The wavefront symmetry breaking lens 3784 actively introduces the variable wavefront modification to the optical beam, similarly to the lens 3647 in the apparatus 3600 shown in FIG. 36A. The top detector system 3782 includes a wavefront symmetry breaking lens 3792 that receives the optical beam from the top beam splitter 3780, a converging lens 3794 that focuses the optical beam, a filter 3796 that blocks light outside of a certain range of wavelengths, and a detector 3798. The wavefront symmetry breaking lens 3792 actively introduces the variable wavefront modification to the optical beam, similarly to the lens 3643 in the apparatus 3600 shown in FIG. 36A. The lenses 3784 and 3792 are designed like the lenses 3647 and 3643 in the apparatus 3600 of FIG. 36A, and therefore the lenses create two slightly different focal planes for the two transverse directions relative to the respective beam propagation direction at the respective detectors 3790, 3798. As a result, as shown in FIG. 37B, the ellipticity and orientation of the image varies as the position of the optical source in the third orthogonal dimension changes relative to the sample plane (which is the location at which the vertical position δ is zero). This information can be used, as discussed above, by the processor (such as the processor 2814 of FIG. 28) connected to the detectors 3790, 3798 to determine the position of the optical source in the third orthogonal dimension.

Referring to FIG. 38, in another implementation, a multiphase interferometric microscopy apparatus 3800 includes beam splitters 3880 positioned in each of the optical paths 3820, 3822 to filter out a small percentage of light that would otherwise be directed to the interference system (such as the interference system 2806 of FIG. 28). Each beam splitter 3880 directs the light toward a respective detector system 3882, each of which includes optical components and a detector that is also connected to the processor (such as the processor 2814 of FIG. 28). The detectors can be, for example, charge coupled devices (CCDs) or electron-multiplying charge coupled detectors (EMCCDs). In particular, the bottom detector system 3882 includes a converging lens 3886 that receives the optical beam from the bottom beam splitter 3880 and focuses the optical beam, a filter 3888 that blocks light outside of a certain range of wavelengths, and a detector 3890. The top detector system 3882 includes a converging lens 3894 that receives the optical beam from the top beam splitter 3880 and that focuses the optical beam, a filter 3896 that blocks light outside of a certain range of wavelengths, and a detector 3898.

The detector systems 3882 are set up to detect two axially separated sample planes. In this detection scheme, one or more of the detectors 3890, 3898 can be moved from the standard image plane and/or one or more of the lenses 3886, 3894 can be moved to place the image planes just in front of or just behind the detectors 3890, 3898 resulting in an over- or under-focused image of the standard (z=0) object (sample) plane. By doing this, an independent z dependence of the focus is observed in the detectors 3890, 3898.

This information can be used by the processor to determine the position of the optical source in the third orthogonal dimension by comparing a normalized peak brightness of a first image B1 with a normalized peak brightness B2 of a second image at the detector 3898, 3890. Thus, if the peak brightness of the first image at the detector is b1 and the peak brightness of the second image at detector is b2, then the normalized peak brightness of the first image is B1 or b1/(b1+b2), and the normalized peak brightness of the second image is B2 or b2/(b1+b2). The processor therefore determines the difference B1−B2 to provide an indication of defocus, and follows the procedures described above to determine the vertical position of the optical source.

In other implementations, the processor uses information about the fitted radius or spot size of the first and second images to indicate defocus.

Referring to FIG. 39A, in another implementation, a multiphase interferometric microscopy apparatus 3900 includes mirrors 3942, 3946 that have been modified to have an inner diameter pupil region 3980 separated from an outer annular region 3984. The mirrors 3942, 3946 can have a double mirrored surface, each mirrored surface being oriented at two distinct reflection angles relative to the other. For example, the difference in angle between the inner and outer regions can be about 0.1-1°, and this difference is enough to generate a double image of an optical source on a detector.

Because of this design, each of the mirrors 3942, 3946 provides two separate optical beams (an inner optical beam from the inner diameter pupil region 3980 and an outer optical beam from the outer annular region 3984) that interfere separately in the interference system (such as the interference system 2806 of FIG. 28). Two images are captured on each detector 2808, 2810, 2812, one from the inner optical beam component, which travels a shorter distance to the detector, and one from the outer optical beam component, which travels a longer distance to the detector, of the combined beam. The inner optical beam has a faster phase wind so position can be determined from a differential phase angle (which is the difference in phase between the inner optical beam and the outer optical beam), as shown in FIG. 39B, which displays a graph of the differential phase angle versus vertical position of the optical source.

The detectors are set up to detect two axially separated sample planes due to the two images captured from the inner optical beam component and the outer optical beam component. In this detection scheme, as discussed in detail above, photo-activated localization interferometric microscopy determines the position of the optical source in the first and second orthogonal dimensions and determines the set of possible positions of the optical source in the third orthogonal dimension. Photo-activated localization interferometric microscopy can be performed on either the inner component or the outer component simultaneously with determining the actual position of the optical source in the third orthogonal dimension.

Figure 40B:
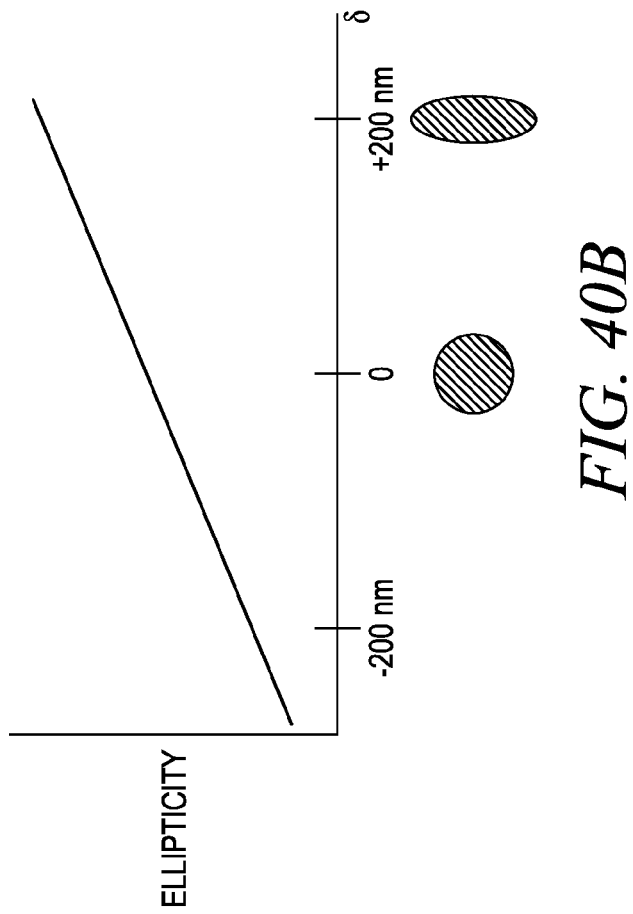
FIG. 40B is a generalized graph of the ellipticity versus vertical position of the optical source of a sample in the system of FIG. 40A.
Figure 40A:
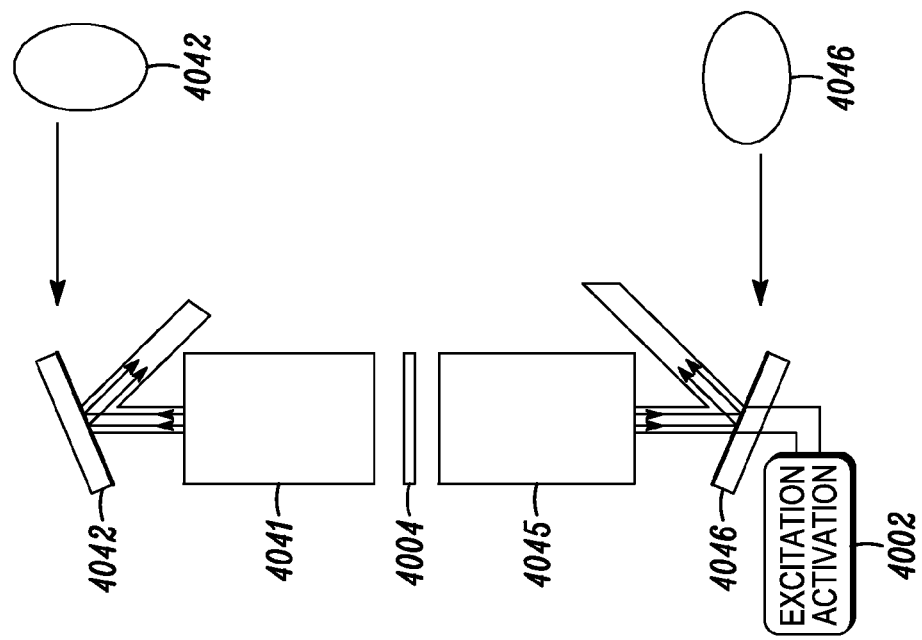
FIG. 40A is a block diagram of an exemplary portion of the interferometric microscope system of FIG. 28.

Referring to FIG. 40A, in another implementation, a multiphase interferometric microscopy apparatus 4000 includes mirrors 4042, 4046, the shape of which have been modified to maintain the planar symmetry (since they do not modify the wavefront curvature) and to break the rotational symmetry of the wavefronts. In this case, each mirror 4042, 4046 is modified by removed a wing region from a circularly shaped mirror to form a generally oval mirror, where each mirror is rotated by about 90° relative to the other mirror so that they each produce different shapes that are dependent on the vertical position of the optical source. Thus, when the optical beams reflected from the mirrors 4042, 4046 are interfered in the interference system, and recombined to form the combined beams, the optical beams are entirely overlapped along a central region but are not overlapped at the wing region. In this case, the point spread or image symmetry is modified by the modification of the shape of the mirrors and it can be said that the amplitude and/or shape of the image is modulated by the modification of the shape of the mirrors. Because the shapes are dependent on the vertical position of the optical source, this information can be used by the processor to determine the vertical position of the optical source by analyzing the image shapes that impinge upon the detectors based on a calibration of the apparatus 4000 using known optical sources. It is expected that the image shapes should display some ellipticity signature because the mirrors 4042, 4046 are modified with some elliptical like change (in that there is more mirror along one axis than the other).

In another implementation that involves measuring the separation of planes that arise from the relative placement of the detectors and the basic focusing lens, an apparatus can be designed without any substantial modifications to components of the basic design shown in FIG. 30, for example. Instead, the apparatus can be set up so that the detectors 3008, 3010, 3012 are moved relative to the interference system 3006 and/or the focusing lenses within the optical components 3050, 3054, 3058 are moved relative to the interference system 3006 so that each of the detectors are focused to distinct image planes. For example, the detector 3010 could be defocused in one direction relative to the detector 3008, and the detector 3012 could be defocused in an opposite direction relative to the detector 3008. In this case, the image radiuses in each of the three detectors may provide information that is dependent on the vertical position of the optical source and this can be used to determine the vertical position.

In still other implementations, the multi-phase interferometric microscopy apparatus 3800 can be designed to have just one detector system 3882, and that detector system 3882 can be moved along with one or more of the main detectors 3008, 3010, 3012 to enable defocus of one or more of the detectors, where such defocus is dependent on the vertical position of the optical source.

Some implementations include a processor and a related processor-readable medium having instructions or computer code thereon for performing various processor-implemented operations. Such processors can be implemented as hardware modules such as embedded microprocessors, microprocessors as part of a computer system, Application-Specific Integrated Circuits ("ASICs"), and Programmable Logic Devices ("PLDs"). Such processors can also be implemented as one or more software modules in programming languages as Java, C++, C, assembly, a hardware description language, or any other suitable programming language. A processor includes media and computer code (also can be referred to as code) specially designed and constructed for the specific purpose or purposes. Examples of processor-readable media include, but are not limited to: magnetic storage media such as hard disks, floppy disks, and magnetic tape; optical storage media such as Compact Disc/Digital Video Discs ("CD/DVDs"), Compact Disc-Read Only Memories ("CD-ROMs"), and holographic devices; magneto-optical storage media such as floptical disks, and read-only memory ("ROM") and random-access memory ("RAM") devices. Examples of computer code include, but are not limited to, micro-code or micro-instructions, machine instructions, such as produced by a compiler, and files containing higher-level instructions that are executed by a computer using an interpreter. For example, the processor-implemented instructions may be implemented using Java, C++, or other object-oriented programming language and development tools. Additional examples of computer code include, but are not limited to, control signals, encrypted code, and compressed code.

While certain implementations have been shown and described above, it will be understood by those skilled in the art that various changes in form and details may be made. For example, variations in illumination techniques are possible and can allow an improvement to the modulo λ/2 periodicity of the intensity data. In addition, the various implementations described in the Betzig references can be combined with the various implementations described herein. For example, in one implementation, top/bottom TIRF illumination can allow for measurements of a sample having a thickness up to one wavelength, λ. In alternative implementations, coherent rephasing of short pulses can form an illumination plane. In yet other implementations, side illumination to form a Gaussian waist at the sample at various heights in the z-coordinate can further extend the range in the z-coordinate direction without resorting to physical sectioning. Thus, it should be understood that the systems described herein can include various combinations and/or sub-combinations of the components and/or features of the different implementations described.

Other implementations are within the scope of the following claims.

What is claimed is:

1. A method, comprising:
   optically actuating an optical source in a sample that extends generally along a sample plane defined by first and second orthogonal dimensions to cause the optical source to emit optical beams in a plurality of propagation directions;
   interfering two or more optical beams emitted from the optical source to produce a plurality of output beams directed to a plurality of detectors;
   determining a position of the optical source in the first orthogonal dimension and the second orthogonal dimension based on a center region of an image of each output beam from the plurality of output beams;
   determining a set of possible positions of the optical source in a third orthogonal dimension that is perpendicular to the sample plane based on separately detected intensities of each of the plurality of output beams;
   analyzing the shape of an image of one or more of an optical beam and an output beam based on a wavefront modification that varies with the position of the optical source in the third orthogonal dimension, wherein the wavefront modification is a modification of one or more of a curvature and a shape of a wavefront of at least one optical beam emitted from the optical source; and
   determining the position of the optical source in the third orthogonal dimension out of the possible set of positions based on the analyzed shape.

2. The method of claim 1, wherein analyzing the shape of the one or more images includes comparing the wavefront modification with predetermined wavefront modifications.

3. The method of claim 1, wherein analyzing the shape of the one or more images includes comparing the wavefront modification with modeled wavefront modifications.

4. The method of claim 1, wherein analyzing the shape of the one or more images includes analyzing a complex phase that is induced by the wavefront modifications and varies with the position of the optical source in the third orthogonal dimension.

5. The method of claim 1, wherein determining the position of the optical source in the third orthogonal dimension out of the possible set of positions includes comparing the shape of the one or more images to predetermined shapes of images that are determined based on predetermined wavefront modifications.

6. The method of claim 1, further comprising introducing the wavefront modification in the at least one optical beam.

7. The method of claim 6, wherein introducing the wavefront modification in the at least one optical beam includes introducing a separation along a propagation direction between focal planes each having a focus in a respective transverse direction relative to the beam propagation direction.

8. The method of claim 6, wherein introducing the wavefront modification in the at least one optical beam includes introducing a curvature in the wavefront along one or more transverse directions relative to the beam propagation direction.

9. The method of claim 6, wherein introducing the wavefront modification in the at least one optical beam includes varying a brightness of the image of the at least one optical beam.

10. The method of claim 9, wherein the brightness of the image is varied along one transverse direction in a way that is distinct from the second transverse direction of one or more of the optical beams and output beams.

11. An apparatus comprising:
an optical actuation system configured to cause an optical source in a sample that extends generally along a sample plane to emit optical beams in a plurality of optical paths;
an interference system configured to receive first and second optical beams emitted from the optical source, divide each of the optical beams into two or more divided beams, and combine at least two or more of the divided beams to form a plurality of combined beams, wherein each of the combined beams includes an interference between the two or more divided beams caused at least in part by a difference in a source phase between the optical beams due to a difference in the optical path length of the optical beams relative to the location of the optical source;
at least two detectors configured to separately detect one or more of an intensity and a profile of each of the combined beams output from the interference system; and
a processor configured to:
receive the output from the at least two detectors;
calculate a position of the optical source in the sample plane to sub-diffractive accuracy based on a center region of an image of each combined beam;
calculate a set of possible positions of the optical source in a third orthogonal dimension that is perpendicular to the sample plane based on separately detected intensities of each combined beam;
analyze the shape of an image of one or more of an optical beam and a combined beam based on a wavefront modification that varies with the position of the optical source in the third orthogonal dimension, wherein the wavefront modification is a modification of one or more of a curvature and a shape of a wavefront of at least one optical beam emitted from the optical source; and
determine the position of the optical source in the third orthogonal dimension out of the set of possible positions based on the analyzed shape.

12. The apparatus of claim 11, wherein the optical actuation system is optically coupled to the sample and configured to activate a statistically sparse subset of switchable optical sources in the sample and excite the activated switchable optical sources such that the optical beams are emitted from the activated switchable optical sources along at least two optical paths that are directed to the interference system.

13. The apparatus of claim 12, further comprising:
first optical components configured to receive the first optical beam emitted along a first optical path and to at least redirect the first optical beam toward the interference system; and
second optical components configured to receive the second optical beam emitted along a second optical path and to at least redirect the second optical beam toward the interference system.

14. The apparatus of claim 11, further comprising a wavefront modification system in at least one of the optical paths configured to introduce the variable wavefront modification of at least one optical beam.

15. The apparatus of claim 14, wherein the wavefront modification system comprises a defocusing system in at least one of the optical paths configured to separate focal planes along transverse directions of one or more optical beams and combined beams.

16. The apparatus of claim 15, wherein the defocusing system comprises:
a first defocusing system in a first optical path of a first optical beam between the optical source and the interference system and configured to separate focal planes along the transverse directions of the first optical beam; and
a second defocusing system in a second optical path of a second optical beam between the optical source and the interference system and configured to separate focal planes along the transverse directions of the second optical beam.

17. The apparatus of claim 15, wherein the defocusing system is between the sample and the interference system.

18. A method comprising:
activating a statistically sparse subset of switchable optical sources in a sample;
exciting the activated switchable optical sources such that optical beams are emitted from the activated switchable optical sources along at least two optical paths;
introducing a first wavefront modification in a first optical beam emitted from the activated switchable optical sources along a first optical path and introducing a second wavefront modification in a second optical beam emitted from the activated switchable optical sources along a second optical path, the second wavefront modification being distinct from the first wavefront modification;
interfering the first and second optical beams to produce a plurality of output beams; and
determining three-dimensional position information of the optical sources based on an intensity of each output beam from the plurality of output beams.

19. The method of claim 18, wherein the second wavefront modification is opposite in direction to the first wavefront modification.

20. The method of claim 18, wherein introducing the first wavefront modification includes shifting, by a first shift value, the focal plane of the first optical beam along a first transverse direction relative to the focal plane of the first optical beam along a second transverse direction, in which the first and second transverse directions are transverse to the first optical path.

21. The method of claim 18, wherein introducing the second wavefront modification includes shifting, by a second shift value, the focal plane of the second optical beam along a first transverse direction relative to the focal plane of the second optical beam along a second transverse direction, in which the first and second transverse directions are transverse to the second optical path and the second shift value is opposite to the first shift value.

22. The method of claim 18, wherein:
introducing the first wavefront modification includes under-focusing the first optical beam emitted from the activated switchable optical sources along at least one direction that is transverse to the first optical path; and
introducing the second wavefront modification includes over-focusing the second optical beam emitted from the activated switchable optical sources along at least one direction that is transverse to the second optical path.

23. The method of claim 18, further comprising forming collimated optical beams before introducing the first and second wavefront modifications to the first and second optical beams.

24. The method of claim 18, wherein determining three-dimensional position information comprises determining the position of the optical source in a dimension that is perpendicular to a sample plane across which the sample generally extends.

25. The method of claim 18, wherein:
introducing the first wavefront modification in the first optical beam includes introducing a wavefront curvature in the first optical beam; and
introducing the second wavefront modification in the second optical beam includes introducing a wavefront curvature in the second optical beam.

26. The method of claim 18, wherein each wavefront modification is a modification of one or more of a curvature and a shape of a wavefront of the respective optical beam.

27. A method comprising:
directing first and second optical beams emitted from an optical point source along first and second distinct directions associated with respective first and second distinct optical paths;
shifting by a first shift value focal planes for transverse directions of the first optical beam in the first optical path and shifting by a second shift value focal planes for transverse directions of the second optical beam in the second optical path, in which the second shift value is opposite to the first shift value;
after shifting the focal planes of the first and second optical beams, dividing each of the first and second optical beams into two or more divided beams and combining at least two or more of the divided beams to form a plurality of combined beams, in which each of the combined beams includes an interference between the two or more divided beams caused at least in part by a difference in the lengths of the optical paths of the first and second optical beams;
separately detecting an image of each of the combined beams;
determining a position of the optical source in a first orthogonal dimension and a second orthogonal dimension; and
determining a position of the optical source in a third orthogonal dimension based on the separately detected images of each of the combined beams.

28. The method of claim 27, wherein determining the position of the optical source in the third orthogonal dimension based on the separately detected images of each of the combined beams includes determining the position of the optical source by comparing the intensities of separately detected images to predetermined values.

* * * * *